US009422525B2

(12) United States Patent
Heng et al.

(10) Patent No.: US 9,422,525 B2
(45) Date of Patent: Aug. 23, 2016

(54) NUCLEAR RECEPTOR AND MUTANT THEREOF AND THE USE OF THE SAME IN THE REPROGRAMMING OF CELLS

(75) Inventors: Dominic Jian-Chien Heng, Singapore (SG); Huck Hui Ng, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/499,607

(22) PCT Filed: Sep. 30, 2010

(86) PCT No.: PCT/SG2010/000372

§ 371 (c)(1),
(2), (4) Date: Mar. 30, 2012

(87) PCT Pub. No.: WO2011/040887

PCT Pub. Date: Apr. 7, 2011

(65) Prior Publication Data

US 2012/0189596 A1    Jul. 26, 2012

(30) Foreign Application Priority Data

Sep. 30, 2009   (SG) .............................. 200906546-7
Jan. 9, 2010    (SG) .............................. 201000140-2

(51) Int. Cl.
*A61K 35/12*    (2015.01)
*A61K 35/545*   (2015.01)
*C12N 15/85*    (2006.01)
*C12N 5/074*    (2010.01)

(52) U.S. Cl.
CPC ......... *C12N 5/0696* (2013.01); *C12N 2501/38* (2013.01); *C12N 2501/602* (2013.01); *C12N 2501/604* (2013.01); *C12N 2501/606* (2013.01); *C12N 2510/00* (2013.01)

(58) Field of Classification Search
None
See application file for complete search history.

(56) References Cited

U.S. PATENT DOCUMENTS

2009/0304646 A1*  12/2009  Sakurada et al. ............ 424/93.7
2012/0315703 A1*  12/2012  Liu et al. ..................... 435/455

FOREIGN PATENT DOCUMENTS

| WO | WO-03/072788 A1  | 9/2003  |
| WO | WO 2007/069666   | 6/2007  |
| WO | WO-2009/136867 A1 | 11/2009 |
| WO | WO-2009/149233 A1 | 12/2009 |
| WO | 2011/027180 A1   | 3/2011  |
| WO | WO-2011/040887 A1 | 4/2011  |

OTHER PUBLICATIONS

Peili Gu, et al., Orphan Nuclear Receptor LRH-1 Is Required to Maintain Oct4 Expression at the Epiblast Stage of Embryonic Development. Molecular and Cellular Biology, May 2005, vol. 25, p. 3492-3505.*
Hitoshi Niwa. How is pluripotency determined and maintained? Development 134, 635-646 (2007).*
Gu, P. et al. Orphan nuclear receptor LRH-1 is required to maintain Oct4 expression at the epiblast stage of embryonic development. Mol. Cell. Biol. 25, 3492-3505 (2005).*
Yang et al., Liver receptor homolog-1 localization in the nuclear body is regulated by sumoylation and cAMP signaling in rat granulosa cells. FEBS Journal 276 (2009) 425-436.*
Guo et al., Expression and activation of the reprogramming transcription factors. Biochemical and Biophysical Research Communications 390 (2009) 1081-1086.*
International Search Report and Written Opinion mailed Dec. 14, 2010 in connection with PCT/SG2010/000372.
International Preliminary Report on Patentability mailed Oct. 7, 2011 in connection with PCT/SG2010/000372.
Carey et al., Reprogramming of murine and human somatic cells using a single polycistronic vector. Proc Natl Acad Sci U S A. Jan. 6, 2009;106(1):157-62. Epub Dec. 24, 2008. Erratum in: Proc Natl Acad Sci U S A. Jul. 14, 2009;106(28):11818. Proc Natl Acad Sci U S A. Mar. 31, 2009;106(13):5449.
Chen et al., Integration of external signaling pathways with the core transcriptional network in embryonic stem cells. Cell. Jun. 13, 2008;133(6):1106-17.
Feng et al., Molecules that promote or enhance reprogramming of somatic cells to induced pluripotent stem cells. Cell Stem Cell. Apr. 3, 2009;4(4):301-12.
Feng et al., Reprogramming of fibroblasts into induced pluripotent stem cells with orphan nuclear receptor Esrrb. Nat Cell Biol. Feb. 2009;11(2):197-203. Epub Jan. 11, 2009. Supplemental material included.
Galarneau et al., The alpha1-fetoprotein locus is activated by a nuclear receptor of the *Drosophila* FTZ-F1 family. Mol Cell Biol. Jul. 1996;16(7):3853-65.
Heng et al., The nuclear receptor Nr5a2 can replace Oct4 in the reprogramming of murine somatic cells to pluripotent cells. Cell Stem Cell. Feb. 5, 2010;6(2):167-74. Epub Jan. 21, 2010.
Ichida et al., A small-molecule inhibitor of tgf-Beta signaling replaces sox2 in reprogramming by inducing nanog. Cell Stem Cell. Nov. 6, 2009;5(5):491-503. Epub Oct. 8, 2009.
Lewitzky et al., Reprogramming somatic cells towards pluripotency by defined factors. Curr Opin Biotechnol. Oct. 2007;18(5):467-73.
Maherali et al., Tgfbeta signal inhibition cooperates in the induction of iPSCs and replaces Sox2 and cMyc. Curr Biol. Nov. 3, 2009;19(20):1718-23. Epub Sep. 17, 2009.

(Continued)

*Primary Examiner* — Kevin Hill
*Assistant Examiner* — Arthur S Leonard
(74) *Attorney, Agent, or Firm* — Wolf, Greenfield & Sacks, P.C.

(57) ABSTRACT

According to the invention there is provided methods for inducing pluripotent stem cells in vitro, comprising introducing a gene or polypeptide of a nuclear receptor and one or more gene or polypeptide selected from the group consisting of Sox, Krüppel-like factor or the myc family, to cells in vitro. The present invention also provides vectors and compositions for producing the same and methods for using the induced pluripotent stem cell for treating a patient in need of a pluripotent stem cell treatment.

15 Claims, 19 Drawing Sheets

(56) References Cited

OTHER PUBLICATIONS

Mullen et al., Nuclear receptors in regulation of mouse ES cell pluripotency and differentiation. PPAR Research. Hindawi Publishing Corporation. 2007 [Online]. vol. 2007. Article ID 61563. 10 pages. Retrieved from the Internet: doi: 10.1155/2007/61563.

Nakagawa et al., Generation of induced pluripotent stem cells without Myc from mouse and human fibroblasts. Nat Biotechnol. Jan. 2008;26(1):101-6. Epub Nov. 30, 2007.

Pare et al., The fetoprotein transcription factor (FTF) gene is essential to embryogenesis and cholesterol homeostasis and is regulated by a DR4 element. J Biol Chem. May 14, 2004;279(20):21206-16. Epub Mar. 10, 2004.

Sablin et al., Structural basis for ligand-independent activation of the orphan nuclear receptor Lrh-1. Mol Cell. Jun. 2003;11(6):1575-85.

Silva et al., Nanog is the gateway to the pluripotent ground state. Cell. Aug. 20, 2009;138(4):722-37.

Solomon et al., Crystal structure of the human LRH-1 DBD-DNA complex reveals Ftz-F1 domain positioning is required for receptor activity. J Mol Biol. Dec. 16, 2005;354(5):1091-102. Epub Oct. 27, 2005.

Takahashi et al., Induction of pluripotent stem cells from mouse embryonic and adult fibroblast cultures by defined factors. Cell. Aug. 25, 2006;126(4):663-76. Epub Aug. 10, 2006.

Wernig et al., c-Myc is dispensable for direct reprogramming of mouse fibroblasts. Cell Stem Cell. Jan. 10, 2008;2(1):10-2. Epub Dec. 13, 2007.

Yu et al., Induced pluripotent stem cell lines derived from human somatic cells. Science. Dec. 21, 2007;318(5858):1917-20. Epub Nov. 20, 2007.

Japanese Office Action and English translation thereof dated Dec. 9, 2014 in connection with Application No. 2012-532053.

Fayard et al., LRH-1: an orphan nuclear receptor involved in development, metabolism and steroidogenesis. Trends Cell Biol. May 2004;14(5):250-260.

Nakatake et al., Presentation summary overview. Japanese Society of Developmental Biologists Convention. 2006;39:202.

\* cited by examiner

SEQUENCE LISTING

<160> NUMBER OF SEQ ID NOS: 24

<210> SEQ ID NO 1
<211> LENGTH: 1683
<212> TYPE: DNA
<213> ORGANISM: Artificial Sequence
<220> FEATURE:
<223> OTHER INFORMATION: Sumoylated mutant of nuclear receptor construct with two lysine residues mutated

<400> SEQUENCE: 1

| | | |
|---|---|---|
| atgtctgcta gtttggatac tggagatttt caagaatttc ttaagcatgg acttacagct | 60 |
| attgcgtctg caccagggtc agagactcgc cactccccca aacgtgagga caactccgg | 120 |
| gaaaaacgtg ctgggcttcc ggaccgacac cgacgcccca ttcccgcccg cagccgcctt | 180 |
| gtcatgctgc ccaaagtgga gacggaagcc ccaggactgg tccgatcgca tggggaacag | 240 |
| gggcagatgc cagaaaacat gcaagtgtct caatttaaaa tggtgaatta ctcctatgat | 300 |
| gaagatctgg aagagctatg tcctgtgtgt ggcgataaag tgtctgggta ccattacggt | 360 |
| ctcctcacgt gcgaaagctg caagggtttt tttaagcgaa ctgtccaaaa ccaaaaaagg | 420 |
| tacacgtgca tagagaacca gaattgccaa attgacaaaa cgcagagaaa acgatgtccc | 480 |
| tactgtcgat tcaaaaaatg tatcgatgtt gggatgaggc tggaagccgt aagagccgac | 540 |
| cgcatgcgag ggggcagaaa taagtttggg ccaatgtaca agagagacag ggctttgaag | 600 |
| cagcagaaga aagccctcat tcgagccaat ggacttaagc tggaagccat gtctcaggtg | 660 |
| atccaagcaa tgcccctcaga cctgacctct gcaattcaga acattcattc cgcctccaaa | 720 |
| ggcctacctc tgagccatgt agccttgcct ccgacagact atgacagaag tcccttttgtc | 780 |
| acatctccca ttagcatgac aatgccacct cacagcagcc tgcatggtta ccaaccctat | 840 |
| ggtcactttc ctagtcgggc catcaggtct gagtacccag cccctactc cagctcacct | 900 |
| gagtcaatga tgggttactc ctacatggat ggttaccaga caaactcccc ggccagcatc | 960 |
| ccacacctga tactggaact tttgaagtgt gaaccagatg agcctcaagt tcaagcgaag | 1020 |
| atcatggctt acctccagca agagcagagt aaccgaaaca ggcaagaaaa gctgagcgca | 1080 |
| tttgggctt tatgcaaaat ggcggaccag accctgttct ccattgttga gtgggccagg | 1140 |
| agtagtatct tcttcaggga actgaaggtt gatgaccaaa tgaagctgct tcaaaactgc | 1200 |
| tggagtgagc tcttgattct cgatcacatt taccgacaag tggcgcatgg gaaggaaggg | 1260 |
| acaatcttcc tggttactgg agaacacgtg gactactcca ccatcatctc acacacagaa | 1320 |
| gtcgcgttca acaacctcct gagtctcgca caggagctgg tggtgaggct ccgttccctt | 1380 |
| cagttcgatc agcgggagtt tgtatgtctc aagttcctgg tgctgttcag ctcagatgtg | 1440 |
| aagaacctgg agaacctgca gctggtggaa ggtgtccaag agcaggtgaa tgccgccctg | 1500 |
| ctggactaca cggtttgcaa ctacccacaa cagactgaga aattcggaca gctacttctt | 1560 |
| cggctacccg agatccgggc aatcagcaag caggcagaag actacctgta ctataagcac | 1620 |
| gtgaacgggg atgtgcccta taataaccta ctcattgaga tgctgcatgc caaaagagcc | 1680 |
| taa | 1683 |

<210> SEQ ID NO 2
<211> LENGTH: 560
<212> TYPE: PRT
<213> ORGANISM: Artificial Sequence
<220> FEATURE:
<223> OTHER INFORMATION: A sumoylated mutant of Nr5a2 expression product with two lysine residues mutated

```
<400> SEQUENCE: 2

Met Ser Ala Ser Leu Asp Thr Gly Asp Phe Gln Glu Phe Leu Lys His
1               5                   10                  15

Gly Leu Thr Ala Ile Ala Ser Ala Pro Gly Ser Glu Thr Arg His Ser
                20                  25                  30

Pro Lys Arg Glu Glu Gln Leu Arg Glu Lys Arg Ala Gly Leu Pro Asp
            35                  40                  45

Arg His Arg Arg Pro Ile Pro Ala Arg Ser Arg Leu Val Met Leu Pro
        50                  55                  60

Lys Val Glu Thr Glu Ala Pro Gly Leu Val Arg Ser His Gly Glu Gln
65                  70                  75                  80

Gly Gln Met Pro Glu Asn Met Gln Val Ser Gln Phe Lys Met Val Asn
                85                  90                  95

Tyr Ser Tyr Asp Glu Asp Leu Glu Glu Leu Cys Pro Val Cys Gly Asp
            100                 105                 110

Lys Val Ser Gly Tyr His Tyr Gly Leu Leu Thr Cys Glu Ser Cys Lys
        115                 120                 125

Gly Phe Phe Lys Arg Thr Val Gln Asn Gln Lys Arg Tyr Thr Cys Ile
    130                 135                 140

Glu Asn Gln Asn Cys Gln Ile Asp Lys Thr Gln Arg Lys Arg Cys Pro
145                 150                 155                 160

Tyr Cys Arg Phe Lys Lys Cys Ile Asp Val Gly Met Arg Leu Glu Ala
                165                 170                 175

Val Arg Ala Asp Arg Met Arg Gly Gly Arg Asn Lys Phe Gly Pro Met
            180                 185                 190

Tyr Lys Arg Asp Arg Ala Leu Lys Gln Gln Lys Lys Ala Leu Ile Arg
        195                 200                 205

Ala Asn Gly Leu Lys Leu Glu Ala Met Ser Gln Val Ile Gln Ala Met
    210                 215                 220

Pro Ser Asp Leu Thr Ser Ala Ile Gln Asn Ile His Ser Ala Ser Lys
225                 230                 235                 240

Gly Leu Pro Leu Ser His Val Ala Leu Pro Pro Thr Asp Tyr Asp Arg
                245                 250                 255

Ser Pro Phe Val Thr Ser Pro Ile Ser Met Thr Met Pro Pro His Ser
            260                 265                 270

Ser Leu His Gly Tyr Gln Pro Tyr Gly His Phe Pro Ser Arg Ala Ile
        275                 280                 285

Arg Ser Glu Tyr Pro Asp Pro Tyr Ser Ser Pro Glu Ser Met Met
    290                 295                 300

Gly Tyr Ser Tyr Met Asp Gly Tyr Gln Thr Asn Ser Pro Ala Ser Ile
305                 310                 315                 320

Pro His Leu Ile Leu Glu Leu Leu Lys Cys Glu Pro Asp Glu Pro Gln
                325                 330                 335

Val Gln Ala Lys Ile Met Ala Tyr Leu Gln Gln Glu Gln Ser Asn Arg
            340                 345                 350

Asn Arg Gln Glu Lys Leu Ser Ala Phe Gly Leu Leu Cys Lys Met Ala
        355                 360                 365

Asp Gln Thr Leu Phe Ser Ile Val Glu Trp Ala Arg Ser Ser Ile Phe
    370                 375                 380

Phe Arg Glu Leu Lys Val Asp Asp Gln Met Lys Leu Leu Gln Asn Cys
385                 390                 395                 400

Trp Ser Glu Leu Leu Ile Leu Asp His Ile Tyr Arg Gln Val Ala His
                405                 410                 415
```

Gly Lys Glu Gly Thr Ile Phe Leu Val Thr Gly Glu His Val Asp Tyr
            420                 425                 430

Ser Thr Ile Ile Ser His Thr Glu Val Ala Phe Asn Asn Leu Leu Ser
        435                 440                 445

Leu Ala Gln Glu Leu Val Val Arg Leu Arg Ser Leu Gln Phe Asp Gln
    450                 455                 460

Arg Glu Phe Val Cys Leu Lys Phe Leu Val Leu Phe Ser Ser Asp Val
465                 470                 475                 480

Lys Asn Leu Glu Asn Leu Gln Leu Val Glu Gly Val Gln Glu Gln Val
                485                 490                 495

Asn Ala Ala Leu Leu Asp Tyr Thr Val Cys Asn Tyr Pro Gln Gln Thr
            500                 505                 510

Glu Lys Phe Gly Gln Leu Leu Leu Arg Leu Pro Glu Ile Arg Ala Ile
        515                 520                 525

Ser Lys Gln Ala Glu Asp Tyr Leu Tyr Tyr Lys His Val Asn Gly Asp
    530                 535                 540

Val Pro Tyr Asn Asn Leu Leu Ile Glu Met Leu His Ala Lys Arg Ala
545                 550                 555                 560

<210> SEQ ID NO 3
<211> LENGTH: 1683
<212> TYPE: DNA
<213> ORGANISM: Artificial Sequence
<220> FEATURE:
<223> OTHER INFORMATION: A sumoylation construct of Nr5a2 with five
      lysine residues mutated

<400> SEQUENCE: 3
atgtctgcta gtttggatac tggagatttt caagaatttc ttaagcatgg acttacagct        60
attgcgtctg caccagggtc agagactcgc cactccccca acgtgagga caaactccgg       120 gaaaaacgtg ctgggcttcc ggaccgacac cgacgcccca ttcccgcccg cagccgcctt       180
gtcatgctgc ccaaagtgga gacggaagcc ccaggactgg tccgatcgca tggggaacag       240
gggcagatgc cagaaaacat gcaagtgtct caatttaaaa tggtgaatta ctcctatgat       300
gaagatctgg aagagctatg tcctgtgtgt ggcgataaag tgtctgggta ccattacggt       360
ctcctcacgt gcgaaagctg caagggtttt tttaagcgaa ctgtccaaaa ccaaaaagg       420 tacacgtgca tagagaacca gaattgccaa attgacaaaa cgcagagaaa acgatgtccc       480
tactgtcgat tcaaaaaatg tatcgatgtt gggatgaggc tggaagccgt aagagccgac       540
cgcatgcgag ggggcagaaa taagtttggg ccaatgtaca agagagacag ggctttgaag       600
cagcagaaga aagccctcat tcgagccaat ggacttaggc tggaagccat gtctcaggtg       660
atccaagcaa tgcccctcaga cctgacctct gcaattcaga acattcattc cgcctccaaa       720
ggcctacctc tgagccatgt agccttgcct ccgacagact atgacagaag tccctttgtc       780
acatctccca ttagcatgac aatgccacct cacagcagcc tgcatggtta ccaaccctat       840
ggtcactttc ctagtcgggc catcaggtct gagtacccag cccctactc cagctcacct       900 gagtcaatga tgggttactc ctacatggat ggttaccaga caaactcccc ggccagcatc       960
ccacacctga tactggaact tttgaggtgt gaaccagatg agcctcaagt tcaagcgaag      1020
atcatggctt acctccagca agagcagagt aaccgaaaca ggcaagaaaa gctgagcgca      1080
tttgggcttt tatgcaaaat ggcggaccag accctgttct ccattgttga gtgggccagg      1140
agtagtatct tcttcaggga actgagggtt gatgaccaaa tgaagctgct tcaaaactgc      1200
tggagtgagc tcttgattct cgatcacatt taccgacaag tggcgcatgg gaaggaaggg      1260

-continued

```
acaatcttcc tggttactgg agaacacgtg gactactcca ccatcatctc acacacagaa    1320
gtcgcgttca acaacctcct gagtctcgca caggagctgg tggtgaggct ccgttccctt    1380
cagttcgatc agcgggagtt tgtatgtctc aagttcctgg tgctgttcag ctcagatgtg    1440
aagaacctgg agaacctgca gctggtggaa ggtgtccaag agcaggtgaa tgccgccctg    1500
ctggactaca cggtttgcaa ctacccacaa cagactgaga aattcggaca gctacttctt    1560
cggctacccg agatccgggc aatcagcaag caggcagaag actacctgta ctataagcac    1620
gtgaacgggg atgtgcccta taataacctc ctcattgaga tgctgcatgc caaaagagcc    1680
taa                                                                  1683
```

<210> SEQ ID NO 4
<211> LENGTH: 560
<212> TYPE: PRT
<213> ORGANISM: Artificial Sequence
<220> FEATURE:
<223> OTHER INFORMATION: An expression product of a sumoylation mutant of Nr5a2 with five lysine residues mutated

<400> SEQUENCE: 4

```
Met Ser Ala Ser Leu Asp Thr Gly Asp Phe Gln Glu Phe Leu Lys His
 1               5                  10                  15

Gly Leu Thr Ala Ile Ala Ser Ala Pro Gly Ser Glu Thr Arg His Ser
            20                  25                  30

Pro Lys Arg Glu Glu Gln Leu Arg Glu Lys Arg Ala Gly Leu Pro Asp
        35                  40                  45

Arg His Arg Arg Pro Ile Pro Ala Arg Ser Arg Leu Val Met Leu Pro
    50                  55                  60

Lys Val Glu Thr Glu Ala Pro Gly Leu Val Arg Ser His Gly Glu Gln
65                  70                  75                  80

Gly Gln Met Pro Glu Asn Met Gln Val Ser Gln Phe Lys Met Val Asn
                85                  90                  95

Tyr Ser Tyr Asp Glu Asp Leu Glu Glu Leu Cys Pro Val Cys Gly Asp
            100                 105                 110

Lys Val Ser Gly Tyr His Tyr Gly Leu Leu Thr Cys Glu Ser Cys Lys
        115                 120                 125

Gly Phe Phe Lys Arg Thr Val Gln Asn Gln Lys Arg Tyr Thr Cys Ile
    130                 135                 140

Glu Asn Gln Asn Cys Gln Ile Asp Lys Thr Gln Arg Lys Arg Cys Pro
145                 150                 155                 160

Tyr Cys Arg Phe Lys Lys Cys Ile Asp Val Gly Met Arg Leu Glu Ala
                165                 170                 175

Val Arg Ala Asp Arg Met Arg Gly Gly Arg Asn Lys Phe Gly Pro Met
            180                 185                 190

Tyr Lys Arg Asp Arg Ala Leu Lys Gln Gln Lys Lys Ala Leu Ile Arg
        195                 200                 205

Ala Asn Gly Leu Arg Leu Glu Ala Met Ser Gln Val Ile Gln Ala Met
    210                 215                 220

Pro Ser Asp Leu Thr Ser Ala Ile Gln Asn Ile His Ser Ala Ser Lys
225                 230                 235                 240

Gly Leu Pro Leu Ser His Val Ala Leu Pro Pro Thr Asp Tyr Asp Arg
                245                 250                 255

Ser Pro Phe Val Thr Ser Pro Ile Ser Met Thr Met Pro Pro His Ser
            260                 265                 270
```

```
Ser Leu His Gly Tyr Gln Pro Tyr Gly His Phe Pro Ser Arg Ala Ile
        275                 280                 285
Arg Ser Glu Tyr Pro Asp Pro Tyr Ser Ser Pro Glu Ser Met Met
    290                 295                 300
Gly Tyr Ser Tyr Met Asp Gly Tyr Gln Thr Asn Ser Pro Ala Ser Ile
305                 310                 315                 320
Pro His Leu Ile Leu Glu Leu Arg Cys Glu Pro Asp Glu Pro Gln
                325                 330                 335
Val Gln Ala Lys Ile Met Ala Tyr Leu Gln Glu Gln Ser Asn Arg
            340                 345                 350
Asn Arg Gln Glu Lys Leu Ser Ala Phe Gly Leu Leu Cys Lys Met Ala
        355                 360                 365
Asp Gln Thr Leu Phe Ser Ile Val Glu Trp Ala Arg Ser Ser Ile Phe
    370                 375                 380
Phe Arg Glu Leu Arg Val Asp Asp Gln Met Lys Leu Leu Gln Asn Cys
385                 390                 395                 400
Trp Ser Glu Leu Leu Ile Leu Asp His Ile Tyr Arg Gln Val Ala His
                405                 410                 415
Gly Lys Glu Gly Thr Ile Phe Leu Val Thr Gly Glu His Val Asp Tyr
            420                 425                 430
Ser Thr Ile Ile Ser His Thr Glu Val Ala Phe Asn Asn Leu Leu Ser
        435                 440                 445
Leu Ala Gln Glu Leu Val Val Arg Leu Arg Ser Leu Gln Phe Asp Gln
    450                 455                 460
Arg Glu Phe Val Cys Leu Lys Phe Leu Val Leu Phe Ser Ser Asp Val
465                 470                 475                 480
Lys Asn Leu Glu Asn Leu Gln Leu Val Glu Gly Val Gln Glu Gln Val
                485                 490                 495
Asn Ala Ala Leu Leu Asp Tyr Thr Val Cys Asn Tyr Pro Gln Gln Thr
            500                 505                 510
Glu Lys Phe Gly Gln Leu Leu Leu Arg Leu Pro Glu Ile Arg Ala Ile
        515                 520                 525
Ser Lys Gln Ala Glu Asp Tyr Leu Tyr Tyr Lys His Val Asn Gly Asp
    530                 535                 540
Val Pro Tyr Asn Asn Leu Leu Ile Glu Met Leu His Ala Lys Arg Ala
545                 550                 555                 560

<210> SEQ ID NO 5
<211> LENGTH: 2762
<212> TYPE: DNA
<213> ORGANISM: Mus musculus

<400> SEQUENCE: 5
gctgtaagcc aaaggactgc caataatttc gctaagaatg tctgctagtt tggatactgg      60
agattttcaa gaatttctta agcatggact tacagctatt gcgtctgcac cagggtcaga     120
gactcgccac tcccccaaac gtgaggaaca actccgggaa aaacgtgctg ggcttccgga     180
ccgacaccga cgccccattc ccgcccgcag ccgccttgtc atgctgccca agtggagac      240 ggaagcccca ggactggtcc gatcgcatgg ggaacagggg cagatgccag aaaacatgca     300
agtgtctcaa tttaaaatgg tgaattactc ctatgatgaa gatctggaag agctatgtcc     360
tgtgtgtggc gataaagtgt ctgggtacca ttacggtctc ctcacgtgcg aaagctgcaa     420
gggttttttt aagcgaactg tccaaaacca aaaaaggtac acgtgcatag agaaccagaa     480
ttgccaaatt gacaaaacgc agagaaaacg atgtccctac tgtcgattca aaaatgtat      540
```

```
cgatgttggg atgaagctgg aagccgtaag agccgaccgc atgcgagggg gcagaaataa    600
gtttgggcca atgtacaaga gagacagggc tttgaagcag cagaagaaag ccctcattcg    660
agccaatgga cttaagctgg aagccatgtc tcaggtgatc caagcaatgc cctcagacct    720
gacctctgca attcagaaca ttcattccgc ctccaaaggc ctacctctga gccatgtagc    780
cttgcctccg acagactatg acagaagtcc ctttgtcaca tctcccatta gcatgacaat    840
gccacctcac agcagcctgc atggttacca accctatggt cactttccta gtcgggccat    900
caagtctgag tacccagacc cctactccag ctcacctgag tcaatgatgg gttactccta    960
catggatggt taccagacaa actccccggc cagcatccca cacctgatac tggaactttt   1020
gaagtgtgaa ccagatgagc ctcaagttca agcgaagatc atggcttacc tccagcaaga   1080
gcagagtaac cgaaacaggc aagaaaagct gagcgcattt gggcttttat gcaaaatggc   1140
ggaccagacc ctgttctcca ttgttgagtg ggccaggagt agtatcttct tcagggaact   1200
gaaggttgat gaccaaatga agctgcttca aaactgctgg agtgagctct tgattctcga   1260
tcacatttac cgacaagtgg cgcatgggaa ggaagggaca atcttcctgg ttactggaga   1320
acacgtggac tactccacca tcatctcaca cacagaagtc gcgttcaaca acctcctgag   1380
tctcgcacag gagctggtgg tgaggctccg ttcccttcag ttcgatcagc gggagtttgt   1440
atgtctcaag ttcctggtgc tgttcagctc agatgtgaag aacctggaga acctgcagct   1500
ggtggaaggt gtccaagagc aggtgaatgc cgccctgctg gactacacgg tttgcaacta   1560
cccacaacag actgagaaat tcggacagct acttcttcgg ctacccgaga tccgggcaat   1620
cagcaagcag gcagaagact acctgtacta taagcacgtg aacggggatg tgccctataa   1680
taacctcctc attgagatgc tgcatgccaa aagagcctaa gtccccaccc ctggaagctt   1740
gctctaggaa cacagactgg aaggagaaga ggaggacgat gacagaaaca caatactctg   1800
aactgctcca agcaatgcta attataaact tggtttaaag cactgaattt ttaaaagcat   1860
aataattaaa tacctaatag caaataaatg atatatcagg gtatttgtac tgcaaactgt   1920
gaatcaaagg ctgtatgaat caaaggattc atatgaaaga cattgtaatg gggtggattg   1980
aacttacaga tggagaccaa taccacagca gaataaaaat ggacagaaca atccttgtat   2040
atttaaacta atctgctatt aagaaattca gaagttgatc tctgttatta attggatttg   2100
tcctgaatta ctccgtggtg acgctgaaca actcaagaat acatgggctg tgccttggca   2160 gccctcccc atccctccca ccaccaccac ccccacccc acaaggccct ataccttctg   2220
acctgtgagc cctgaagcta ttttaaggac ttctgttcag ccatacccag tagtagctcc   2280
actaaaccat gatttctgga tgtctgtgtc ttagacctgc caacagctaa taagaacaat   2340
gtataaatat gtcagcttgc atttaaata tgtgctgaag tttgttttgt cgtgtgttcg   2400
taattaaaaa gaaaacgggc agtaaccctc ttctatataa gcattagtta atattaaggg   2460
aaatcaaaca aatctaagcc aatactccca acaagcaagt tagatcttac ttctgctgct   2520
gttgctgaaa tgtggctttg gcatggttgg gtttcataaa acttttttggc caagaggctt   2580 gttagtatac atccatctgt ttagtcatca aggtttgtag ttcacttaaa aaaaaataaa   2640
ccactagaca tctttttgctg aatgtcaaat agtcacagtc taagtagcca aaaagtcaaa   2700
gcgtgttaaa cattgccaaa tgaaggaaag ggtgagctgc aaagggggatg gttcgaggtt   2760 ca                                                                  2762
```

<210> SEQ ID NO 6
<211> LENGTH: 560
<212> TYPE: PRT
<213> ORGANISM: Mus musculus

<400> SEQUENCE: 6

| | | | | | | | | | | | | | | |
|---|---|---|---|---|---|---|---|---|---|---|---|---|---|---|
| Met | Ser | Ala | Ser | Leu | Asp | Thr | Gly | Asp | Phe | Gln | Glu | Phe | Leu | Lys | His |
| 1 | | | | 5 | | | | | 10 | | | | | 15 | |
| Gly | Leu | Thr | Ala | Ile | Ala | Ser | Ala | Pro | Gly | Ser | Glu | Thr | Arg | His | Ser |
| | | | 20 | | | | | 25 | | | | | 30 | | |
| Pro | Lys | Arg | Glu | Glu | Gln | Leu | Arg | Glu | Lys | Arg | Ala | Gly | Leu | Pro | Asp |
| | | 35 | | | | | 40 | | | | | 45 | | | |
| Arg | His | Arg | Arg | Pro | Ile | Pro | Ala | Arg | Ser | Arg | Leu | Val | Met | Leu | Pro |
| | 50 | | | | | 55 | | | | | 60 | | | | |
| Lys | Val | Glu | Thr | Glu | Ala | Pro | Gly | Leu | Val | Arg | Ser | His | Gly | Glu | Gln |
| 65 | | | | | 70 | | | | | 75 | | | | | 80 |
| Gly | Gln | Met | Pro | Glu | Asn | Met | Gln | Val | Ser | Gln | Phe | Lys | Met | Val | Asn |
| | | | | 85 | | | | | 90 | | | | | 95 | |
| Tyr | Ser | Tyr | Asp | Glu | Asp | Leu | Glu | Glu | Leu | Cys | Pro | Val | Cys | Gly | Asp |
| | | | 100 | | | | | 105 | | | | | 110 | | |
| Lys | Val | Ser | Gly | Tyr | His | Tyr | Gly | Leu | Leu | Thr | Cys | Glu | Ser | Cys | Lys |
| | | | 115 | | | | | 120 | | | | | 125 | | |
| Gly | Phe | Phe | Lys | Arg | Thr | Val | Gln | Asn | Gln | Lys | Arg | Tyr | Thr | Cys | Ile |
| | | 130 | | | | | 135 | | | | | 140 | | | |
| Glu | Asn | Gln | Asn | Cys | Gln | Ile | Asp | Lys | Thr | Gln | Arg | Lys | Arg | Cys | Pro |
| 145 | | | | | 150 | | | | | 155 | | | | | 160 |
| Tyr | Cys | Arg | Phe | Lys | Lys | Cys | Ile | Asp | Val | Gly | Met | Lys | Leu | Glu | Ala |
| | | | | 165 | | | | | 170 | | | | | 175 | |
| Val | Arg | Ala | Asp | Arg | Met | Arg | Gly | Gly | Arg | Asn | Lys | Phe | Gly | Pro | Met |
| | | | 180 | | | | | 185 | | | | | 190 | | |
| Tyr | Lys | Arg | Asp | Arg | Ala | Leu | Lys | Gln | Gln | Lys | Lys | Ala | Leu | Ile | Arg |
| | | | 195 | | | | | 200 | | | | | 205 | | |
| Ala | Asn | Gly | Leu | Lys | Leu | Glu | Ala | Met | Ser | Gln | Val | Ile | Gln | Ala | Met |
| | 210 | | | | | 215 | | | | | 220 | | | | |
| Pro | Ser | Asp | Leu | Thr | Ser | Ala | Ile | Gln | Asn | Ile | His | Ser | Ala | Ser | Lys |
| 225 | | | | | 230 | | | | | 235 | | | | | 240 |
| Gly | Leu | Pro | Leu | Ser | His | Val | Ala | Leu | Pro | Pro | Thr | Asp | Tyr | Asp | Arg |
| | | | | 245 | | | | | 250 | | | | | 255 | |
| Ser | Pro | Phe | Val | Thr | Ser | Pro | Ile | Ser | Met | Thr | Met | Pro | Pro | His | Ser |
| | | | 260 | | | | | 265 | | | | | 270 | | |
| Ser | Leu | His | Gly | Tyr | Gln | Pro | Tyr | Gly | His | Phe | Pro | Ser | Arg | Ala | Ile |
| | | | 275 | | | | | 280 | | | | | 285 | | |
| Lys | Ser | Glu | Tyr | Pro | Asp | Pro | Tyr | Ser | Ser | Ser | Pro | Glu | Ser | Met | Met |
| | | 290 | | | | | 295 | | | | | 300 | | | |
| Gly | Tyr | Ser | Tyr | Met | Asp | Gly | Tyr | Gln | Thr | Asn | Ser | Pro | Ala | Ser | Ile |
| 305 | | | | | 310 | | | | | 315 | | | | | 320 |
| Pro | His | Leu | Ile | Leu | Glu | Leu | Leu | Lys | Cys | Glu | Pro | Asp | Glu | Pro | Gln |
| | | | | 325 | | | | | 330 | | | | | 335 | |
| Val | Gln | Ala | Lys | Ile | Met | Ala | Tyr | Leu | Gln | Gln | Glu | Gln | Ser | Asn | Arg |
| | | | 340 | | | | | 345 | | | | | 350 | | |
| Asn | Arg | Gln | Glu | Lys | Leu | Ser | Ala | Phe | Gly | Leu | Leu | Cys | Lys | Met | Ala |
| | | 355 | | | | | 360 | | | | | 365 | | | |
| Asp | Gln | Thr | Leu | Phe | Ser | Ile | Val | Glu | Trp | Ala | Arg | Ser | Ser | Ile | Phe |
| | 370 | | | | | 375 | | | | | 380 | | | | |

-continued

```
Phe Arg Glu Leu Lys Val Asp Asp Gln Met Lys Leu Leu Gln Asn Cys
385                 390                 395                 400

Trp Ser Glu Leu Leu Ile Leu Asp His Ile Tyr Arg Gln Val Ala His
            405                 410                 415

Gly Lys Glu Gly Thr Ile Phe Leu Val Thr Gly Glu His Val Asp Tyr
        420                 425                 430

Ser Thr Ile Ile Ser His Thr Glu Val Ala Phe Asn Asn Leu Leu Ser
        435                 440                 445

Leu Ala Gln Glu Leu Val Val Arg Leu Arg Ser Leu Gln Phe Asp Gln
    450                 455                 460

Arg Glu Phe Val Cys Leu Lys Phe Leu Val Leu Phe Ser Ser Asp Val
465                 470                 475                 480

Lys Asn Leu Glu Asn Leu Gln Leu Val Glu Gly Val Gln Glu Gln Val
                485                 490                 495

Asn Ala Ala Leu Leu Asp Tyr Thr Val Cys Asn Tyr Pro Gln Gln Thr
            500                 505                 510

Glu Lys Phe Gly Gln Leu Leu Leu Arg Leu Pro Glu Ile Arg Ala Ile
        515                 520                 525

Ser Lys Gln Ala Glu Asp Tyr Leu Tyr Tyr Lys His Val Asn Gly Asp
    530                 535                 540

Val Pro Tyr Asn Asn Leu Leu Ile Glu Met Leu His Ala Lys Arg Ala
545                 550                 555                 560
```

<210> SEQ ID NO 7
<211> LENGTH: 2947
<212> TYPE: DNA
<213> ORGANISM: Mus musculus

<400> SEQUENCE: 7

| | | |
|---|---|---|
| gagggagga ggaaaggacg atcggacagg gccagtttcc agtccgccgc tgcccgcccg | 60 |
| ctgctgggtg aagaagtttc tgagagcccg ctagccactg ccctacctga ggcctgggag | 120 |
| cctccccacc aggaccctgg tgtccagtgt ccacccttat ccggctgaga attctccttc | 180 |
| cgttcagcgg acgccgcggg catggactat tcgtacgacg aggacctgga cgagctgtgt | 240 |
| ccagtgtgtg gtgacaaggt gtcgggctac cactacgggc tgctcacgtg cgagagctgc | 300 |
| aagggcttct tcaagcgcac agtccagaac aacaagcatt acacgtgcac cgagagtcag | 360 |
| agctgcaaaa tcgacaagac gcagcgtaag cgctgtccct tctgccgctt ccagaagtgc | 420 |
| ctgacggtgg gcatgcgcct ggaagctgtg cgtgctgatc gaatgcgggg tggccggaac | 480 |
| aagtttgggc ccatgtacaa gagagaccgg gccttgaagc agcagaagaa agcacagatt | 540 |
| cgggccaatg gcttcaagct ggagaccgga ccaccgatgg gggtgccccc gccacccccct | 600 |
| cccccaccgg actacatgtt accccctagc ctgcacgcac cggagcccaa ggccctggtc | 660 |
| tctggcccac ccagtgggcc gctggtgac tttggagccc catctctacc catggctgtg | 720 |
| cctggtcccc acggacctct ggctggctac ctctatcctg ccttctctaa ccgcaccatc | 780 |
| aagtctgagt atccagagcc ctatgccagc cccccacaac agccagggcc accctacagc | 840 |
| tatccagagc ccttctcagg agggcccaat gtaccagagc tcatattgca gctgctgcaa | 900 |
| ctagagccag aggaggacca ggtgcgcgct cgcatcgtgg gctgtctgca ggagccagcc | 960 |
| aaaagccgct ctgaccagcc agcgcccttc agcctcctct gcagaatggc cgaccagacc | 1020 |
| tttatctcca ttgtcgactg gcacgaagg tgcatggtct ttaaggagct ggaggtggct | 1080 |
| gaccagatga cactgctgca gaactgttgg agcgagctgc tggtgttgga ccacatctac | 1140 |

```
cgccaggtcc agtacggcaa ggaagacagc atcctgctgg ttactggaca ggaggtggag    1200
ctgagcacag tggctgtgca ggctggctcc ctgctgcaca gcctggtgct gcgggcccaa    1260
gagttagtgc tccagttgca tgcactgcag ctggaccgcc aggagttcgt ctgtctcaag    1320
ttcctcatcc tcttcagcct cgatgtgaaa ttcctgaaca ccacagcct cgtaaaggac     1380 gcccaggaaa aggccaacgc tgccctgttg gattacacct tgtgtcacta cccacactgc    1440
ggggacaaat ccagcagtt gctattgtgc ctggtggagg tgcgggccct gagcatgcag     1500
gccaaggagt acctgtacca aagcatttg gcaacgaga tgccccgcaa caaccttctc      1560
attgagatgc tgcaggccaa gcagacttga gcctgggtgc caggcagcgg gcaataggca    1620
gggatgccac tgcctccaaa agactccttg cattaggtga tccaggagcc ctgtcactaa    1680
gcccctgccc ctgagctcca gagctgtgtg tttgggcaag gatgggcggg gattggccgg    1740
ggcaggttgc ctttactagc cattggcctg tgtccgccac ttggagtgcc ccaaaggggg    1800
cttctaacca ttccttcctc catcagcccc cagctttttt tcctggtatc tgaggtccca    1860
ggaggaggct caggattccc tggtgggtct ggatgtccct tgggtcagag gtcatccttt    1920
ccctctctcc tgttatcaga ggcaaaggaa ggtctacagg catcaatgag ggcaaaggag    1980
ggggtctcca gactccactg aagcaggaag tccactgttg taaactgagt ttgctaaatt    2040
gggtccccag aggataccat gagagtgggt agggcaaaaa gagcccttc cgccctctac     2100 ccatctaatt ctgatcctct acctgtagga ggactttggt gtgatcatcc ttctcccagg    2160
gcccggctac ccagggagga ggagtctggt gtagccaaca ttcctgccct aaccctgccc    2220
atcaccagct ggctgggctg gtatttatct gcaaggttga agtcactggg attcttttcc    2280
tttcacctag atagtccttg gaaagtgtgt gagagagaag tgggcaggag acagactggg    2340
gactgagctg ggatatgggg actagcatca aagctttctc ctgacatctc tttccaagag    2400
tcggggtggc atctgtaccc cacctcaccc ccgagaagtg ctattgcttg ccctctgcct    2460
cagccccact aggggaacaa caggaggcct gctgggggctt agagtccgtg caggtgggga   2520
tatgggtaaa tctaggagaa ctcacagatc tttatatgag acagtgctg aggactttct     2580 catggctcca tcctttggt ccctcgccac tacccttgaa gctggcttca gttccctggc     2640
tgctgctttg cctcctgaaa gccactctgt aggaccaagc actcggggga gaggcctaag    2700
ccatcctctg ttccagactg gacatccact gtctttcctg ctttcgcgtc agatttacag    2760
cttatgctag gccacccaa ctggacaagg ctgtctcctg tcttctacta ccctggctca     2820
gcccccacct ctgcccctga aatgcgtgct cccaccaagg ccagagaccc acagcccaa     2880 gacaagaagt gcccttataa accctgcag ccctgcagcc ctgaaataaa ttttgcaatt     2940
agtttcc                                                             2947
```

<210> SEQ ID NO 8
<211> LENGTH: 462
<212> TYPE: PRT
<213> ORGANISM: Mus musculus

<400> SEQUENCE: 8

Met Asp Tyr Ser Tyr Asp Glu Asp Leu Asp Glu Leu Cys Pro Val Cys
1               5                   10                  15

Gly Asp Lys Val Ser Gly Tyr His Tyr Gly Leu Leu Thr Cys Glu Ser
                20                  25                  30

Cys Lys Gly Phe Phe Lys Arg Thr Val Gln Asn Asn Lys His Tyr Thr
        35                  40                  45

```
Cys Thr Glu Ser Gln Ser Cys Lys Ile Asp Lys Thr Gln Arg Lys Arg
 50                  55                  60

Cys Pro Phe Cys Arg Phe Gln Lys Cys Leu Thr Val Gly Met Arg Leu
 65                  70                  75                  80

Glu Ala Val Arg Ala Asp Arg Met Arg Gly Gly Arg Asn Lys Phe Gly
                 85                  90                  95

Pro Met Tyr Lys Arg Asp Arg Ala Leu Lys Gln Gln Lys Lys Ala Gln
            100                 105                 110

Ile Arg Ala Asn Gly Phe Lys Leu Glu Thr Gly Pro Pro Met Gly Val
            115                 120                 125

Pro Pro Pro Pro Pro Pro Pro Asp Tyr Met Leu Pro Pro Ser Leu
130                 135                 140

His Ala Pro Glu Pro Lys Ala Leu Val Ser Gly Pro Ser Gly Pro
145                 150                 155                 160

Leu Gly Asp Phe Gly Ala Pro Ser Leu Pro Met Ala Val Pro Gly Pro
                165                 170                 175

His Gly Pro Leu Ala Gly Tyr Leu Tyr Pro Ala Phe Ser Asn Arg Thr
            180                 185                 190

Ile Lys Ser Glu Tyr Pro Glu Pro Tyr Ala Ser Pro Pro Gln Gln Pro
            195                 200                 205

Gly Pro Pro Tyr Ser Tyr Pro Glu Pro Phe Ser Gly Gly Pro Asn Val
210                 215                 220

Pro Glu Leu Ile Leu Gln Leu Leu Gln Leu Glu Pro Glu Glu Asp Gln
225                 230                 235                 240

Val Arg Ala Arg Ile Val Gly Cys Leu Gln Glu Pro Ala Lys Ser Arg
                245                 250                 255

Ser Asp Gln Pro Ala Pro Phe Ser Leu Leu Cys Arg Met Ala Asp Gln
            260                 265                 270

Thr Phe Ile Ser Ile Val Asp Trp Ala Arg Arg Cys Met Val Phe Lys
            275                 280                 285

Glu Leu Glu Val Ala Asp Gln Met Thr Leu Leu Gln Asn Cys Trp Ser
290                 295                 300

Glu Leu Leu Val Leu Asp His Ile Tyr Arg Gln Val Gln Tyr Gly Lys
305                 310                 315                 320

Glu Asp Ser Ile Leu Leu Val Thr Gly Gln Glu Val Glu Leu Ser Thr
                325                 330                 335

Val Ala Val Gln Ala Gly Ser Leu Leu His Ser Leu Val Leu Arg Ala
            340                 345                 350

Gln Glu Leu Val Leu Gln Leu His Ala Leu Gln Leu Asp Arg Gln Glu
            355                 360                 365

Phe Val Cys Leu Lys Phe Leu Ile Leu Phe Ser Leu Asp Val Lys Phe
370                 375                 380

Leu Asn Asn His Ser Leu Val Lys Asp Ala Gln Glu Lys Ala Asn Ala
385                 390                 395                 400

Ala Leu Leu Asp Tyr Thr Leu Cys His Tyr Pro His Cys Gly Asp Lys
                405                 410                 415

Phe Gln Gln Leu Leu Leu Cys Leu Val Glu Val Arg Ala Leu Ser Met
            420                 425                 430

Gln Ala Lys Glu Tyr Leu Tyr His Lys His Leu Gly Asn Glu Met Pro
            435                 440                 445

Arg Asn Asn Leu Leu Ile Glu Met Leu Gln Ala Lys Gln Thr
450                 455                 460
```

```
<210> SEQ ID NO 9
<211> LENGTH: 88
<212> TYPE: PRT
<213> ORGANISM: Artificial Sequence
<220> FEATURE:
<223> OTHER INFORMATION: From Nuclear receptor subfamily 5 sequences

<400> SEQUENCE: 9

Asp Glu Asp Leu Glu Leu Cys Pro Val Cys Gly Asp Lys Val Ser
1               5                   10                  15

Gly Tyr His Tyr Gly Leu Leu Thr Cys Glu Ser Cys Lys Gly Phe Phe
            20                  25                  30

Lys Arg Thr Val Gln Asn Gln Lys Arg Tyr Thr Cys Ile Glu Asn Gln
        35                  40                  45

Asn Cys Gln Ile Asp Lys Thr Gln Arg Lys Arg Cys Pro Tyr Cys Arg
50                  55                  60

Phe Lys Lys Cys Ile Asp Val Gly Met Lys Leu Glu Ala Val Arg Ala
65                  70                  75                  80

Asp Arg Met Arg Gly Gly Arg Asn
            85

<210> SEQ ID NO 10
<211> LENGTH: 244
<212> TYPE: PRT
<213> ORGANISM: Artificial Sequence
<220> FEATURE:
<223> OTHER INFORMATION: from Nuclear receptor subfamily 5 proteins

<400> SEQUENCE: 10

Pro Ala Ser Ile Pro His Leu Ile Leu Glu Leu Leu Lys Cys Glu Pro
1               5                   10                  15

Asp Glu Pro Gln Val Gln Ala Lys Ile Met Ala Tyr Leu Gln Gln Glu
            20                  25                  30

Gln Ser Asn Arg Asn Arg Gln Glu Lys Leu Ser Ala Phe Gly Leu Leu
        35                  40                  45

Cys Lys Met Ala Asp Gln Thr Leu Phe Ser Ile Val Glu Trp Ala Arg
50                  55                  60

Ser Ser Ile Phe Phe Arg Glu Leu Lys Val Asp Asp Gln Met Lys Leu
65                  70                  75                  80

Leu Gln Asn Cys Trp Ser Glu Leu Leu Ile Leu Asp His Ile Tyr Arg
            85                  90                  95

Gln Val Ala His Gly Lys Glu Gly Thr Ile Phe Leu Val Thr Gly Glu
        100                 105                 110

His Val Asp Tyr Ser Thr Ile Ile Ser His Thr Glu Val Ala Phe Asn
    115                 120                 125

Asn Leu Leu Ser Leu Ala Gln Glu Leu Val Val Arg Leu Arg Ser Leu
    130                 135                 140

Gln Phe Asp Gln Arg Glu Phe Val Cys Leu Lys Phe Leu Val Leu Phe
145                 150                 155                 160

Ser Ser Asp Val Lys Asn Leu Glu Asn Leu Gln Leu Val Glu Gly Val
            165                 170                 175

Gln Glu Gln Val Asn Ala Ala Leu Leu Asp Tyr Thr Val Cys Asn Tyr
        180                 185                 190

Pro Gln Gln Thr Glu Lys Phe Gly Gln Leu Leu Leu Arg Leu Pro Glu
    195                 200                 205

Ile Arg Ala Ile Ser Lys Gln Ala Glu Asp Tyr Leu Tyr Tyr Lys His
    210                 215                 220
```

Val Asn Gly Asp Val Pro Tyr Asn Asn Leu Leu Ile Glu Met Leu His
225                 230                 235                 240

Ala Lys Arg Ala

<210> SEQ ID NO 11
<211> LENGTH: 26
<212> TYPE: DNA
<213> ORGANISM: Artificial Sequence
<220> FEATURE:
<223> OTHER INFORMATION: Primer sequence used in PCR amplification of
      Pou5f1 promoter region

<400> SEQUENCE: 11
atgggttgaa atattgggtt tattta                                    26

<210> SEQ ID NO 12
<211> LENGTH: 25
<212> TYPE: DNA
<213> ORGANISM: Artificial Sequence
<220> FEATURE:
<223> OTHER INFORMATION: Primer sequence used in PCR amplification of
      Pou5f1 promoter region

<400> SEQUENCE: 12
ccaccctcta accttaacct ctaac                                     25

<210> SEQ ID NO 13
<211> LENGTH: 30
<212> TYPE: DNA
<213> ORGANISM: Artificial Sequence
<220> FEATURE:
<223> OTHER INFORMATION: Primer sequence used in PCR amplification of
      Nanog promoter region

<400> SEQUENCE: 13
gattttgtag gtgggattaa ttgtgaattt                                30

<210> SEQ ID NO 14
<211> LENGTH: 30
<212> TYPE: DNA
<213> ORGANISM: Artificial Sequence
<220> FEATURE:
<223> OTHER INFORMATION: Primer sequence used in PCR amplification of
      Nanog promoter region

<400> SEQUENCE: 14
accaaaaaaa cccacactca tatcaatata                                30

<210> SEQ ID NO 15
<211> LENGTH: 24
<212> TYPE: DNA
<213> ORGANISM: Artificial Sequence
<220> FEATURE:
<223> OTHER INFORMATION: Sense primer sequence

<400> SEQUENCE: 15
gacggcatcg cagcttggat acac                                      24

<210> SEQ ID NO 16
<211> LENGTH: 23
<212> TYPE: DNA
<213> ORGANISM: Artificial Sequence
<220> FEATURE:
<223> OTHER INFORMATION: Antisense primer sequence Nr5a2

```
<400> SEQUENCE: 16
gacgcaatag ctgtaagtcc atg                                              23

<210> SEQ ID NO 17
<211> LENGTH: 25
<212> TYPE: DNA
<213> ORGANISM: Artificial Sequence
<220> FEATURE:
<223> OTHER INFORMATION: Antisense primer sequence Sox2

<400> SEQUENCE: 17
gcttcagctc cgtctccatc atgtt                                            25

<210> SEQ ID NO 18
<211> LENGTH: 20
<212> TYPE: DNA
<213> ORGANISM: Artificial Sequence
<220> FEATURE:
<223> OTHER INFORMATION: Antisense primer sequence Klf4

<400> SEQUENCE: 18
gccatgtcag actcgccagg                                                  20

<210> SEQ ID NO 19
<211> LENGTH: 23
<212> TYPE: DNA
<213> ORGANISM: Artificial Sequence
<220> FEATURE:
<223> OTHER INFORMATION: Antisense primer sequence c-Myc

<400> SEQUENCE: 19
tcgtcgcaga tgaaataggg ctg                                              23

<210> SEQ ID NO 20
<211> LENGTH: 25
<212> TYPE: DNA
<213> ORGANISM: Artificial Sequence
<220> FEATURE:
<223> OTHER INFORMATION: Antisense primer sequence Oct4

<400> SEQUENCE: 20
ccaatacctc tgagcctggt ccgat                                            25

<210> SEQ ID NO 21
<211> LENGTH: 19
<212> TYPE: DNA
<213> ORGANISM: Artificial Sequence
<220> FEATURE:
<223> OTHER INFORMATION: shRNA sequence Pou5f1

<400> SEQUENCE: 21
gaaggatgtg gttcgagta                                                   19

<210> SEQ ID NO 22
<211> LENGTH: 19
<212> TYPE: DNA
<213> ORGANISM: Artificial Sequence
<220> FEATURE:
<223> OTHER INFORMATION: shRNA sequence luciferase

<400> SEQUENCE: 22
gatgaaatgg gtaagtaca                                                   19
```

```
<210> SEQ ID NO 23
<211> LENGTH: 19
<212> TYPE: DNA
<213> ORGANISM: Artificial Sequence
<220> FEATURE:
<223> OTHER INFORMATION: shRNA sequence Nr5a2

<400> SEQUENCE: 23
gcaagtgtct caatttaaa                                                 19

<210> SEQ ID NO 24
<211> LENGTH: 25
<212> TYPE: DNA
<213> ORGANISM: Artificial Sequence
<220> FEATURE:
<223> OTHER INFORMATION: Antisense primer sequence Pou5f1

<400> SEQUENCE: 24
ccaatacctc tgagcctggt ccgat                                          25
```

NUCLEAR RECEPTOR AND MUTANT THEREOF AND THE USE OF THE SAME IN THE REPROGRAMMING OF CELLS

CROSS-REFERENCE TO RELATED APPLICATION

This application is a U.S. National Stage application based on International Application No. PCT/SG2010/000372, filed on Sep. 30, 2010, which claims benefit of, and priority from, Singapore patent application Numbers 200906546-7, filed on 30 Sep. 2009 and 201000140-2, filed on 9 Jan. 2010 the contents of both of which are incorporated herein by reference.

FIELD OF THE INVENTION

The present invention relates to a nuclear receptor protein and the use of such proteins in methods of reprogramming a differentiated cell to a pluripotent state.

BACKGROUND ART

Stem cell treatments are a type of cell therapy that introduces new cells into damaged tissue in order to treat a disease or injury. The ability of pluripotent cells to self-renew and differentiate into a range of different cell types offers a large potential to culture tissues that can replace diseased and damaged tissues in the body, without the risk of rejection.

A number of stem cell treatments exist, although most are still experimental and/or costly, with the notable exception of bone marrow transplantation. Medical researchers anticipate one day being able to use cells derived from adult somatic cells to treat cancer, diabetes, neurological disorders such as Parkinson's disease, Huntington's disease, Alzheimer's, dementia, as well as cardiac failure and muscle damage, along with many others.

The reversion of somatic cells to pluripotent cells is commonly referred to as reprogramming. Somatic cell nuclear transfer and cell fusion are examples of techniques employed in the reprogramming of differentiated cells (Lewitzky, M. & Yamanaka, S. (2007) Curr Opin Biotechnol 18, 467-73). Another method of reprogramming was discovered when mouse fibroblasts were reprogrammed with the retroviral introduction of just four transcription factors Oct4, Sox2, Klf4 and c-Myc (Takahashi, K. & Yamanaka, S. (2006) Cell 126, 663-76). Somatic cells can be reprogrammed back to the pluripotent state by the combined introduction of transcription factors such as Oct4, Sox2, Klf4 and c-Myc (OSKM). These converted cells share many characteristics with embryonic stem cells (ESCs) in terms of morphology, genetic expression and epigenetic marks and are known as induced pluripotent stem cells (iPSCs). Since the discovery of iPSCs, cells from different lineages and a diverse range of species have been successfully reprogrammed (Feng, B., et al. (2009) Cell Stem Cell 4, 301-12). There is a need to enhance the efficiency of such methods.

Besides the four reprogramming factors discovered by the groundbreaking study of Yamanaka, other factors such as NANOG and LIN28 were also found to participate in reprogramming (Yu, J. et al. (2007) Science 318, 1917-20). In addition, UTF1, an ESC-specific transcription factor, was shown to enhance the reprogramming of human fibroblasts in conjunction with the four Yamanaka factors as well as the knockdown of p53. Some of the four Yamanaka transcription factors have also been shown to replace factors in reprogramming. For instance, Klf4 can be replaced by Klf2 and Klf5, Sox2 can be substituted by Sox1 and Sox5 while N-myc and L-myc could replace c-Myc. Amongst the four defined reprogramming factors, Oct4 has been shown to be the most critical in inducing pluripotency (Nakagawa, M. et al. (2008) Nat Biotechnol 26, 101-6). However, Oct4 remains irreplaceable by other transcription factors including its close family members such as Oct1 and Oct6 (Nakagawa, M. et al. (2008). No transcription factor has been hitherto shown to be able to substitute Oct4 in the reprogramming of somatic cells.

Oct-4 (an abbreviation of Octamer-4) is a homeodomain transcription factor protein of the POU family. Oct-4 expression must be closely regulated; too much or too little will actually cause differentiation of the cell. Oct-4 has been implicated in tumorigenesis of adult germ cells. Ectopic expression of the factor in adult mice has been found to cause the formation of dysplastic lesions of the skin and intestine. The intestinal dysplasia resulted from an increase in progenitor cell population and the upregulation of β-catenin transcription through the inhibition of cellular differentiation.

Oct4, expressed in the inner cell mass (ICM) of the blastocysts, is critical in maintaining pluripotency of cells in the ICM as well as ESCs. Although neural progenitor cells (NPCs) express a high level of endogenous Sox2, ectopic expression of Oct4 alone was still required for their reprogramming. This observation suggests that Oct4 is pivotal in imparting pluripotency in somatic cells. In addition, only a few transcription factors such as Oct4 and the aforementioned transcriptional factors have been reported to contribute to iPSC generation.

Nuclear receptors have the ability to directly bind to DNA and regulate the expression of adjacent genes. Nuclear receptors are modular in structure and contain specific domains such as DNA binding domain (DBD) and Ligand binding domain (LBD). They are generally classified into two broad classes according to their mechanism of action and subcellular distribution in the absence of ligand. The 48 known human nuclear receptors have been further categorized into subfamilies based on the sequence homology of the proteins. Subfamily 5 includes two nuclear receptors, Nr5a1, also known as steroidogenic factor 1 (Sf1), and Nr5a2. Similar to other nuclear receptors, Nr5a2 possesses a ligand binding domain (LBD) and a DNA binding domain (DBD). However, being an orphan nuclear receptor, the endogenous ligands of Nr5a2 remains unknown. Unlike most nuclear receptors which function as dimers, Nr5a2 is able to bind DNA in its monomeric state (Galarneau, L. et al. (1996) Mol Cell Biol 16, 3853-65).

SUMMARY OF THE INVENTION

The present invention seeks to provide alternative transcription factors and the use of such factors in methods of reprogramming a differentiated cell to a pluripotent state.

We show that nuclear receptors and sumoylation mutants of nuclear receptors are able to initiate pluripotent stem cells in vitro. Further nuclear receptors may be able to replace Oct4 in the derivation of pluripotent stem cells in vitro.

Accordingly one aspect of the present invention provides a method for inducing pluripotent stem cells in vitro comprising the steps of: culturing cells in vitro; introducing a polynucleotide that encodes a transcription factor into the cell in the culture, wherein the polynucleotide encoding a transcription factor comprises a nuclear receptor and one or more transcription factor selected from a Sox gene, Krüppel-like factor gene, or an myc family of genes to induce the cell to be a pluripotent cell.

Another aspect of the invention provides an expression vector comprising a polynucleotide of a nuclear receptor from subfamily 5 selected from: (a) polynucleotides comprising the nucleotide sequence set out in SEQ ID NO: 1, SEQ ID NO: 3, SEQ ID NO: 5 or SEQ ID NO: 7 or a fragment expressing polypeptide SEQ ID NO: 9 (b) polynucleotides comprising a nucleotide sequence capable of hybridising selectively to the nucleotide sequence set out in SEQ ID NO: 1, SEQ ID NO: 3, SEQ ID NO: 5 or SEQ ID NO: 7 or a fragment expressing polypeptide SEQ ID NO: 9 (c) polynucleotides encoding a nuclear receptor polypeptide which comprises the sequence set out in SEQ ID NO: 2, SEQ ID NO: 4, SEQ ID NO: 6, :SEQ ID NO: 8, SEQ ID NO: 10 or a homologue, variant, derivative or fragment thereof containing SEQ ID NO. 10; and one or more transcription factor selected from a Sox gene, Krüppel-like factor gene or a gene from the myc family operably linked to a regulatory sequence capable of directing expression of said polynucleotide in a host cell.

Another aspect of the invention provides a method for inducing pluripotent stem cells in vitro in the manufacture of a medicament for treating a patient in need of a pluripotent stem cell treatment comprising the steps of: isolating cells from an individual donor; culturing the cells in vitro; introducing a polynucleotide that encodes a transcription factor into the cell in the culture, wherein the polynucleotide encodes a transcription factor comprises a nuclear receptor and one or more transcription factor selected from a Sox gene, Krüppel-like factor gene or an myc family of genes to induce the cell to be a pluripotent cell; introducing the pluripotent cell to the patient in need of a pluripotent stem cell treatment.

Another aspect of the invention provides a method of making pluripotent stem cell lines comprises: culturing cells in vitro; introducing a polynucleotide that encodes a transcription factor into the cell in the culture, wherein the polynucleotide encodes a transcription factor comprising a nuclear receptor and one or more transcription factor selected from a Sox gene, Krüppel-like factor gene or an myc family of genes to induce the cell to be a pluripotent cell; passaging the pluripotent cells to maintain the cell line.

Other aspects of the invention include those apparent to a person skilled in the art with reference to the description and figures of the preferred embodiments.

(D) Number of GFP-positive colonies generated from the reprogramming of MEFs with Nr5a2, Sox2 and Klf4. For control experiment, only SK retroviruses were introduced. Data in A to D represent mean±s.e.m. of three retrovirus-mediated transduction experiments (n=3).

(E) Generation of iPSC colonies after retroviral transduction of Pou5f1-GFP MEFs with Nr5a2, Sox2 and Klf4. Phase contrast image is shown.

(F) Colonies in E are GFP-positive when viewed under a fluorescence microscope, indicating the reactivation of endogenous Pou5f1.

(G) $N_2SK$ iPSCs expresses alkaline phosphatase.

(H) Expression of Nanog in $N_2SK$ iPSCs.

(I) Nuclei in H were counterstained with Hoechst.

(J) SSEA-1 expression in $N_2SK$ iPSCs.

(K) Cells in J were stained with Hoechst to indicate nuclei. Scale bars represent 200 μm in E-G and 50 μm in H-K.

(L) Brightfield image of the male gonad dissected from the E13.5 $N_2SK$ #B3 chimeric embryo.

(M) GFP fluorescence image of L. Positive GFP signals were observed in the gonads, indicating germline incorporation of Nr5a2-reprogrammed cells.

(N) $N_2SK$ #B11 adult chimera generated from Nr5a2-reprogrammed cells derived from F1 (129S2/SV×Pou5f1-GFP) MEFs which were microinjected into B6(Cg)-Tyr$^{c-2J}$/J embryos.

(O) Offsprings generated from the mating of $N_2SK$ #B11 adult chimera with an albino B6(Cg)-Tyr$^{c-2J}$/J mouse. Agouti and black offsprings are indicative of germline transmission of the Nr5a2-reprogrammed cells.

Figure 13:
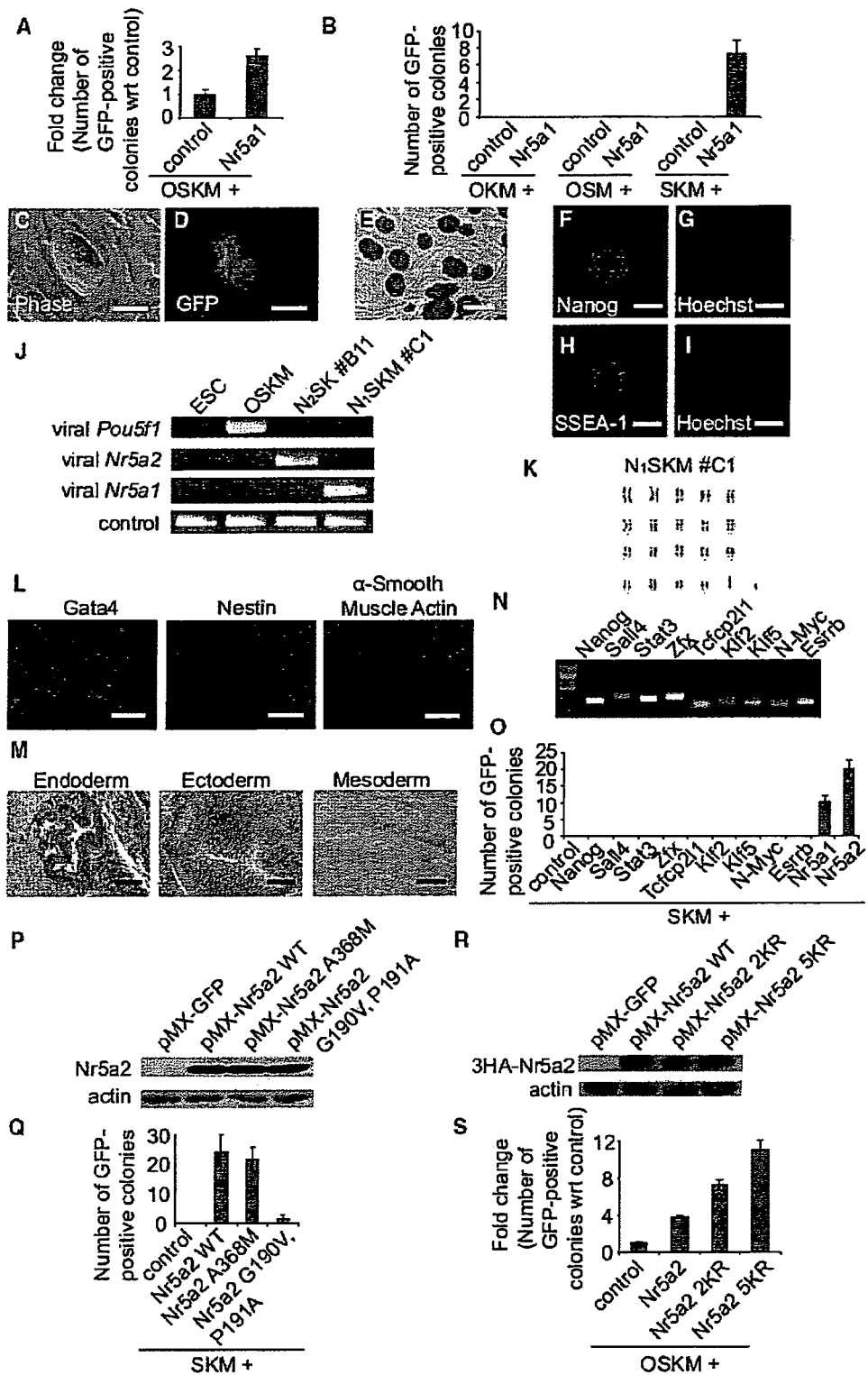

FIG. 13. Nr5a1-mediated reprogramming and the effect of mutations on reprogramming capability of Nr5a2

(A) Nr5a1 enhances the reprogramming efficiency with OSKM. Graph depicts fold change of number of GFP-positive colonies generated from Nr5a1 in conjunction with OSKM with respect to the control (OSKM).

(B) Nr5a1 replaces Oct4 in the reprogramming of MEFs. Nr5a1 was investigated for its ability to replace Sox2, Klf4 and Oct4 by co-transducing Nr5a1 in conjunction with OKM, OSM or SKM, respectively. Control experiments were performed with OKM, OSM or SKM retroviruses in the absence of Nr5a1.

(C) Phase contrast image of iPSC colonies generated from the retroviral transduction of Pou5f1-GFP MEFs with Nr5a1 and SKM.

(D) GFP-positive $N_1$SKM iPSC colonies in C.

(E) Nr5a1-reprogrammed cells stained positive for alkaline phosphatase.

(F) Nanog expression in Nr5a1-reprogrammed cells (G) Hoechst staining of F indicates nuclei.

(H) Nr5a1-reprogrammed cells stained positive for SSEA-1

(I) Hoechst staining of H indicates nuclei.

(J) PCR verification of genomic integration of retroviral gene Nr5a1 in a $N_1$SKM line. The control panel shows PCR amplification of a region of the p21 gene.

(K) Normal karyotype of a Nr5a1-reprogrammed line.

(L) EB-mediated in vitro differentiation assay performed on Nr5a1-reprogrammed cells. Differentiated cells stained positive for Gata4 (endoderm), Nestin (ectoderm) and α-Smooth Muscle Actin (mesoderm). Lineage markers were stained red and nuclei were stained blue with Hoechst.

(M) Teratoma assay of Nr5a1-reprogrammed cells. Scale bars represent 200 μm in C-E, 100 μm in L and 50 μm in F-I, M.

(N) PCR verification of viral transcript expression of Nanog, Sall4, Stat3, Zfx, Tcfcp2l1, Klf2, Klf5, N-Myc and Esrrb.

(O) Screen of transcription factors that bind to Pou5f1 regulatory regions in combination with SKM. Control represents transduction of only SKM viruses into MEFs. Nr5a1 and Nr5a2 with SKM were used as positive controls.

(P) Western analysis of cell extracts harvested from 293-T cells transfected with either retroviral vectors encoding Nr5a2 WT, Nr5a2 A368M and Nr5a2 G190V, P191A. 293-T cells transfected with retroviral vector harboring the GFP gene was used as a negative control.

(Q) SKM reprogramming with Nr5a2 ligand and DNA binding mutants. Pou5f1-GFP MEFs were transduced with SKM viruses and viruses encoding either Nr5a2 WT, Nr5a2 A368M or Nr5a2 G190V, P191A. Control experiment denotes infection of MEFs with only SKM viruses.

(R) Western analysis of cell extracts harvested from 293-T cells transfected with either retroviral vectors encoding Nr5a2 WT, Nr5a2 2KR and Nr5a2 5KR. 293-T cells transfected with retroviral vector not harboring any gene was used as a negative control.

(S) OSKM reprogramming with Nr5a2 SUMO mutants. Control experiment denotes infection of MEFs with only OSKM viruses. Graph depicts fold change of number of GFP-positive colonies generated from the infection of Pou5f1-GFP MEFs with OSKM viruses and viruses encoding either Nr5a2 WT, Nr5a2 2KR or Nr5a2 5KR with respect to that of the control. Data in A-B, O, Q and S represent mean±s.e.m. of three retrovirus-mediated transduction experiments (n=3).

Figure 14:
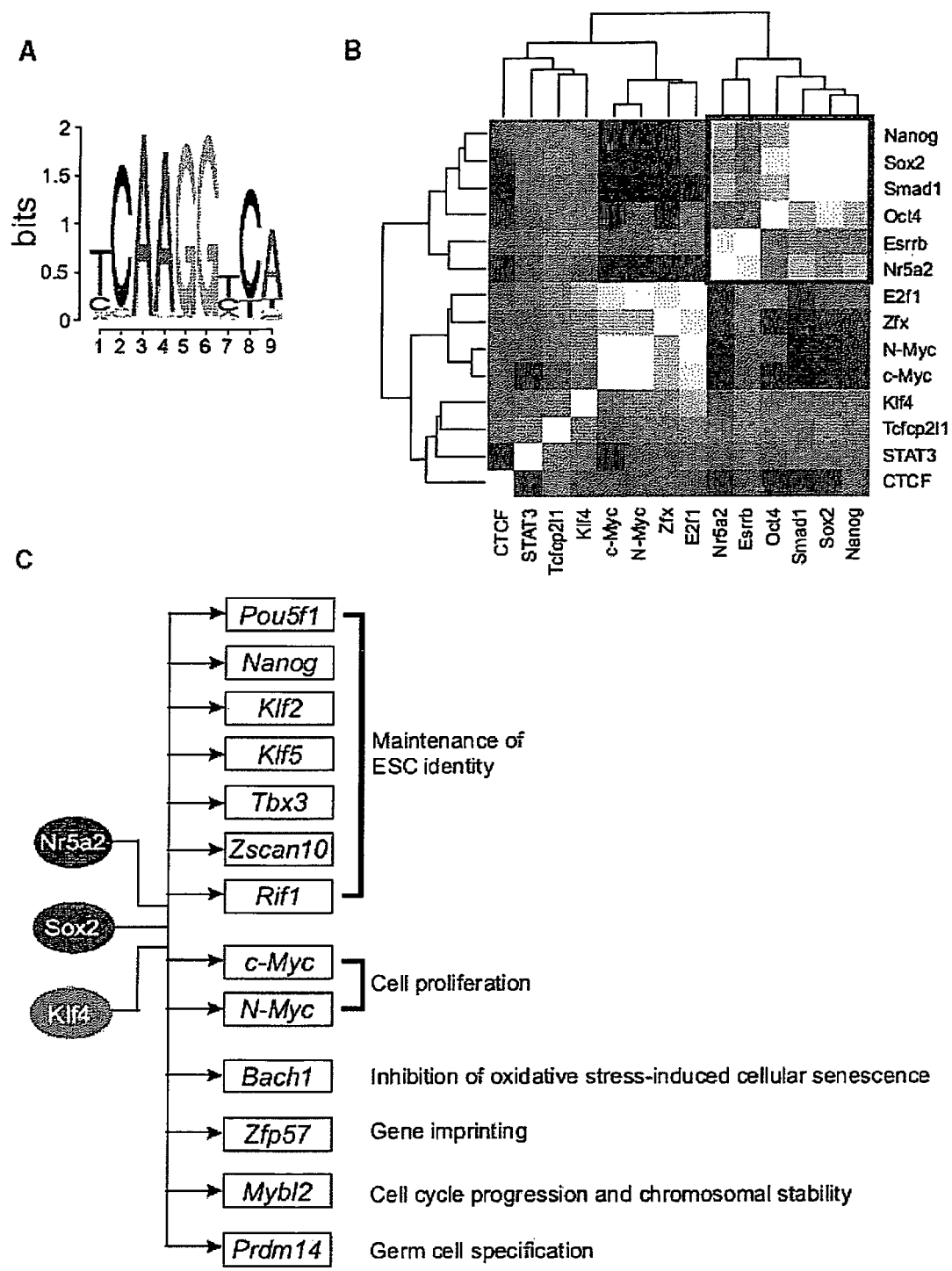

FIG. 14. Genome-wide mapping of Nr5a2 binding sites (A) Motif of Nr5a2 generated by the de novo motif discovery algorithm MEME which scans for overrepresented sequences of Nr5a2-bound sites.

(B) Heat map depicting the co-occurrence of Nr5a2 and other transcription factors. Each square in the heat map denotes the frequency of co-localization between two transcription factors (red represents less frequently co-localized and yellow represents more frequently co-localized). Transcription factors have been clustered along both axes based on the similarity in their co-localization with other factors. Transcription factors demarcated by the blue box tend to co-localize with Nr5a2.

(C) Genes important in various cellular roles such as maintenance of ESC identity and cell proliferation that are bound by Nr5a2, Sox2 and Klf4.

Figure 15:
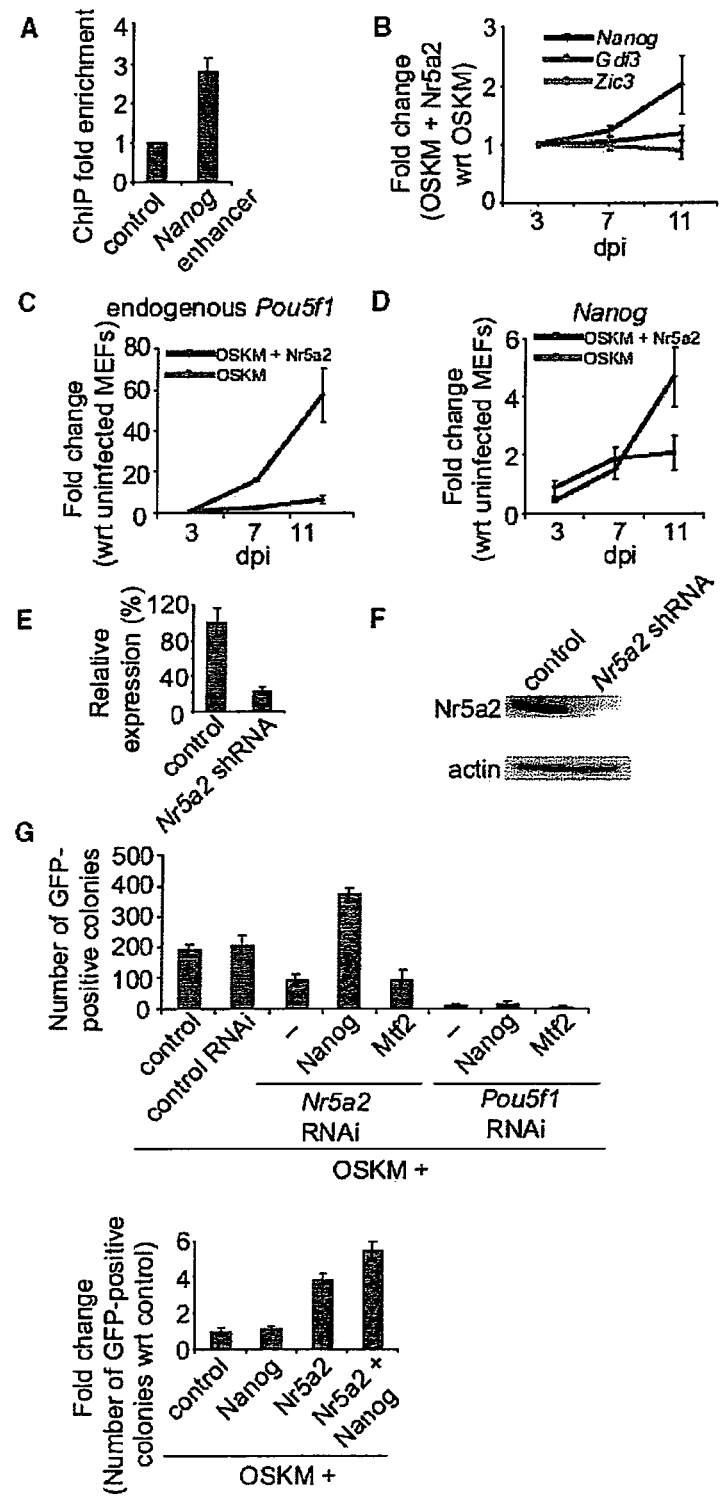

FIG. 15. Nanog is a downstream target of Nr5a2 in reprogramming (A) Nr5a2 binds to the Nanog enhancer during the reprogramming of MEFs. ChIP assay was performed on MEFs 8 days after being co-transduced with OSKM and HA-Nr5a2 viruses. Quantitative real-time PCR was performed to analyze the enrichment of HA-Nr5a2 on the Nanog enhancer using an anti-HA antibody. Data shown are mean±s.e.m. of biological duplicates.

(B) Fold change in expression levels of Nanog in OSKM+ Nr5a2 reprogramming cells as compared to OSKM reprogramming cells based on time-course (3, 7 and 11 dpi) biological triplicate microarray data (mean±s.e.m). Fold change in expression levels of ESC-relevant genes, Gdf3 and Zic3 were also included in the graph.

(C) Time-course fold change of endogenous Pou5f1 mRNA levels in OSKM+Nr5a2 or OSKM-infected MEFs with respect to uninfected MEFs.

(D) Time-course fold change of endogenous Nanog mRNA levels in OSKM+Nr5a2 or OSKM-infected MEFs with respect to uninfected MEFs. Real-time quantitative PCR data in C-D are mean±s.e.m of biological triplicate samples.

(E) Real-time quantitative PCR verification of Nr5a2 mRNA level in ESCs after Nr5a2 shRNA knockdown. Control ESCs were transfected with a shRNA construct targeting the luciferase gene.

(F) Western analyses of Nr5a2 protein expression in ESCs after introduction of knockdown construct targeting Nr5a2. Nr5a2 protein was targeted with an antibody specific to Nr5a2.

(G) shRNA knockdown of Nr5a2 in OSKM reprogramming. Pou5f1 RNAi with OSKM is used as a positive knockdown control while luciferase RNAi is used as a negative knockdown control. Nanog or Mtf2 was introduced to investigate their ability to rescue the knockdown effects.

(H) Reprogramming with OSKM in addition to both Nr5a2 and Nanog. Graph depicts fold change of number of GFP-positive colonies with respect to control. Data in E, G and H are mean±s.e.m. of three independent experiments (n=3).

Figure 16:
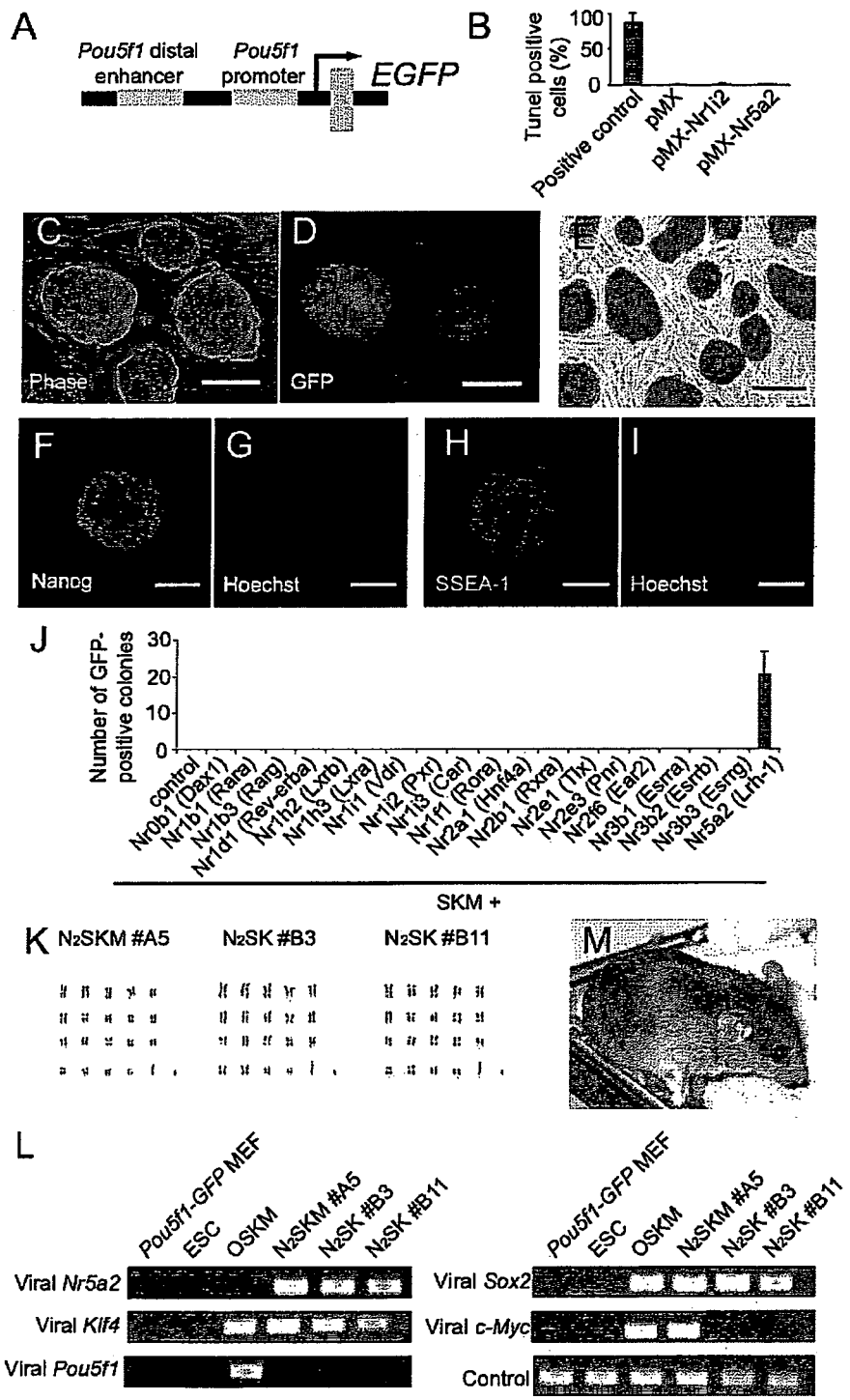

FIG. 16. Nr5a2 reprograms MEFs with Sox2, Klf4 and c-Myc (A) Schematic representation of the transgenic Pou5f1-Enhanced Green Fluorescent Protein (EGFP) reporter construct in MEFs. Expression of EGFP is under the control of Pou5f1 regulatory regions, which include the Pou5f1 distal enhancer and Pou5f1 promoter (Szabo et al., 2002).

(B) Tunel assay of Nr5a2 and Nr1i2-infected MEFs. Graph shows percentage of tunel-positive cells after fluorescence activated cell sorting (FACS) analysis. MEFs were infected with retroviruses encoding either no gene (pMX), Nr1i2 (pMX-Nr1i2) or Nr5a2 (pMX-Nr5a2). For positive control, uninfected MEFs were subjected to DNase 1 treatment prior to Tunel labeling. Data represent mean±s.e.m. of three retrovirus-mediated transduction experiments (n=3).

(C) Phase contrast image of iPSC colonies derived from the retroviral transduction of Pou5f1-GFP MEFs with Nr5a2, Sox2, Klf4 and c-Myc.

(D) Fluorescence image of C shows the restoration of endogenous Pou5f1 in Nr5a2-reprogrammed cells.

(E) Alkaline phosphatase expression in $N_2$SKM iPSCs.

(F) Nanog expression in $N_2$SKM iPSCs.

(G) Nuclei in F are counterstained with Hoechst.

(H) Expression of SSEA-1 in $N_2$SKM iPSCs.

(I) Cells in H are stained with Hoechst to mark nuclei. Scale bars represent 200 µm in C-E and 50 µm in F-I.

(J) Screen of other nuclear receptors for their ability to replace Oct4. MEFs were co-transduced with SKM viruses and viruses encoding each of the nuclear receptor. SKM+Nr5a2 was used as a positive control. Control experiment represents transduction of MEFs with only SKM viruses. Number of GFP-positive colonies was counted on 14 dpi. Data represent mean±s.e.m. of three retrovirus-mediated transduction experiments (n=3).

(K) Karyotypic analysis of $N_2$SKM #A5, $N_2$SK #B3 and $N_2$SK #B11 iPSC lines.

(L) Genotypic analysis of Nr5a2-reprogrammed cells. PCR verification of genomic integration of retroviral genes, Nr5a2, Sox2, Klf4 and c-Myc in Nr5a2-reprogrammed cells was performed on genomic DNA harvested from ESCs, MEFs and iPSCs with a viral-specific primer and a gene-specific primer. OSKM iPSCs were derived from the viral transduction of MEFs with Oct4, Sox2, Klf4 and c-Myc. PCR amplification of a region of the p21 gene was performed on all samples and is shown in the control panel.

(M) Adult mouse chimera generated from the microinjection of $N_2$SKM #A5 iPSCs derived from F1 (129S2/SV× Pou5f1-GFP) MEFs into C57BL/6J embryos.

Figure 17:
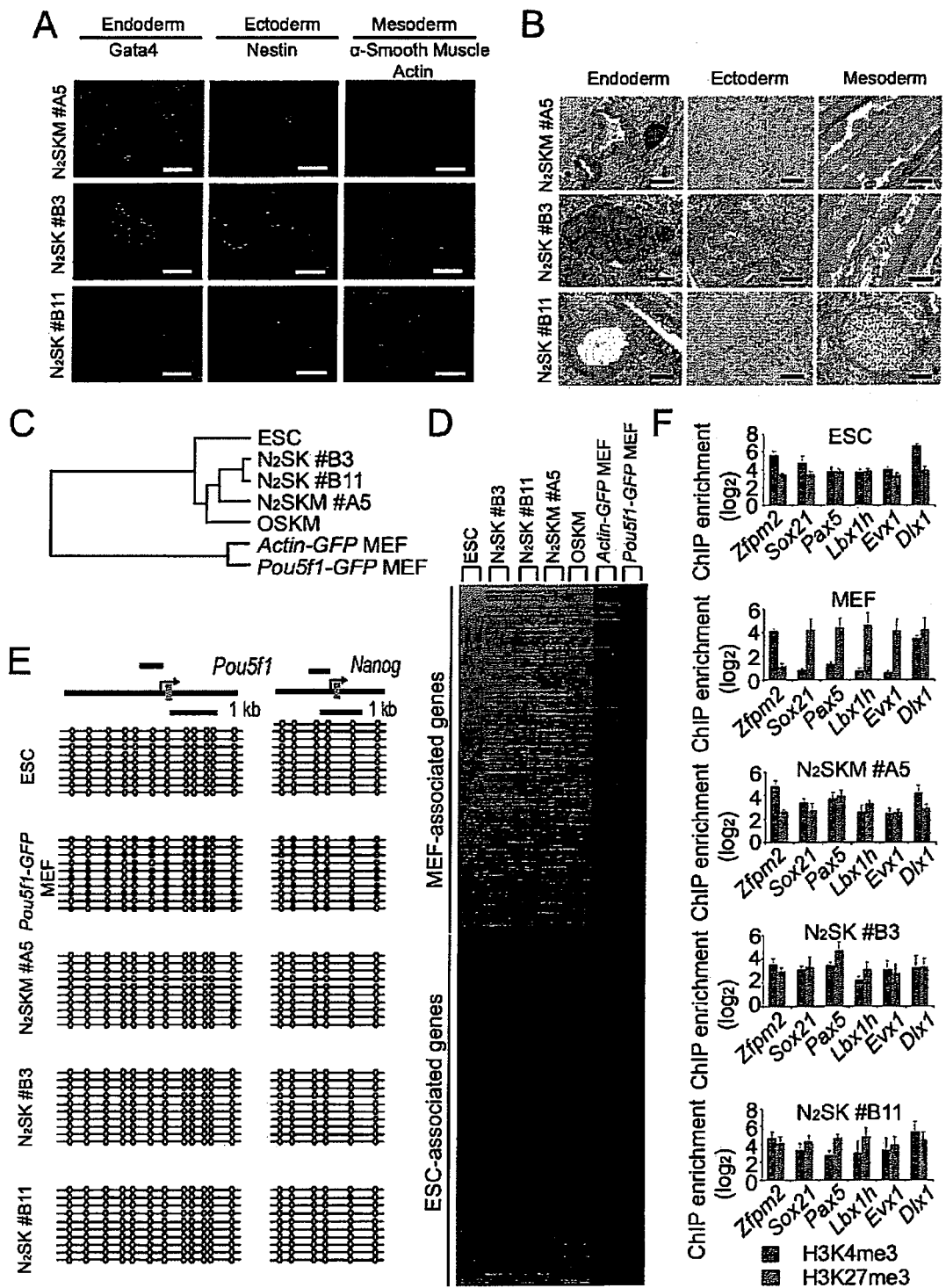

FIG. 17. Nr5a2-reprogrammed cells differentiate into lineages of the three major germ layers in the in vitro and in vivo differentiation assays, and global expression profiling and epigenetic state of Nr5a2-reprogrammed cells (A) Embryoid body (EB)-mediated in vitro differentiation assay showed that Nr5a2-reprogrammed cells could differentiate into cells of the three major embryonic lineages. Cells differentiated from Nr5a2-reprogrammed cells stained positive for Gata-4 (endoderm), Nestin (ectoderm) and α-Smooth Muscle Actin (mesoderm). Differentiation markers were stained red and Hoechst dye counterstained the nuclei blue.

(B) Nr5a2-reprogrammed cells differentiated into tissues of the three primary germ layers in the teratoma assay. Teratomas sectioned and stained with Mallory's tetrochrome revealed ectodermal tissue (neural ectoderm), mesodermal tissue (muscle and cartilage) and endodermal tissue (gut epithelium and pancreatic cells). Scale bars represent 100 µm in A and 50 µm in B.

(C) Correlation analysis (46,643 probes) was carried out to cluster the transcriptome of ESCs, iPSCs (OSKM, $N_2$SKM #A5, $N_2$SK #B3 and $N_2$SK #B11) and MEFs (actin-GFP and Pou5f1-GFP).

(D) Heatmap generated from the microarray data in C displays the expression profile of 1,000 ESC-associated and MEF-associated genes. Genes were selected based on fold differences of expression in ESCs and Pou5f1-GFP MEFs and were sorted by average expression ratio and mean-centered to the Pou5f1-GFP MEF signal. Green represents downregulation of gene expression while red represents upregulation of gene expression with respect to Pou5f1-GFP MEFs.

(E) Pou5f1 and Nanog promoter methylation analysis of Nr5a2-reprogrammed cells. Bisulfite genomic sequencing was performed to analyze methylation status of the promoter region of Pou5f1 and Nanog in ESCs, MEFs and Nr5a2-reprogrammed cells. For each cell line, ten random clones were sequenced and the results are displayed in circles in which open circles represent unmethylated CpG dinucleotides while red circles represent methylated CpG dinucleotides.

(F) Bivalent chromatin marks in Nr5a2-reprogrammed cells. Following ChIP assay, quantitative real-time PCR was performed to analyze the enrichment of trimethylated histone H3K4 and H3K27 chromatin marks in ESCs, MEFs and Nr5a2-reprogrammed cells. Data represents $Log_2$ enrichment for reported bivalent gene loci (Zfpm2, Sox21, Pax5, Lbx1h, Evx1 and Dlx). Data shown are mean±s.e.m. of three independent experiments (n=3).

Figure 18:
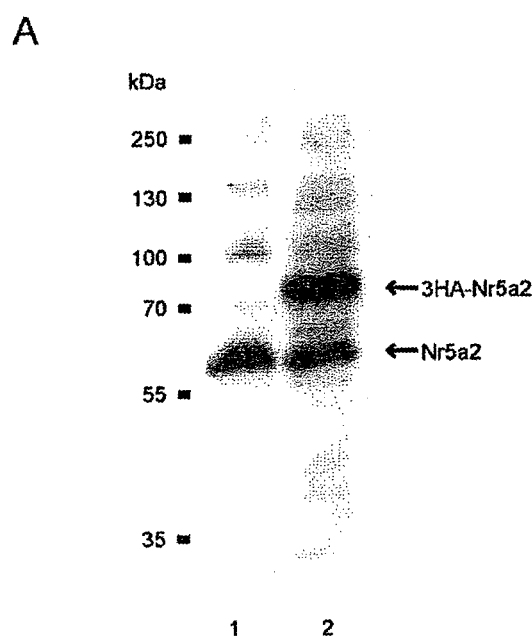
Figure 18:
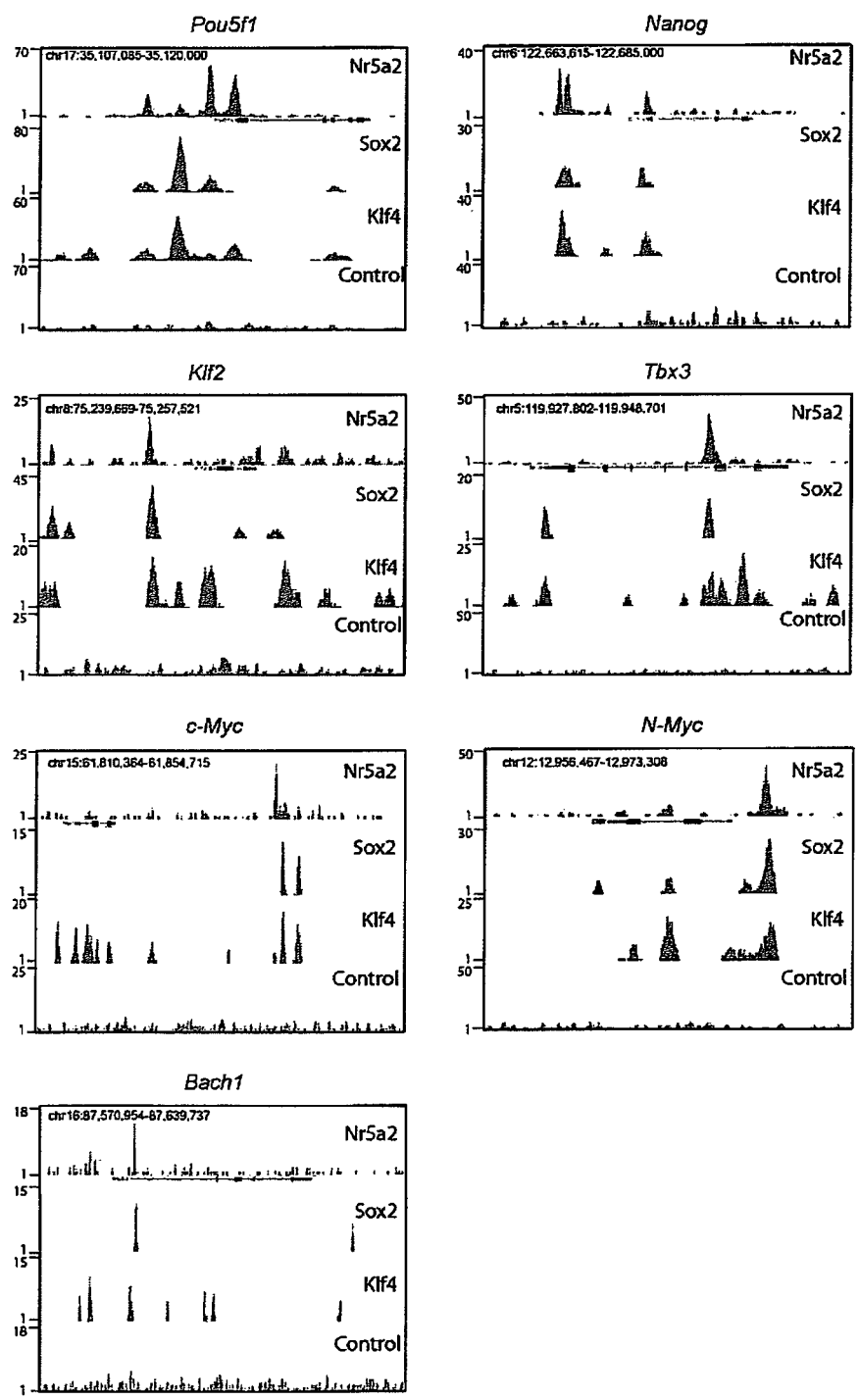

FIG. 18. ChIP-seq binding profiles of Nr5a2, Sox2 and Klf4 to common target genes (A) Cell lysate of ESCs was loaded into lane 1 and endogenous Nr5a2 protein was targeted by an Nr5a2-specific antibody. In lane 2, cell lysate of Nr5a2 3HA-tagged (three HA tags in tandem) stable cell line was loaded. Upper band represents 3HA-tagged Nr5a2 protein whereas lower band represents endogenous Nr5a2 protein.

(B) Binding profiles of Nr5a2, Sox2 and Klf4 to common target genes. The transcription factor trio, Nr5a2, Sox2 and Klf4, binds to pluripotency and self-renewal genes such as Pou5f1, Nanog, Klf2, Tbx3. These transcription factors also bind to cell proliferation genes such as c-Myc, N-Myc and genes involved in oxidative stress-induced cellular senescence such as Bach1. The binding profiles of each of the transcription factor to these target genes from our current and previous ChIP-seq analyses (Chen et al., 2008) are depicted in the plot as shown.

DETAILED DISCLOSURE

The present invention derives from our discovery that nuclear receptors, preferably members of the nuclear receptor subfamily 5 are able to replace Oct4 in the derivation of iPSCs from somatic cells in vitro. Further orphan nuclear receptor Nr5a2 (also known as Lrh-1) is also able to enhance the efficiency of reprogramming with OSKM. Hence, we were interested in testing the reprogramming capacity of Nr5a2 with mutated lysine residues, using a mutant construct with two lysine residues mutated (2KR) and another with five lysine residues mutated (5KR). Western analysis showed that the WT and mutant constructs expressed similar levels of protein (FIG. 13R). Strikingly, the OSKM reprogramming assay revealed that the 2KR mutant boosted reprogramming efficiency to at least 7-fold as compared to the 4-fold enhancement achieved by the WT (FIG. 13S). When the 5KR mutant was introduced, reprogramming efficiency was further augmented to almost 11-fold (FIG. 13S). These results suggest that the concomitant prevention of subcellular localization and the enhanced transcriptional activity brought about by the SUMO site mutations could trigger a greater induction of reprogramming by Nr5a2. The nuclear receptor subfamily 5-reprogrammed cells are positive for ESC-specific markers, are able to form teratomas comprising tissues of the three lineages and give rise to chimeras. Taken together, our study shows that transcription factors unrelated to Oct4 can replace Oct4 and highlights the roles of nuclear receptors as important factors in reprogramming.

On the basis of the above, the present invention provides a method for inducing pluripotent stem cells in vitro comprising the steps of: culturing cells in vitro; introducing a polynucleotide that encodes a transcription factor into the cell in the culture, wherein the polynucleotide encodes a transcription factor comprises a nuclear receptor and one or more transcription factor selected from a Sox gene, Krüppel-like factor gene or a gene from the myc family to induce the cell to be a pluripotent cell.

Nuclear receptors have the ability to directly bind to DNA and regulate the expression of adjacent genes. Nuclear receptors are modular in structure and contain specific domains such as DNA binding domain (DBD) and Ligand binding domain (LBD). In a preferred embodiment the nuclear receptor comprises one of the nuclear receptors listed in table 1. Preferably the nuclear receptor comprises a nuclear receptor from subfamily 5. The nuclear receptors in subfamily 5 include Nr5a1 and Nr5a2. In a preferred embodiment the nuclear receptor comprises Nr5a2 or a sumoylated mutant thereof.

There are 20 human SOX genes and around 30 Sox genes in total have been identified. A Sox gene is a transcription factor that binds to the minor groove in DNA. Sox stand for Sry-related HMG box. A Sox gene is characterized by a sequence called the HMG (high mobility group) box. This HMG box is a DNA binding domain that is highly conserved throughout eukaryotic species. The Sox family has no singular function, and many members possess the ability to regulate several different aspects of development. Sox genes include SOX1 involved in early development of the central nervous system, Sox2 and Sox3 involved in the transition of epithelial granule cells in the cerebellum to their migratory state, Sox 5 involved in the regulation of embryonic development and in the determination of the cell fate as well as many other Sox genes known to those skilled in the art. Preferably the Sox gene comprises Sox 2, Sox 1 and Sox 5. In a preferred embodiment the Sox gene is selected from the group of Sox 2, Sox 1 and Sox 5.

The Krüppel-like factor family of transcription factors (Klfs), are characterised by their three Cys2 His2 zinc fingers located at the C terminus separated by a highly conserved link. The following human genes encode Kruppel-like factors: KLF1, KLF2, KLF3, KLF4, KLF5, KLF6, KLF7, KLF8, KLF9, KLF10, KLF11, KLF12, KLF13, KLF14, KLF15, KLF16, or KLF17. In a preferred embodiment the Krüppel-like factor comprises klf4, klf2 or klf5. In a preferred embodiment the Krüppel-like factor is selected from the group of klf4, klf2 and klf5.

Myc family of genes comprises transcription factors, which contain the bHLH/LZ (basic Helix-Loop-Helix/Leucine Zipper) domain. Myc family of genes includes N-Myc and L-Myc genes. In a preferred embodiment the gene from the Myc-family comprises N-Myc, L-Myc or C-Myc. In a preferred embodiment the gene from the Myc-family is selected from the group of N-Myc, L-Myc and C-Myc.

Vectors

The present invention also provides a vector comprising a polynucleotide of the invention, for example an expression vector comprising a polynucleotide of the invention, operably linked to regulatory sequences capable of directing expression of said polynucleotide in a host cell.

Any nuclear receptor nucleic acid specimen, in purified or non-purified form, can be utilised as the starting nucleic acid or acids.

PCR is one such process that may be used to amplify isolated nuclear receptor sequences. This technique may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid that contains one strand of each may be utilized. A mixture of nucleic acids may also be employed, or the nucleic acids produced in a previous amplification reaction described herein, using the same or different primers may be so utilised.

The specific nucleic acid sequence to be amplified, may be a fraction of a nucleic acid or can be present initially as a discrete nucleic acid, so that the specific sequence constitutes the entire nucleic acid. It is not necessary that the sequence to be amplified is present initially in a pure form; it may be a minor fraction of a complex mixture, such as contained in whole human DNA.

DNA utilized herein may be extracted from a body sample, such as blood, tissue material, lung tissue and the like by a variety of techniques known in the art. If the extracted sample has not been purified, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP and dTTP are added to the synthesis mixture, either separately or together with the primers, in adequate amounts and the resulting solution is heated to about 90 degrees-100 degrees C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40 degree C. Most conveniently the reaction occurs at room temperature.

Primers direct amplification of a target polynucleotide (e.g. nuclear receptor such as subfamily 5). Primers used should be of sufficient length and appropriate sequence to provide initiation of polymerization. Environmental conditions conducive to synthesis include the presence of nucleoside triphosphates and an agent for polymerisation, such as DNA polymerase, and a suitable temperature and pH.

Primers are preferably single stranded for maximum efficiency in amplification, but may be double stranded. If double stranded, primers may be first treated to separate the strands before being used to prepare extension products. Primers should be sufficiently long to prime the synthesis of nuclear receptor of the invention, into extension products in the presence of the inducing agent for polymerization. The exact length of a primer will depend on many factors, including temperature, buffer, and nucleotide composition. Oligonucleotide primers will typically contain 12-20 or more nucleotides, although they may contain fewer nucleotides.

Primers should be designed to be substantially complementary to each strand of the nuclear receptor genomic gene sequence. This means that the primers must be sufficiently complementary to hybridise with their respective strands under conditions that allow the agent for polymerisation to perform. In other words, the primers should have sufficient complementarity with the 5' and 3' sequences flanking the mutation to hybridise therewith and permit amplification of the nuclear receptor genomic gene sequence.

Oligonucleotide primers of the invention employed in the PCR amplification process that is an enzymatic chain reaction that produces exponential quantities of CD166 gene sequence relative to the number of reaction steps involved. Typically, one primer will be complementary to the negative (−) strand of the nuclear receptor gene sequence and the other is complementary to the positive (+) strand. Annealing the primers to denatured nucleic acid followed by extension with an enzyme, such as the large fragment of DNA polymerase I (Klenow) and nucleotides, results in newly synthesised + and − strands containing the target nuclear receptor gene sequence. Because these newly synthesized sequences are also templates, repeated cycles of denaturing, primer annealing, and extension results in exponential production of the region (i.e., the nuclear receptor gene sequence) defined by the primers. The product of the chain reaction is a discreet nucleic acid duplex with termini corresponding to the ends of the specific primers employed.

Oligonucleotide primers may be prepared using any suitable method, such as conventional phosphotriester and phosphodiester methods or automated embodiments thereof. In one such automated embodiment, diethylphosphoramidites are used as starting materials and may be synthesized as known in the art.

The agent for polymerisation may be any compound or system which will function to accomplish the synthesis of primer extension products, including enzymes. Suitable enzymes for this purpose include, for example, E. coli DNA polymerase I, Klenow fragment of E. coli DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products that are complementary to each nuclear receptor gene sequence nucleic acid strand. Generally, the synthesis will be initiated at the 3' end of each primer and proceed in the 5' direction along the template strand, until synthesis terminates, producing molecules of different lengths.

The newly synthesised nuclear receptor strand and its complementary nucleic acid strand will form a double-stranded molecule under hybridizing conditions described above and this hybrid is used in subsequent steps of the process.

The steps of denaturing, annealing, and extension product synthesis can be repeated as often as needed to amplify the target polymorphic gene sequence nucleic acid sequence to the extent necessary. The amount of the specific nucleic acid sequence produced will accumulate in an exponential fashion. This may also be achieve via real time PCR as known in the art.

Preferably, the method of amplifying nuclear receptor is by PCR, as described herein or real time PCR and as is commonly used by those of ordinary skill in the art. Alternative methods of amplification have been described and can also be employed as long as the nuclear receptor sequence amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest that are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for hincII with short overhang on the 5' end that binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37 degrees C. Unlike PCR and LCR, SDA does not require instrumented temperature cycling. Another amplification system useful in the method of the invention is the QB Replicase System. Although PCR is the preferred method of amplification if the invention, these other methods can also be used to amplify the nuclear receptor sequences as described in the method of the invention.

Polynucleotides of the invention may be incorporated into a recombinant replicable vector for introduction into a host cell. Such vectors may typically comprise a replication system recognized by the host, including the intended polynucleotide encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences localization signals may also be included where appropriate, whether from a native nuclear receptor protein or from other receptors or from secreted polypeptides of the same or related species, which allow the protein to move across cell membranes, and thus attain its functional topology. Such vectors may be prepared by means of standard recombinant techniques well known in the art.

An appropriate promoter and other necessary vector sequences will be selected so as to be functional in the host, and may include, when appropriate, those naturally associated with nuclear receptor genes. Examples of workable combinations of cell lines and expression vectors are known in the art. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are known. Appropriate non-native mammalian promoters might include the early and late promoters from SV40 or promoters derived from murine Moloney leukemia virus, mouse tumour virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection, or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of the polynucleotides into the host cell by any method known in the art, including, inter alia, those described above, will be referred to herein as "transformation." The cells into which have been introduced nucleic acids described below are meant to also include the progeny of such cells.

Polynucleotides

An isolated nuclear receptor nucleic acid molecule is disclosed which molecule typically encodes a nuclear receptor polypeptide. The nucleic acid molecule comprises any nucleic acid capable of encoding a functional nuclear receptor polypeptide listed in table 1. Preferably the nucleic acid molecule comprises a nucleic acid capable of encoding a nuclear receptor from subfamily 5, an allelic variant, or analog, including fragments, thereof. The nuclear receptors of subfamily 5 may include any one of Nr5a2, Nr5a1 or an allelic variant, or analog, including fragments, thereof that includes the DNA binding domain (DBD) and or an activation domain. Specifically provided are DNA molecules selected from the group consisting of: (a) DNA molecules set out in SEQ ID NOs.: 1, 3, 5, 7 or encode fragments thereof such as SEQ ID NO: 9; (b) DNA molecules that hybridize to the DNA molecules defined in (a) or hybridisable fragments thereof; and (c) DNA molecules that encode an expression for the amino acid sequence encoded by any of the foregoing DNA molecules.

Preferred DNA molecules according to the invention include DNA molecules comprising the sequence set out in SEQ ID NOs.: 1, 3, 5, 7 or that encode fragments thereof such as SEQ ID NO: 9.

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced there-from.

An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein that has been removed from its naturally occurring environment, and includes recombinant or cloned DNA isolates and chemically synthesized analogs or analogs biologically synthesized by heterologous systems.

"Nuclear receptor gene sequence," "nuclear receptor gene," "nuclear receptor nucleic acids" or " nuclear receptor polynucleotide" each refer to a polynucleotide that contains specific domains such as DNA binding domain (DBD) and the activation domain. Further, they refer to a polynucleotide that encode proteins listed in table 1. Preferably the nucleic acid molecule comprises a nucleic acid capable of encoding a nuclear receptor from subfamily 5, an allelic variant, or analog, including fragments, or mutants thereof. The nuclear receptors of subfamily 5 may include any one of Nr5a2, Nr5a1 or an allelic variant, or analog, including fragments, or mutants thereof that includes the DNA binding domain (DBD) and an activation domain. A sumoylated mutant may refer to an Nr5a2 or Nr5a1 mutant construct with lysine resides mutated for example Nr5a2 2KR set out in SEQ ID NO: 1 or SEQ ID NO: 3.

These terms, when applied to a nucleic acid, refer to a nucleic acid that encodes a nuclear receptor polypeptide, fragment, homologue mutant or variant, including, e.g., protein fusions, sumoylated mutant or deletions. The nucleic acids of the present invention will possess a sequence that is either derived from, or substantially similar to a natural nuclear receptor encoding gene or one having substantial homology with a natural nuclear receptor encoding gene or a portion thereof. The coding sequences for mouse nuclear receptor polypeptide from subfamily 5 are shown in SEQ ID NOs.: 5 and 7 with the amino acid sequence shown in SEQ IS NOs.: 6 and 8 to 10. The coding sequences for sumoylated nuclear receptor polypeptide from subfamily 5 are shown in SEQ ID NOs.: 1 and 3 with the amino acid sequence shown in SEQ ID NOs.: 2 and 4.

A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases. Examples of coding sequence for working substantially homologous fragments are shown in SEQ ID NOs.: 1,3,5 and 7 with the amino acid sequence shown in SEQ ID NOs.: 2,4,6 and 8 to 10.

Alternatively, substantial homology or (identity) exists when a nucleic acid or fragment thereof will hybridise to another nucleic acid (or a complementary strand thereof) under selective hybridisation conditions, to a strand, or to its complement. Selectivity of hybridisation exists when hybridisation that is substantially more selective than total lack of specificity occurs. Typically, selective hybridisation will occur when there is at least about 55% identity over a stretch of at least about 14 nucleotides, preferably at least about 65%, more preferably at least about 75%, and most preferably at least about 90%. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Thus, polynucleotides of the invention preferably have at least 75%, more preferably at least 85%, more preferably at least 90% homology to the sequences shown in the sequence listings herein. More preferably there is at least 95%, more preferably at least 98%, homology. Nucleotide homology comparisons may be conducted as described below for polypeptides. A preferred sequence comparison program is the GCG Wisconsin Bestfit program described below. The default scoring matrix has a match value of 10 for each identical nucleotide and −9 for each mismatch. The default gap creation penalty is −50 and the default gap extension penalty is −3 for each nucleotide.

In the context of the present invention, a homologous sequence is taken to include a nucleotide sequence which is at least 60, 70, 80 or 90% identical, preferably at least 95 or 98% identical at the amino acid level over at least 20, 50, 100, 200, 300, 500 or 1000 nucleotides with the nucleotides sequences set out in SEQ ID NOs.: 1, 3, 5 and 7 . In particular, homology should typically be considered with respect to those regions of the sequence that encode contiguous amino acid sequences known to be essential for the function of the protein rather than non-essential neighbouring sequences. Preferred polypeptides of the invention comprise a contiguous sequence having greater than 50, 60 or 70% homology, more preferably greater than 80, 90, 95 or 97% homology, to one or more of the nucleotides sequences encoding polypeptide sequences SEQ ID NOs.: 9 or 10, which encode amino acids 1 to 499, 1 to 560, 1 to 462, of SEQ ID NOs.: 6 or 8 respectively. Preferred polynucleotides may alternatively or in addition comprise a contiguous sequence having greater than 80, 90, 95 or 97% homology to the sequence of SEQ ID NOs.: 5 or 7 that encodes amino acids 1 to 499, 1 to 560, 1 to 462, 100 to 187, or 317 to 560 of SEQ ID NOs.: 6, 8, 9 or 10 respectively. Preferred nucleic acids preferably contain specific domains such as DNA binding domain (DBD) and the activation domain.

Nucleotide sequences are preferably at least 15 nucleotides in length, more preferably at least 20, 30, 40, 50, 100 or 200 nucleotides in length. Generally, the shorter the length of the polynucleotide, the greater the homology required to obtain selective hybridization. Consequently, where a polynucleotide of the invention consists of less than about 30 nucleotides, it is preferred that the % identity is greater than 75%, preferably greater than 90% or 95% compared with the nuclear receptor nucleotide sequences set out in the sequence listings herein. Conversely, where a polynucleotide of the invention consists of, for example, greater than 50 or 100 nucleotides, the % identity compared with the nuclear receptor nucleotide sequences set out in the sequence listings herein may be lower, for example greater than 50%, preferably greater than 60 or 75%.

Nucleic acid hybridisation will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30 degrees C., typically in excess of 37 degrees C., and preferably in excess of 45 degrees C. Stringent salt conditions will ordinarily be less than 1000 mM, typically less than 500 mM, and preferably less than 200 mM. However, the combination of parameters is much more important than the measure of any single parameter. An example of stringent hybridization conditions is 65° C. and 0.1×SSC (1×SSC=0.15 M NaCl, 0.015 M sodium citrate pH 7.0).

The "polynucleotide" compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, sumoylated site mutants and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Polypeptides

Full length nuclear receptor polypeptides of the present invention have at least 87 amino acids, encode a nuclear receptor in an animal, particularly a mammal, and include allelic variants, mutants or homologues. Nuclear receptor polypeptides of the invention also include fragments and derivatives of full length nuclear receptor polypeptides, particularly fragments or derivatives having substantially the same or enhanced biological activity. The nuclear receptor polypeptides include those comprising the amino acid sequences of SEQ ID NOs.: 2, 4, 6, 8, 9, 10 or allelic variants, mutants or homologues, including fragments, thereof such as SEQ ID NOs.: 9 or 10. A particularly preferred polypeptide consists of amino acids 1 to 560, 1 to 560, 1 to 499, 1 to 560, 1 to 462, of the amino acid sequence shown as SEQ ID NOs.: 2, 4, 6 or 8 respectively or allelic variants, homologues or fragments, thereof such as SEQ ID NOs.: 9 or 10.

The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analog of an amino acid (including, for example, natural isolated amino acids, etc.), polypeptides with substituted linkages as well as other modifications known in the art, both naturally and non-naturally occurring.

In the context of the present invention, a homologous sequence is taken to include an amino acid sequence which is at least 60, 70, 80 or 90% identical, preferably at least 95 or 98% identical at the amino acid level over at least 20, 50, 100, 200, 300 or 400 amino acids with the amino acid sequences set out in. In particular, homology should typically be considered with respect to those regions of the sequence known to be essential for the function of the protein such as the DNA binding domain an example of which is SEQ ID NO: 9 or the activation domain an example of which is SEQ ID NO: 10 rather than less important neighbouring sequences such as the ligand binding domain (LBD). Preferred polypeptides of the invention comprise a contiguous sequence having greater than 50, 60 or 70% homology, more preferably greater than 80 or 90% homology, to one or more of amino acids of SEQ ID NOs.: 2, 4, 6, 8, 9 or 10.

Other preferred polypeptides comprise a contiguous sequence having greater than 40, 50, 60, or 70% homology, of SEQ ID NOs.: 2, 4, 6, 8, 9 or 10. Although homology can also be considered in terms of similarity (i.e. amino acid residues having similar chemical properties/functions), in the context of the present invention it is preferred to express homology in terms of sequence identity. The terms "substantial homology" or "substantial identity", when referring to polypeptides, indicate that the polypeptide or protein in question exhibits at least about 70% identity with an entire naturally-occurring protein or a portion thereof, usually at least about 80% identity, and preferably at least about 90 or 95% identity.

Homology comparisons can be conducted by eye, or more usually, with the aid of readily available sequence comparison programs. These commercially available computer programs can calculate % homology between two or more sequences.

Percentage (%) homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take, into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Nuclear receptor polypeptide homologues include those having the amino acid sequences, wherein one or more of the amino acids is substituted with another amino acid which substitutions do not substantially alter the biological activity of the molecule to reprogram a differentiated cell to a pluripotent state. A nuclear receptor polypeptide homologue according to the invention preferably has 80 percent or greater with any of the amino acids listed in table 1. Preferably the nuclear receptor is from subfamily 5 and preferably has 80 percent or greater homology with any one of the sequence identity to a amino acid sequence set out in SEQ ID NOs.: 2, 4, 6, 8, 9 or 10. Examples of nuclear receptor polypeptide homologues within the scope of the invention include the amino acid sequence of SEQ ID NOs.: 2, 4, 6, 8, 9 or 10 wherein: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; or (e) one or more tyrosine or phenylalanine residues is substituted with tryptophan.

Preferably "nuclear receptor protein" or "nuclear receptor polypeptide" refers to a protein or polypeptide encoded by a nuclear receptor gene sequence, variants or fragments thereof. Preferably the "nuclear receptor protein" or "nuclear receptor polypeptide" refers to a protein or polypeptide listed in table 1. More preferably the "nuclear receptor protein" or "nuclear receptor polypeptide" refers to a protein or polypeptide of the subfamily 5. The nuclear receptors of subfamily 5 may include any one of Nr5a2, Nr5a1 or any variants mutants or fragments thereof. Also included are proteins encoded by DNA that hybridize under high or low stringency conditions, to nuclear receptor encoding nucleic acids and closely related polypeptides or proteins retrieved by antisera to the nuclear receptor protein (s).

"Protein modifications or fragments" are provided by the present invention for nuclear receptor polypeptides or fragments thereof which are substantially homologous to primary structural sequence but which include, e.g., in vivo or in vitro chemical and biochemical modifications or which incorporate unusual amino adds. Such modifications include, for example, sumoylated site mutations acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

Preferred polypeptides of the invention have substantially similar function to wild type full length nuclear transcription factor. Preferred polynucleotides of the invention encode polypeptides having substantially similar function to wild type full length nuclear transcription factor. "Substantially similar function" refers to the function of a nucleic acid or polypeptide homologue, variant, derivative or fragment of nuclear receptor with reference to the wild-type nuclear receptor nucleic acid or wild-type nuclear receptor polypeptide to reprogram somatic cells in accordance with the assays described herein.

Compositions of the Invention

Polypeptides produced according to the invention can be administered to somatic cells for reprogramming in the form of compositions.

Thus, the present invention also relates to compositions including pharmaceutical compositions comprising a therapeutically effective amount of a a nuclear receptor polypeptide and one or more transcription factor polypeptide selected from a Sox polypeptide, Krüppel-like factor polypeptide or a polypeptide from the myc family. As used herein a compound will be therapeutically effective if it is able to reprogramming somatic cells in vitro.

Compositions of the invention suitable for injectable use include sterile aqueous solutions (where water soluble) or dispersions and sterile powders for the extemporaneous preparation of sterile injectable solutions and or one or more carrier. Alternatively, injectable solutions may be delivered encapsulated in liposomes to assist their transport across cell membrane. Alternatively or in addition such preparations may contain constituents of self-assembling pore structures to facilitate transport across the cellular membrane. It must be stable under the conditions of manufacture and storage and must be preserved against the contaminating/destructive action of microorganisms such as, for example, bacteria and fungi.

The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as, for example, lecithin, by the maintenance of the required particle size in the case of dispersion and by the use of surfactants. Preventing the action of microorganisms in the compositions of the invention is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and freeze-drying, to yield a powder of the active ingredient plus any additional desired ingredient from previously sterile-filtered solution thereof.

Biologically acceptable carriers and/or diluents may also include any and all solvents, dispersion media, antibacterials and/or antifungals, isotonic and absorption delaying agents and the like. The use of such media and agents for culture is well known in the art. Except insofar as any conventional media or agent is incompatible with the active polypeptide, use thereof in the compositions is contemplated.

Polypeptides can also be delivered by protein delivery methods known in the art such as transfection as described above, macromolecule delivery vehicles and other methods known to those skilled in the art.

The compositions may be for use in reprogramming somatic cells. Use includes use of a composition of the invention for the preparation of a pluripotent cell as a medicament for the treatment of degenerative diseases where new cells are required.

Method of Inducing Pluripotent Cells for Use in Treatment

An embodiment of the present invention resides in a method for inducing pluripotent stem cells in vitro in the manufacture of a medicament for treating a patient in need of a pluripotent stem cell treatment comprising the steps of: isolating cells from an individual donor; culturing the cells in vitro; introducing a polynucleotide that encodes a transcription factor into the cell in the culture, wherein the polynucleotide encodes a transcription factor comprises a nuclear receptor and one or more transcription factor selected from the group Sox2, Klf4, c-Myc, Klf2, Klf5, Sox1, Sox5, N-myc and L-myc to induce the cell to be a pluripotent cell; introducing the pluripotent cell to the patient in need of a pluripotent stem cell treatment.

"Treatment" and "treat" and synonyms thereof refer to both therapeutic treatment and prophylactic or preventative measures, wherein the object is to prevent or slow down (lessen) a degenerative condition. Those in need of such treatment include those already diagnosed with stroke, cancer, diabetes, neurological disorders such as Parkinson's disease, Huntington's disease, Alzheimer's, dementia, as well as cardiac failure and muscle damage, along with many others.

As used herein a "therapeutically effective amount" of a compound will be an amount of cells that are capable of preventing or at least slowing down (lessening) a degenerative condition, in particular increasing the lifespan of the patent. Dosages and administration of cells of the invention may be determined by one of ordinary skill in the art. An effective amount of the cells to be employed therapeutically will depend, for example, upon the therapeutic objectives, the route of administration, and the condition of the mammal. Accordingly, it will be necessary for the therapist to adjust the dosage and modify the route of administration as required to obtain the optimal therapeutic effect.

Preferably, the pluripotent cells of the invention are used in neurological disorders such as Parkinson's disease, Huntington's disease, Alzheimer's, dementia or stroke.

Induced Pluripotent Stem Cell Lines

In one embodiment the method of making pluripotent stem cell lines comprises: culturing cells in vitro; introducing a polynucleotide that encodes a transcription factor into the cell in the culture, wherein the polynucleotide encodes a transcription factor comprises a nuclear receptor and one or more transcription factor selected from the group Sox2, Klf4, c-Myc, Klf2, Klf5, Sox1, Sox5, N-myc and L-myc to induce the cell to be a pluripotent cell; passaging the pluripotent cells to maintain the cell line.

Cell Preparation

A "cell", as used herein, refers to a biological sample obtained from a tissue in the body, or from body fluid. Frequently the cell will be a "clinical sample," which is a sample derived from a patient such as a fine needle biopsy sample. A "cell" may also include cells isolated from fluids such as blood, serum and the like. Cell samples can be isolated and obtained from tissues from lung, bladder, brain, uterus, cervix, colon, rectum, esophagus, mouth, head, muscle, heart, skin, kidney, breast, ovary, neck, pancreas, prostate, testis, liver gonads, stomach or from any other organ or tissue known to those skilled in the art.

Cell samples are obtained from the body and include cells and extracellular matter. Cell samples may be from humans or non human animals. Cell samples can be from any organ or fluid. Cell samples can be obtained using known procedures, such as excision, a needle biopsy, blood extraction or the like. The cells are to be processed in a manner that allows culturing and reprogramming of the cells. Accordingly, cells obtained from a subject, donor or individual are ideally washed then immediately cultured.

Cell Culture

The iPSC's may be cultured as known in the art on a relevant culture media such as an artificial medium to grow the cells in vitro for research or medical treatment. The cells may be passaged though several generations as known in the art to keep the cells continuous. The culture media may contain nutrients to nourish and support the cells. Culture medium may also include growth factors added to produce desired changes in the cells.

Examples of Preferred Embodiments

Reprogramming Capacity of Nuclear Receptors

Figure 1:
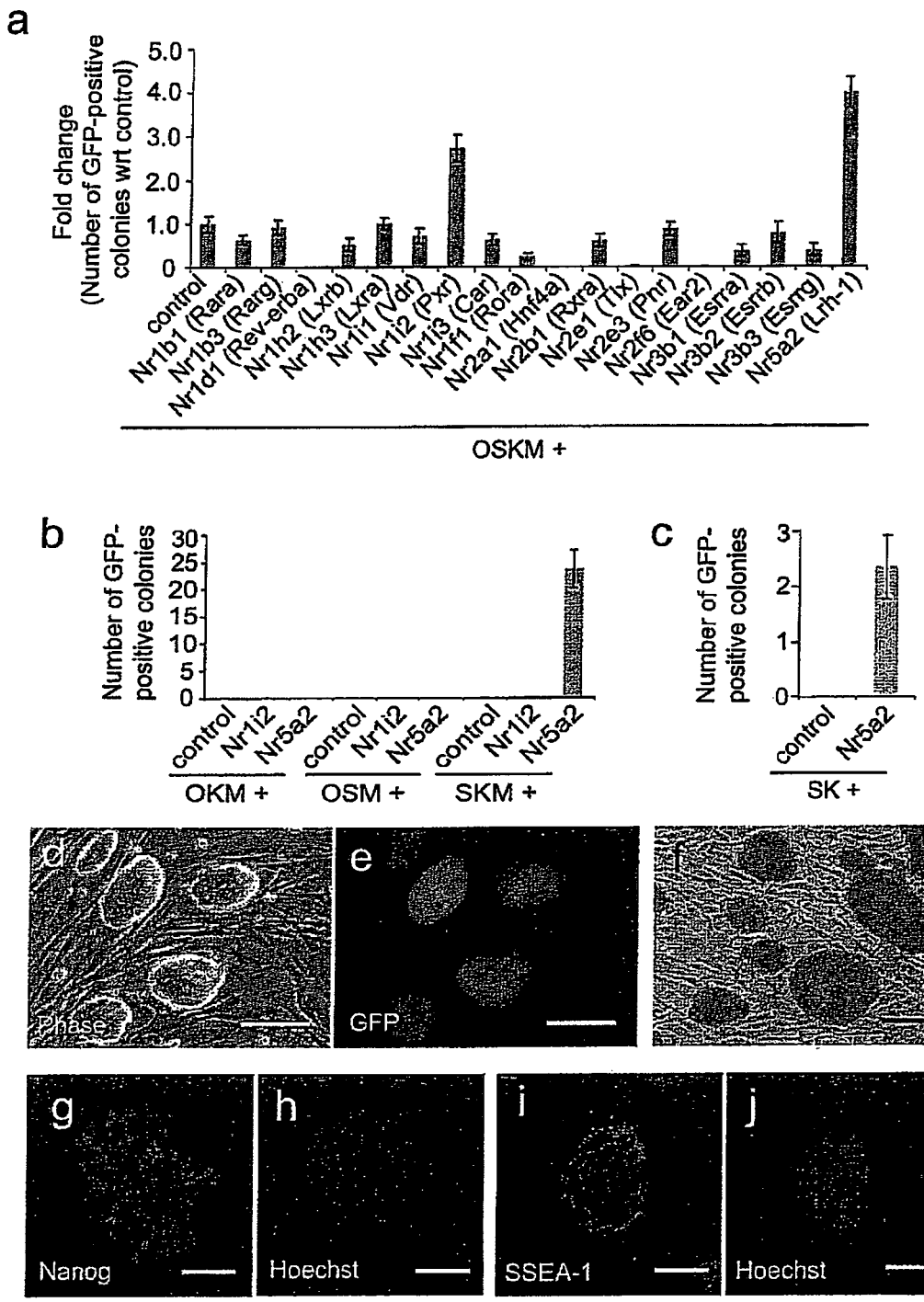
FIG. 1. Nr5a2 enhances reprogramming efficiency and can reprogram MEFs with Sox2 and Klf4, with or without c-Myc.
(a) Screen of 18 nuclear receptor s for the enhancement of MEF reprogramming with Oct4, Sox2, Klf4 and c-Myc (OSKM). Graph depicts the fold change of number of Pou5f1-GFP-positive colonies generated from each nuclear factor in conjunction with OSKM with respect to the OSKM (control). Data represent mean±s.e.m. of three retrovirus-mediated transduction experiments (n=3).
(b) Reprogramming enhancers, Nr1i2 and Nr5a2 were tested for their ability to replace Sox2, Klf4 and Oct4 in the reprogramming of MEFs. A quantitation of GFP-positive colonies was performed on 14 dpi. For control experiments, no nuclear receptor factors were introduced but only OKM, OSM or SKM retroviruses were added. Data represent mean±s.e.m. of three retrovirus-mediated transduction experiments (n=3).
(c) Number of GFP-positive colonies generated from the reprogramming of MEFs with Nr5a2 together with Sox2 and Klf4. For control experiment, only SK retroviruses were introduced to MEFs. Data represent mean±s.e.m. of three retrovirus-mediated transduction experiments (n=3).
(d) Generation of iPSC colonies after retroviral transduction of Pou5f1-GFP MEFs with Nr5a2, Sox2 and Klf4. Phase contrast image is shown.
(e) iPSC colonies in d are Pou5f1-GFP-positive when viewed under a fluorescence microscope, indicating the reactivation of endogenous Pou5f1.
(f) $N_2SK$ iPSCs expressed alkaline phosphatase.
(g) Expression of Nanog in $N_2SK$ iPSCs.
(h) Nuclei in g were counterstained with Hoechst.
(i) SSEA-1 expression in $N_2SK$ iPSCs.
(j) Cells in i were stained with Hoechst to indicate nuclei. Scale bars represent 200 μm in d-f and 50 μm in g-j.
Figure 5:
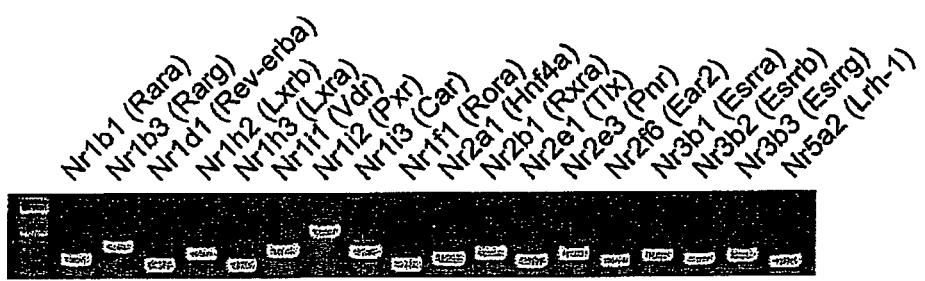
FIG. 5. Expression of viral constructs harboring the screened nuclear receptor genes verified by PCR amplification of cDNA with a virus specific primer and a gene-specific primer.

A screen of 18 nuclear receptors (Table 1) was performed to identify nuclear receptors that could enhance the efficiency of reprogramming. Mouse Embryonic Fibroblasts (MEFs) which contain an endogenous Pou5f1-GFP reporter were used in the screen. Reprogrammed MEFs were positively identified by the expression of GFP as a result of reactivation of the silenced Pou5f1-GFP reporter. The screen was conducted with each nuclear receptor retrovirally transduced with the Oct4 (O), Sox2 (S), Klf4 (K), and c-Myc (M) viruses. The frequency of Pou5f1-GFP-positive colonies was registered at 14 days post infection (dpi). Transcript expression of all the nuclear receptor constructs was also verified (FIG. 5). From this screen we found that both orphan nuclear receptor s Nr1i2 (also known as pregnane X receptor, Pxr) and Nr5a2 (also known as liver receptor homolog-1, Lrh-1), were able to enhance the efficiency of reprogramming (as compared to the OSKM control) by 2.7 and 4.0 fold, respectively (FIG. 1a).

TABLE 1

List of nuclear receptor s screened for enhancers of reprogramming.

| Nuclear receptor s (NRs) | Functions |
|---|---|
| Nr0b1 (Dax1) | Transcription factor, transcriptional repressor of several nuclear receptors |
| Nr1b1 (Rara) | Transcription factor, regulator of Oct4 |
| Nr1b3 (Rarg) | Transcription factor, regulator of Oct4 |
| Nr1d1 (Rev-erba) | Transcription factor, regulator of circardian and metabolic pathways |
| Nr1h2 (Lxrb) | Transcription factor, regulator of lipid and cholesterol homeostasis |
| Nr1h3 (Lxra) | Transcription factor, regulator of lipid and cholesterol homeostasis |
| Nr1i1 (Vdr) | Transcription factor, mediator of vitamin D |
| Nr1i2 (Pxr) | Transcription factor, regulator of cytochrome P450 |
| Nr1i3 (Car) | Transcription factor, regulator of cytochrome P450 |
| Nr1f1 (Rora) | Transcription factor, regulator of metabolic homeostasis |
| Nr2a1 (Hnf4a) | Transcription factor, regulator of liver-specific genes |
| Nr2b1 (Rxra) | Transcription factor, role in ESC differentiation to cardiomyocyte |
| Nr2e1 (Tlx) | Transcription factor, role in neurogenesis |
| Nr2e3 (Pnr) | Transcription factor, transcriptional repressor of cone-specific genes |
| Nr2f6 (Ear2) | Transcription factor, transcriptional repressor of IL-17 in T-cells |
| Nr3b1 (Esrra) | Transcription factor, role in osteoblast development |
| Nr3b2 (Esrrb) | Transcription factor, self-renewal regulator, reprogramming factor |
| Nr3b3 (Esrrg) | Transcription factor, reprogramming factor |
| Nr5a2 (Lrh-1) | Transcription factor, activator of Oct4 |

Figure 6:
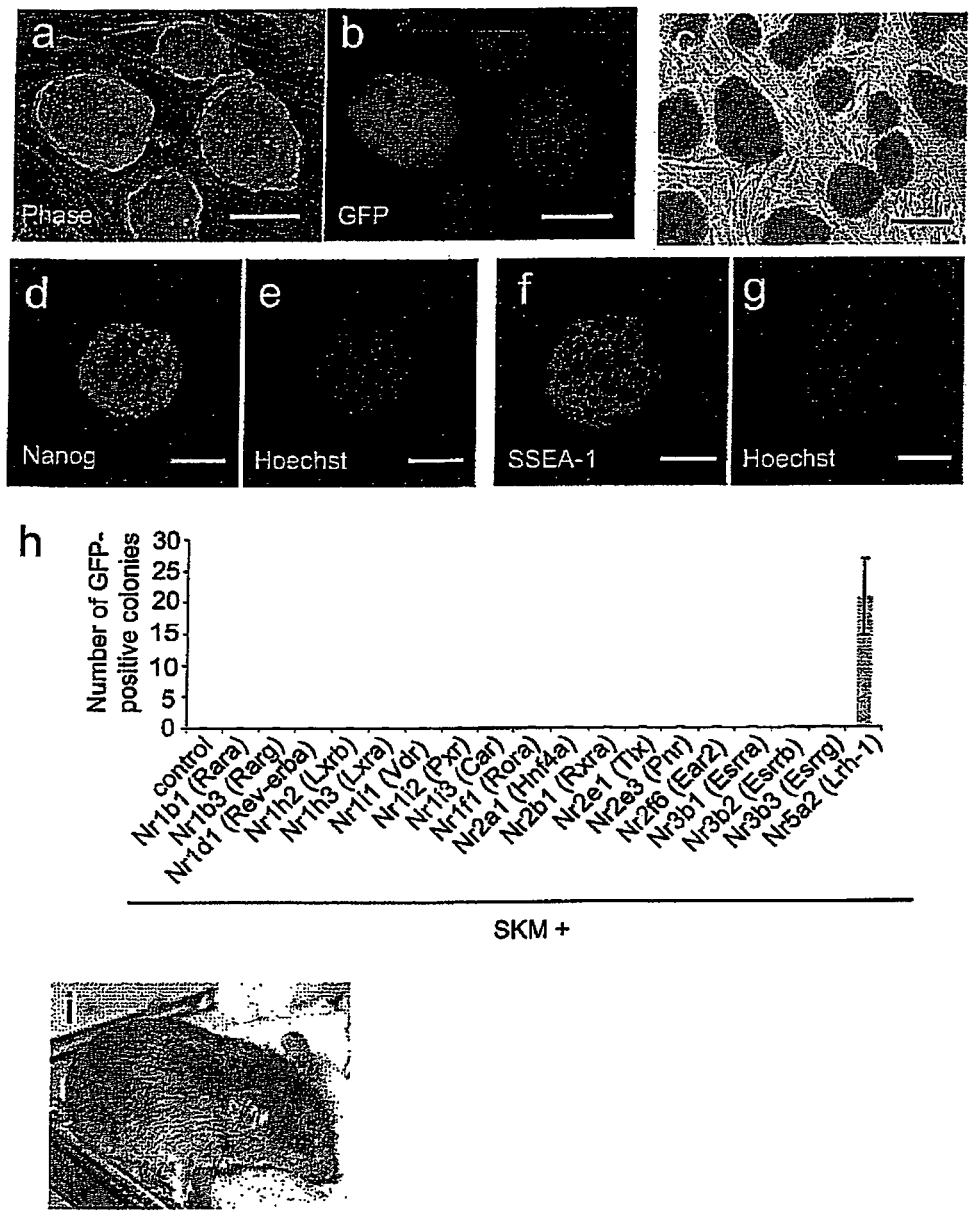
FIG. 6. Nr5a2 reprograms MEFs with Sox2, Klf4 and c-Myc.
(a) Phase contrast image of iPSC colonies derived from the retroviral transduction of Pou5f1-GFP MEFs with Nr5a2, Sox2, Klf4 and c-Myc.
(b) Fluorescence image of a show the restoration of endogenous Pou5f1 in Nr5a2-reprogrammed cells.
(c) Alkaline phosphatase expression in N2SKM iPSCs.
(d) Nanog expression in N2SKM iPSCs.
(e) Nuclei in d are counterstained with Hoechst.
(f) Expression of SSEA-1 in N2SKM iPSCs.
(g) Cells in f are stained with Hoechst to mark nuclei.
(h) A screen of the other nuclear receptor s for their ability to replace Oct4. MEFs were co-transduced with SKM viruses and viruses encoding each of the nuclear receptor. SKM+Nr5a2 were used as a positive control. Control experiment represents transduction of MEFs with only SKM viruses. Number of GFP-positive colonies was counted on 14 dpi. Data represent mean±s.e.m. of three retrovirus-mediated transduction experiments (n=3).
(i) Adult mouse chimera generated from the microinjection of N2SKM #A5 iPSCs derived from 129S2/SV Pou5f1-GFP MEFs into C57BL/6J embryos. Scale bars represent 200 µm in a-c and 50 µm in d-g.

We next sought to investigate if these enhancers of reprogramming could replace the core reprogramming factors. As c-Myc was previously shown to be dispensable for reprogramming we did not investigate the replaceability of c-Myc but instead investigated the ability of these two nuclear receptors in replacing any of the OSK trio. Strikingly, when Pou5f1-GFP MEFs were transduced with Nr5a2 and SKM viruses, Pou5f1-GFP-positive colonies (23.7±3.5 per 100,000 MEFs plated) were observed by 14 dpi (FIG. 1b and FIG. 6a-b). This demonstrates that besides augmenting reprogramming efficiency, exogenous Nr5a2 could also replace exogenous Oct4 in the reprogramming of MEFs. We refer to these cells that have been reprogrammed with Nr5a2, Sox2, Klf4 and c-Myc as N$_2$SKM iPSCs. These colonies could be stably passaged long-term and stained positive for alkaline phosphatase (FIG. 6c), Nanog (FIG. 6d-e) and SSEA-1 (FIG. 6f-g).

Given that c-Myc is dispensable for reprogramming, we were also able to generate iPSCs from Pou5f1-MEFs that were transduced with just Nr5a2 and SK viruses albeit at a lower efficiency (2.3±0.6 per 100,000 MEFs plated) than that of N$_2$SKM iPSCs (FIG. 1c-e). These three-factor Nr5a2-reprogrammed cells are referred to as N$_2$SK iPSCs. Similar to N$_2$SKM iPSCs, N$_2$SK iPSCs stained positive for alkaline phosphatase (FIG. 1f), Nanog (FIG. 1g-h) and SSEA-1 (FIG. 1i-j).

Figure 7:
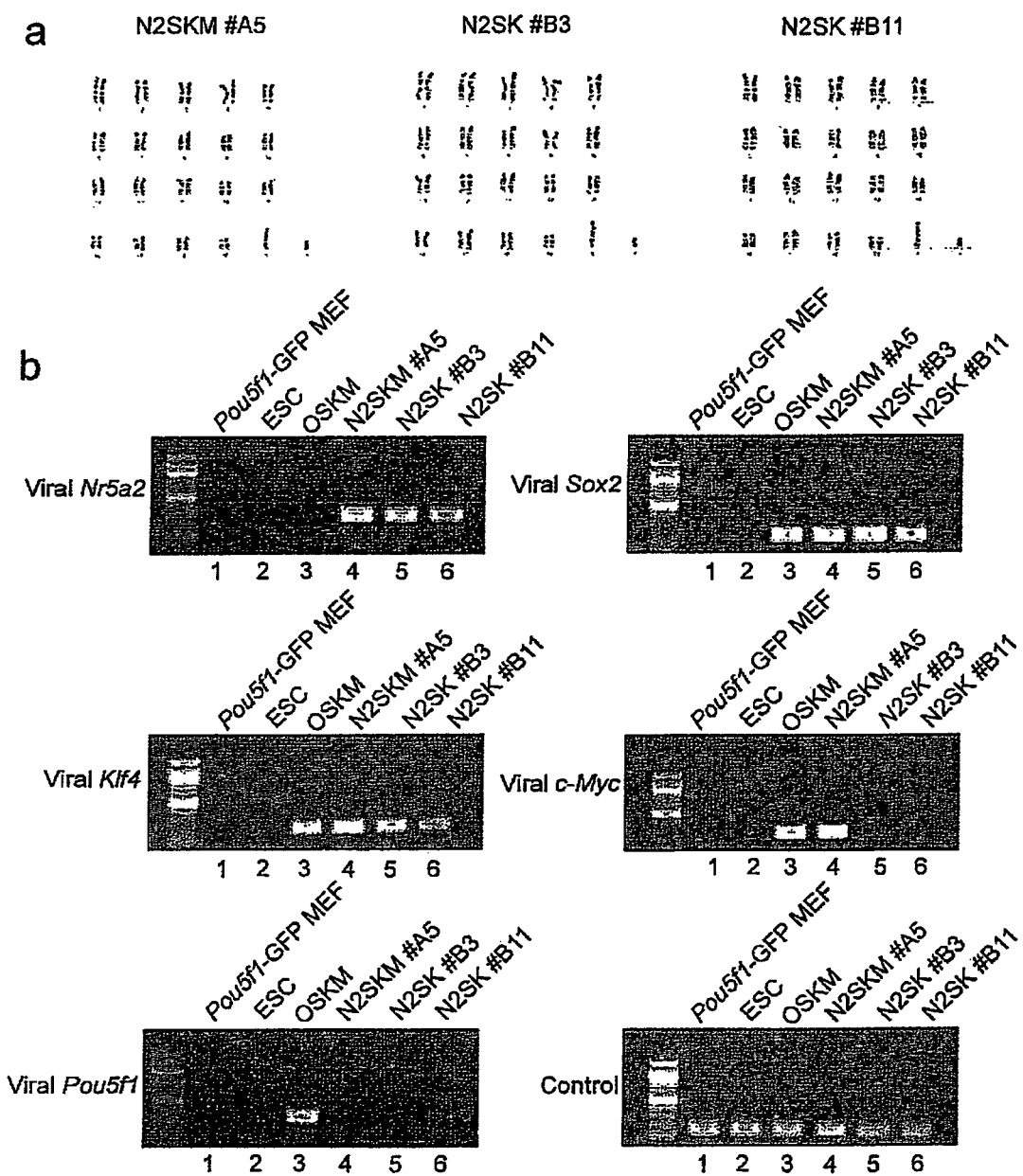
FIG. 7. Karyotypic and genotypic analysis of Nr5a2-reprogrammed cells.
(a) N2SKM #A5, N2SK #B3 and N2SK #B11 iPSC lines displayed normal male karyotype.
(b) PCR verified the genomic integration of retroviral genes, Nr5a2, Sox2, Klf4 and c-Myc in Nr5a2-reprogrammed cells. PCR was performed on genomic DNA harvested from ESCs, MEFs and iPSCs with a viral-specific primer and a gene specific primer. OSKM iPSCs were derived from the viral transduction of MEFs with Oct4, Sox2, Klf4 and c-Myc. PCR amplification of a region of the p21 gene was performed on all the samples and is shown in the control panel.

Nr5a2-reprogrammed cells were cytogenetically analyzed and shown to be karyotypically normal (FIG. 7a). In addition, genomic integrations of the respective viruses were tested and absence of Oct4-retroviruses in the genomic DNA of Nr5a2-reprogrammed cells was verified (FIG. 7b).

Characterisation of Cells Reprogrammed with Nr5a2

Figure 2:
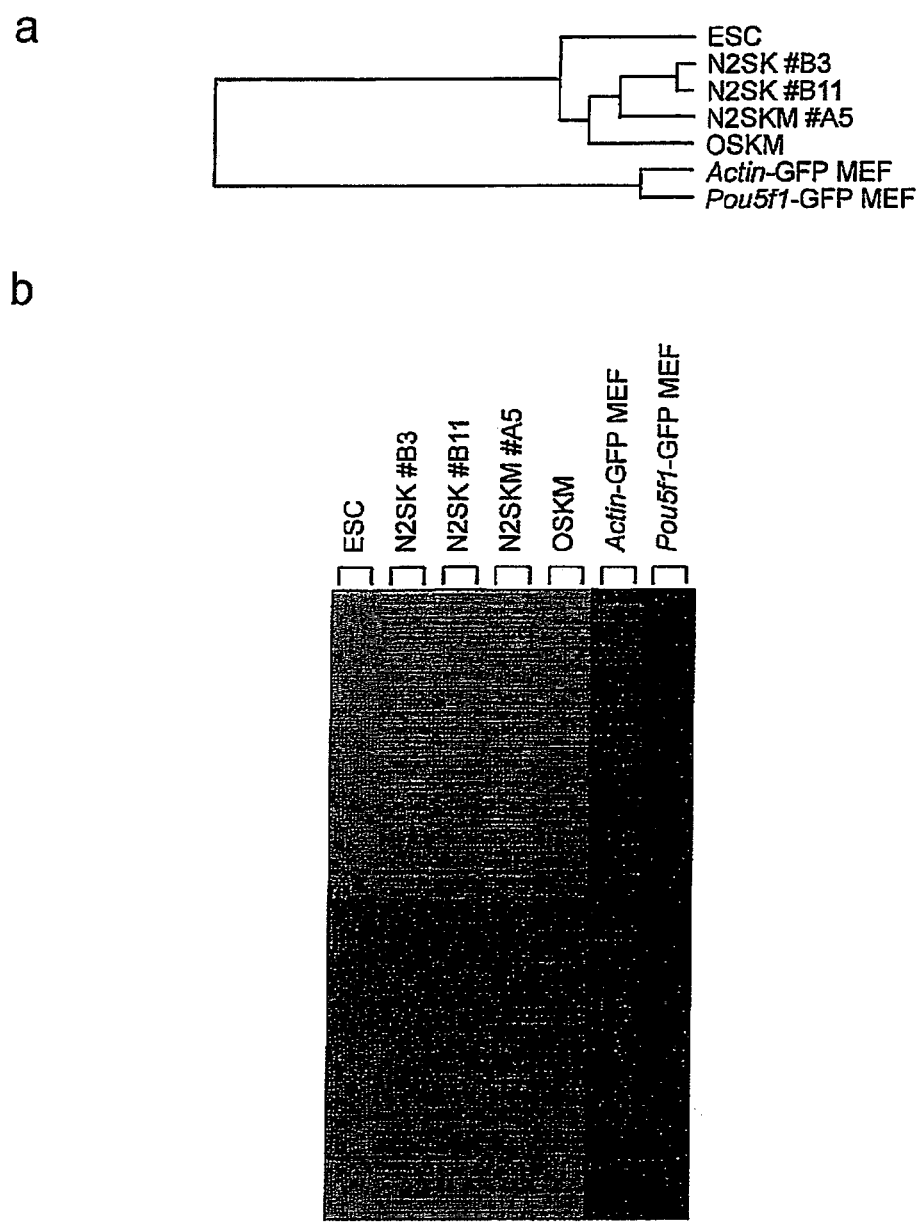
FIG. 2. Global expression profiling of Nr5a2-reprogrammed cells.
(a) Correlation analysis (46,643 probes) was carried out to cluster the transcriptome of ESCs, iPSCs (OSKM, $N_2SKM$ #A5, $N_2SK$ #B3 and $N_2SK$ #B11) and MEFs (actin-GFP and Pou5f1-GFP). OSKM iPSCs were derived from the retroviral introduction of Oct4, Sox2, Klf4 and c-Myc to MEFs.
(b) Heatmap generated from the biological replicate microarray data in a displays the expression profile of 1,000 ESC-associated and MEF-associated genes. Green represents downregulation of gene expression while red represents upregulation of gene expression with respect to MEFs.

Global gene expression profiling of Nr5a2-reprogrammed cells was performed to study if the genetic expression of these iPSCs was akin to ESCs. The transcriptome of Nr5a2-reprogrammed cell lines (N$_2$SKM and N$_2$SK) as well as MEFs (actin-GFP and Pou5f1-GFP), ESCs and an OSKM iPSC line were characterized. Cluster analysis revealed that Nr5a2-reprogrammed cells were more similar to ESCs and OSKM iPSCs than MEFs (FIG. 2a). In addition, the expression profiling showed a concomitant upregulation of ESC-associated genes and a downregulation of MEF-associated genes in Nr5a2-reprogrammed cells (FIG. 2b). Taken together, the expression profiles of Nr5a2-reprogrammed cells are similar to both ESC and conventional OSKM iPSCs.

Figure 3:
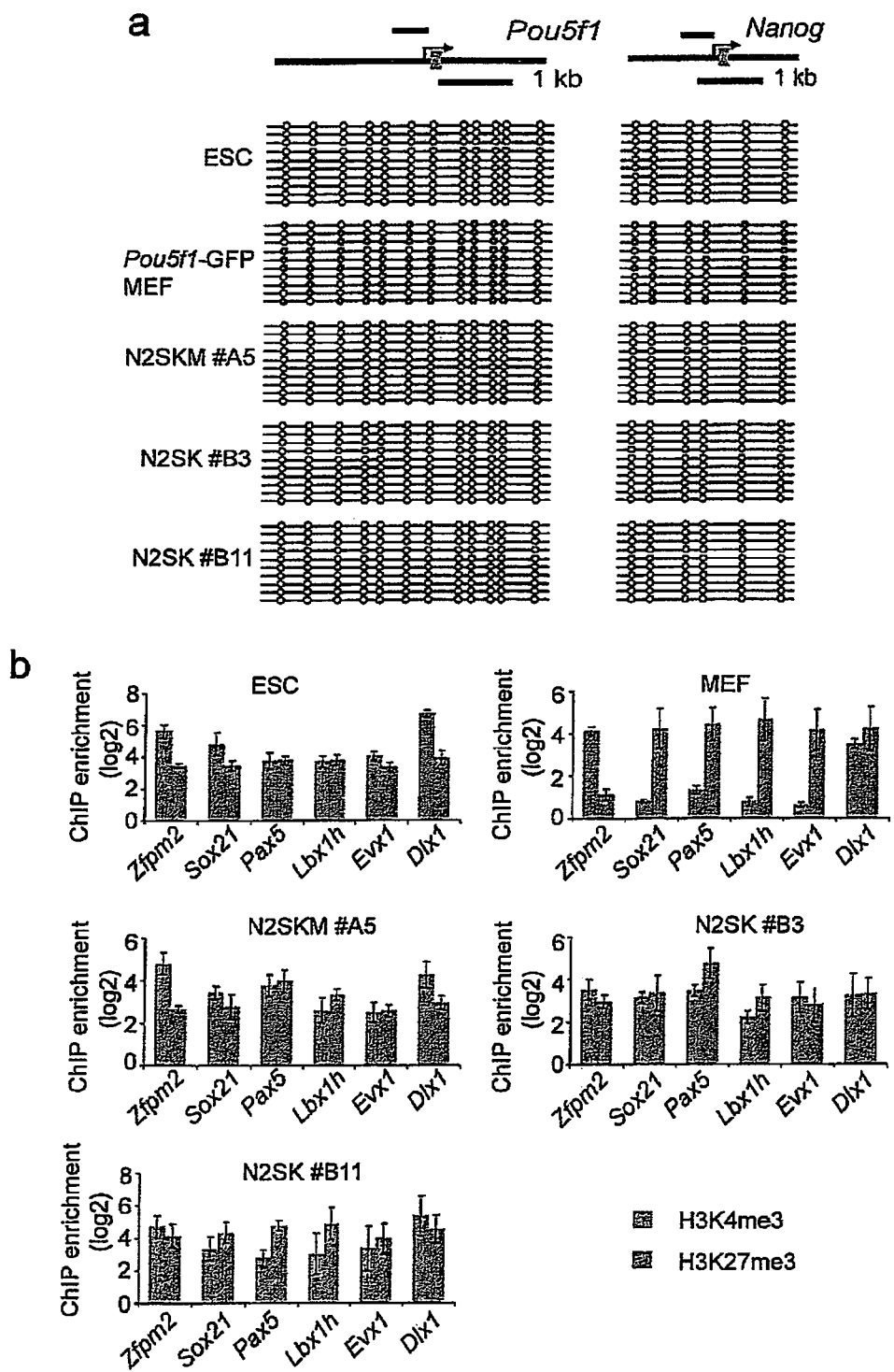
FIG. 3. Epigenetic states of Nr5a2-reprogrammed cells.
(a) Pou5f1 and Nanog promoter methylation analysis of Nr5a2-reprogrammed cells. Bisulphite genomic sequencing was performed to analyze the methylation status of the promoter region of Pou5f1 and Nanog in ESCs, MEFs and Nr5a2-reprogrammed cells ($N_2SKM$ #A5, $N_2SK$ #B3 and $N_2SK$ #B11). For each cell line, ten random clones were sequenced and the results are displayed in circles in which open circles represent unmethylated CpG dinucleotides while red circles represent methylated CpG dinucleotides.
(b) Bivalent chromatin marks in Nr5a2-reprogrammed cells. Following ChIP assay, quantitative real-time PCR was performed to analyze the enrichment of trimethylated histone H3K4 and H3K27 chromatin marks in ESCs, MEFs and Nr5a2-reprogrammed cells. Data represents $Log_2$ enrichment for reported bivalent gene loci (Zfpm2, Sox21, Pax5, Lbx1h, Evx1 and Dlx). Data shown are mean±s.e.m. of three independent experiments (n=3).

Next, bisulfite sequencing was performed to investigate the methylation status of the Pou5f1 and Nanog promoters in Nr5a2-reprogrammed cells. Promoter methylation analysis revealed that the Pou5f1 and Nanog promoters of Nr5a2-reprogrammed cells were largely unmethylated (FIG. 3a) and were similar to that of ESCs, whereas the Pou5f1 and Nanog promoter regions of MEFs were hypermethylated. We also explored the bivalent domain patterns of Nr5a2-reprogrammed cells. Our results showed that Nr5a2-reprogrammed cells possessed both active H3K4me3 and repressive H3K27me3 chromatin modifications on six genes (Zfpm2, Sox21, Pax5, Lbx1h, Evx1 and Dlx1) (FIG. 3b). These results are consistent with that of ESCs, which harbor both chromatin modifications, unlike differentiated cells which have resolved to either chromatin mark.

Figure 8:
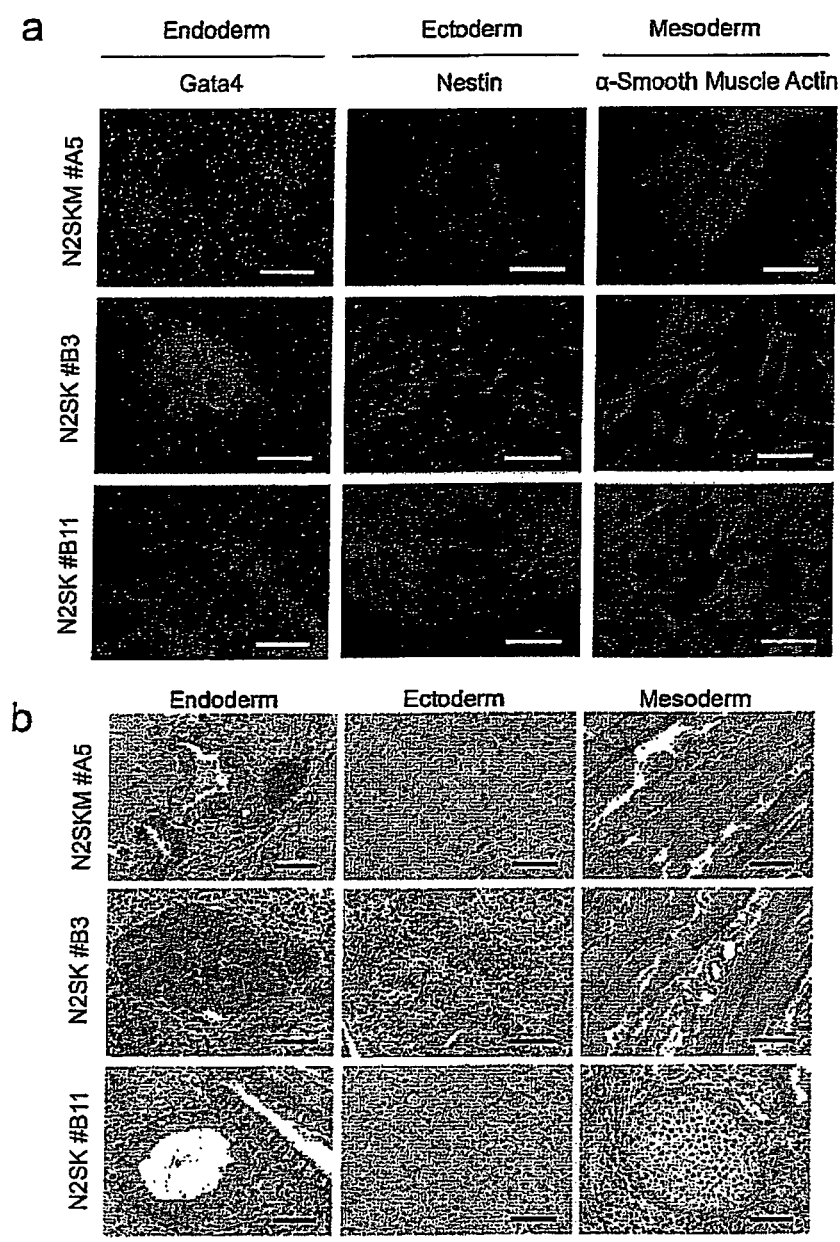
FIG. 8. Nr5a2-reprogrammed cells differentiate into lineages of the three major germ layers in the in vitro and in vivo differentiation assays.
(a) Embryoid body-mediated in vitro differentiation assay showed that Nr5a2-reprogrammed cells could differentiate into cells of the three major embryonic lineages. Cells differentiated from Nr5a2-reprogrammed cells stained positive for Gata-4 (endoderm), Nestin (ectoderm) and α-Smooth Muscle Actin (mesoderm). Differentiation markers were stained red and Hoechst dye counterstained the nuclei blue.
(b) Nr5a2-reprogrammed cells differentiated into tissues of the three primary germ layers in the teratoma assay. Teratomas sectioned and stained with Mallory's tetrochrome revealed ectodermal tissue (neural ectoderm), mesodermal tissue (muscle and cartilage) and endodermal tissue (gut epithelium and pancreatic cells). Scale bars represent 100 µm in a and 50 µm in b.

Both embryoid body (EB)-mediated differentiation and teratoma formation assays were carried out to test the pluripotency of the Nr5a2-reprogrammed cells. Nr5a2-reprogrammed cells were indeed pluripotent as they could be in vitro differentiated into cells of the three major germ layers (endoderm, ectoderm and mesoderm) (FIG. 8a) and form teratomas that consisted of differentiated tissue originating from the three major germ layers (FIG. 8b).

Figure 4:
FIG. 4. $N_2SK$ iPSCs can generate mouse chimeras.
(a) Brightfield image of the male gonad dissected from the E13.5 $N_2SK$ #B3 chimeric embryo.
(b) GFP fluorescence image of a. Positive GFP signals were observed in the gonads, indicating germline incorporation of the Nr5a2-reprogrammed cells.
(c) $N_2SK$ #B11 adult chimeras. Nr5a2-reprogrammed cells, derived from 129S2/SV Pou5f1-GFP MEFs were microinjected into B6(Cg)-Tyr$^{c-2J}$/J embryos and generated chimeras with mixed fur coat color.

A more stringent assay for pluripotency was performed whereby Nr5a2-reprogrammed cells were microinjected into 8-cell stage wild-type C57BL/6J or B6(Cg)-Tyr$^{c-2J}$/J (B6-albino) embryos. As the Nr5a2-reprogrammed cells were derived from Pou5f1-GFP MEFs, GFP expression should be observed in the gonads due to high levels of endogenous Oct4 expression in the gonads. As expected, E13.5 embryo displayed GFP-expression in the gonads (FIG. 4a-b). More importantly, live-born chimeras were generated from both N$_2$SKM (FIG. 6i) and N$_2$SK lines (FIG. 4c).

Characterisation of Cells Reprogrammed with Nr5a1

Figure 9:
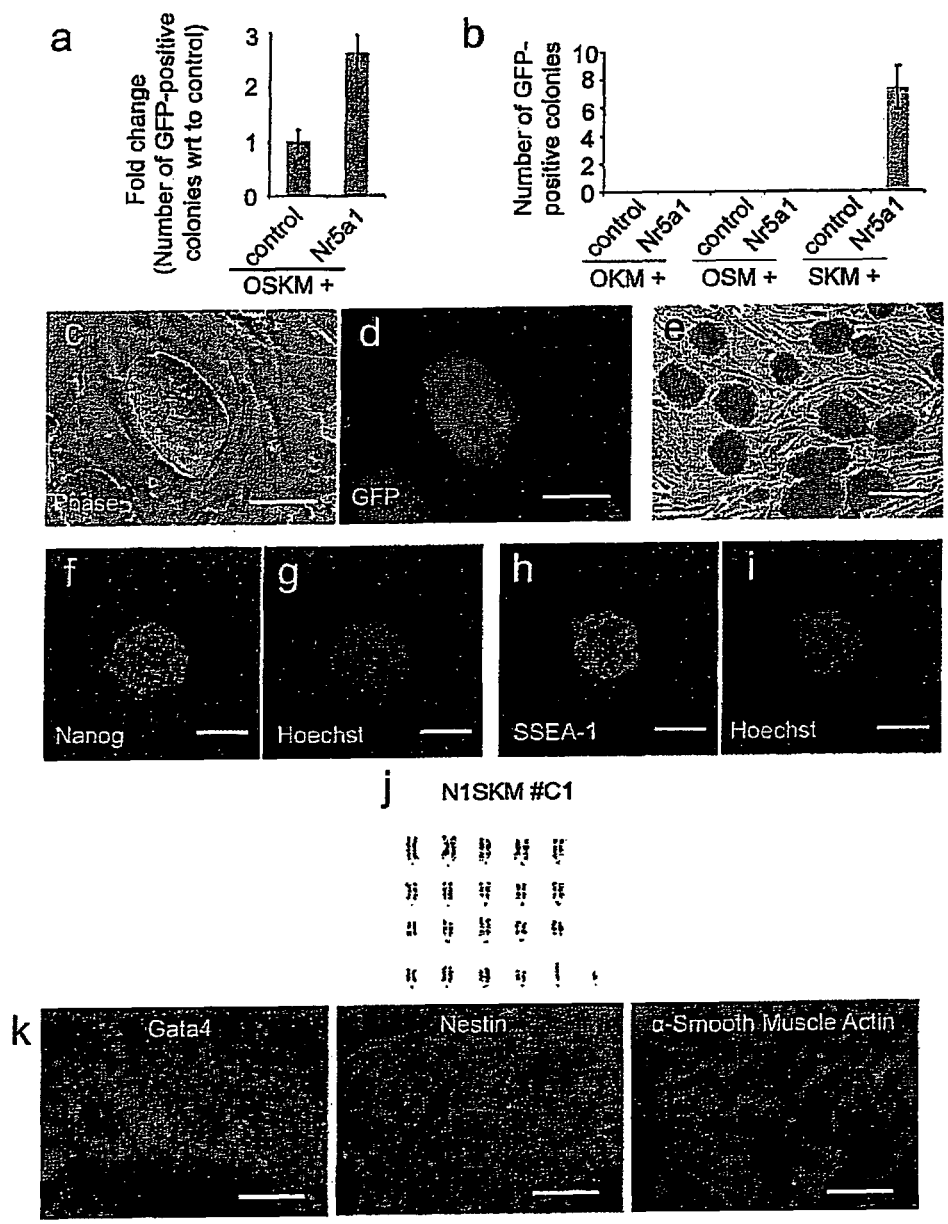
FIG. 9. Nr5a1 reprograms MEFs with Sox2, Klf4 and c-Myc.
(a) Nr5a1 enhances the efficiency of reprogramming with Oc4, Sox2, Klf4 and c-Myc. Graph depicts the fold change of number of Pou5f1-GFP-positive colonies generated from Nr5a1 in conjunction with OSKM with respect to the OSKM (control). Data represent mean±s.e.m. of three retrovirus-mediated transduction experiments (n=3).
(b) Nr5a1 replaces Oct4 in the reprogramming of MEFs. Nr5a1 was investigated for its ability to replace Sox2, Klf4 and Oct4 by co-transducing Nr5a1 in conjunction with OKM, OSM and SKM respectively. Control experiments were performed with OKM, OSM or SKM retroviruses in the absence of Nr5a1. Data represent mean±s.e.m. of three retrovirus-mediated transduction experiments (n=3).
(c) Phase contrast image of iPSC colonies generated from the retroviral transduction of Pou5f1-GFP MEFs with Nr5a1, Sox2, Klf4 and c-Myc.4
(d) Fluorescence image of Pou5f1-GFP-positive N1SKM iPSC colonies in c.
(e) Nr5a1-reprogrammed cells stained positive for alkaline phosphatase.
(f) Nanog was expressed in Nr5a1-reprogrammed cells
(g) Hoechst staining of f indicates nuclei.
(h) Nr5a1-reprogrammed cells stained positive for SSEA-1
(i) Cells in h were stained with Hoechst to indicate nuclei.
(j) Normal male karyotype of a Nr5a1-reprogrammed cell line
(k) Embryoid body-mediated in vitro differentiation assay performed on. Nr5a1-reprogrammed cells show that it can differentiate to cells of the three major embryonic lineages. Differentiated cells stained positive for Gata4 (endoderm), Nestin (ectoderm) and α-Smooth Muscle Actin (mesoderm). Lineage markers were stained red and nuclei were stained blue with Hoechst. Scale bars represent 200 um in c-e and 50 um in f-i.

Nr5a1, also known as steroidogenic factor 1 (Sf1), belongs to the same nuclear receptor subfamily 5 as Nr5a2. Hence, we were interested to examine if Nr5a1 was able to both enhance the efficiency of reprogramming and replace Oct4. Nr5a1 enhanced reprogramming efficiency (FIG. 9a) but to a lesser extent than Nr5a2. Next, we investigated if Nr5a1 could replace any of the core reprogramming factors (O, S and K). Similar to Nr5a2, Nr5a1 was unable to replace Sox2 and Klf4. Interestingly, MEFs transduced with Nr5a1 and SKM viruses generated Pou5f1-GFP positive iPSC colonies (FIG. 9b-d). We refer to these reprogrammed MEFs as N$_1$SKM iPSCs. These Nr5a1-reprogrammed cells express alkaline phosphatase (FIG. 9e), Nanog (FIG. 9f-g) and SSEA-1 (FIG. 9h-i). In addition, these karyotypically normal N$_1$SKM iPSCs (FIG. 9j) could be in vitro differentiated to lineages of the three different germ layers (FIG. 9k). The independent demonstration of reprogramming with Nr5a1 shows that both members of the Nr5a subfamily indeed possess similar reprogramming properties.

Figure 10:
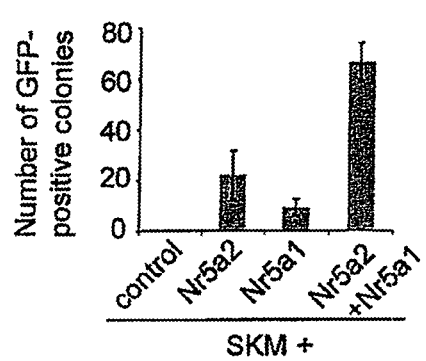
FIG. 10. Nr5a2 and Nr5a1 together boost reprogramming of MEFs with Sox2, Klf4 and c-Myc.Introduction of both Nr5a2 and Nr5a1 in conjunction with Sox2, Klf4 and c-Myc enhances the number of GFP-positive colonies generated as compared to when either Nr5a2 or Nr5a1 is transduced with SKM. Control experiment was the transduction of MEFs with only the SKM viruses. Data represent mean±s.e.m. of three retrovirus-mediated transduction experiments (n=3).

Next, we examined if the addition of both Nr5a2 and Nr5a1 would boost the efficiency of reprogramming without Oct4. Hence, Pou5f1-GFP MEFs were co-transduced with Nr5a2, Nr5a1 and SKM viruses. Interestingly, the addition of both Nr5a2 and Nr5a1 with SKM was able to increase the number of Pou5f1-GFP positive colonies by about 3-fold with respect to Nr5a2 and SKM (FIG. 10). This result shows that both factors indeed had an additive effective on reprogramming efficiency when introduced together.

Design of Nuclear Receptor Fragments

Figure 11:
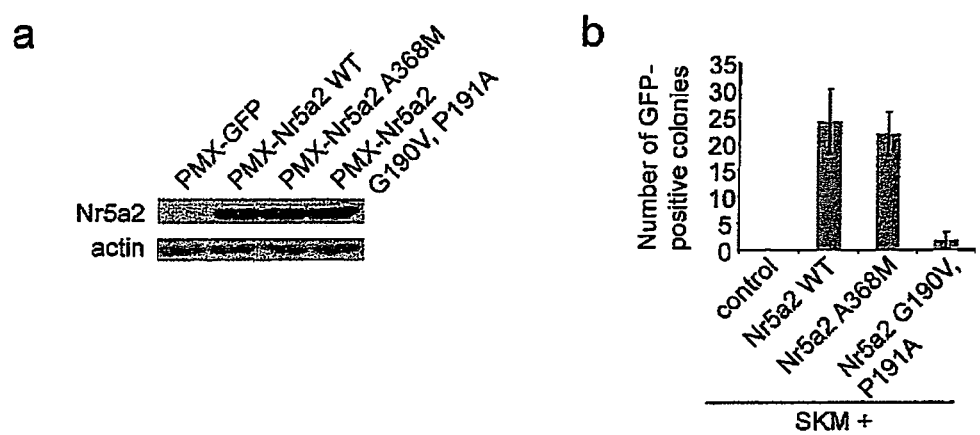
FIG. 11. DNA binding domain (DBD) is important for Nr5a2 to reprogram MEFs whereas ligand binding domain (LBD) of Nr5a2 is dispensable for its function as a reprogramming factor.
(a) Western analysis of cell extracts harvested from 293-T cells transfected with either retroviral vectors encoding Nr5a2 WT, Nr5a2 A368M (LBD mutant) and Nr5a2 G190V, P191A (DNA mutant) showed equal expression of Nr5a2 protein. 293-T cells transfected with retroviral vectors harboring the GFP gene was used as a negative control. Western blot of actin was performed as a loading control.
(b) Analysis of Nr5a2 mutants for ability to retain its function as a reprogramming factor. Pou5f1-GFP MEFs were transduced with SKM viruses and viruses encoding either Nr5a2 WT, Nr5a2 A368M or Nr5a2 G190V, P191A. Control experiment denotes infection of MEFs with only SKM viruses. Data represent mean±s.e.m. of three retrovirus-mediated transduction experiments (n=3).

Similar to other nuclear receptors, Nr5a2 possesses a ligand binding domain (LBD) and a DNA binding domain (DBD). However, being an orphan nuclear receptor, the endogenous ligands of Nr5a2 remains unknown. Unlike most nuclear receptors which function as dimers, Nr5a2 is able to bind DNA in its monomeric state. We investigated the functional importance of the LBD and DBD of Nr5a2 in the reprogramming of MEFs without Oct4. We mutated a specific residue to a bulkier residue (A368M) that fills the cavity of Nr5a2 LBD so as to disrupt the binding of putative ligands. Next, we created a DBD mutant with a double mutation (G190V, P191A) in the conserved Ftz-F1 domain that would result in a marked decrease in Nr5a2 DNA binding activity. A reprogramming assay was hence performed whereby Pou5f1-GFP MEFs transduced with SKM viruses were also transduced with viruses encoded with either wildtype (WT) Nr5a2, A368M Nr5a2 mutant or G190V, P191A Nr5a2 mutant. Western analysis was carried out to ensure that the retroviral vectors expressed equivalent level of Nr5a2 protein (FIG. 11a). Our results show that the Nr5a2 LBD mutant did not decrease the number of formed Pou5f1-GFP positive colonies as compared to the WT (FIG. 11b). This suggests that Nr5a2 functions as a reprogramming factor independent of ligand binding. In contrast, there was a dramatic reduction in the number of Pou5f1-GFP positive colonies when Nr5a2 DBD mutant was introduced with SKM (FIG. 11b). This shows that the integrity of Nr5a2 DBD is important for proper binding of the nuclear receptor to promoter/enhancer regions of target genes to initiate the reprogramming process in MEFs. Taken together, we show that the DBD is crucial for the reprogramming function of Nr5a2 while ligand binding is dispensable for its role in reprogramming.

Reprogramming with Nr5a2 or Nr5a1 is the first reported instance of transcription factors that are able to bypass the need for exogenous Oct4. Nr5a2 is responsible for the maintenance of Oct4 expression in early mouse embryonic development. Nr5a2 has been shown to be able to bind to both the proximal enhancer and proximal promoter regions of Pou5f1 and regulate Oct4 in the epiblast stage of mouse embryonic development. Hence, as an Oct4-regulator, exogenous Nr5a2 may be sufficient to induce endogenous Oct4 expression and substitute for exogenous Oct4 in the reprogramming process of MEFs. Although Nr5a1 is not expressed in mouse ESCs, it activates Oct4 expression in mouse embryonal carcinoma cells and this is consistent with its ability to replace Oct4 in reprogramming. In this regard, it is conceivable that factors which activate Oct4 expression may also replace Oct4 in the reprogramming process. Sall4 is a known transcriptional regulator of Oct4. However, when Sall4 retrovirus was introduced with SKM viruses no Pou5f1-GFP positive colonies were observed (data not shown). Hence, it is noteworthy that not all Oct4 regulators are able to replace Oct4 in the generation of iPSCs.

In summary, our study provides an Oct4-independent code for reprogramming of somatic cells. In addition, we also show that both Nr5a2 and Nr5a1 are able to enhance the efficiency of reprogramming with the conventional four factors. Altogether, we have uncovered an unexpected dual role of nuclear receptor s in both enhancing and mediating reprogramming.

Methods

Cell culture and transfection. iPSCs were cultured on mitomycin C-treated MEF feeders in Dulbecco's modified Eagle medium (DMEM; Gibco), supplemented with 15% heat-inactivated fetal bovine serum (FBS; Gibco) or 15% knockout serum replacement (KSR; Gibco), 0.055 mM β-mercaptoethanol (Gibco), 2 mM L-glutamine (Gibco), 0.1 mM MEM non-essential amino acid (Gibco), 20 μg ml$^{-1}$ gentamicin (Gibco) and 1000 U ml$^{-1}$ of LIF (homemade) and passaged every 2-3 days. MEFs were isolated from E13.5 embryos and cultured as described previously[7]. 293-T cells on 10 cm plates were transfected with 25 μg of each PMX retroviral vector using Lipofectamine 2000 (Invitrogen) according to the manufacturer's instructions.

Mouse molecular genetics. MEFs were isolated from Pou5f1-GFP transgenic mice and actin-GFP transgenic mice (Jackson's lab, stock no. 004654 and 003516). Pou5f1-GFP and actin-GFP MEFs were harvested from E13.5 embryos derived from the intercross between male Pou5f1-GFP male mice and female wild-type 129S2/SV and the intercross between actin-GFP mice and female wild type CD1 mice, respectively. 8-12 iPSCs were microinjected into C57BL/6J and B6(Cg)-Tyr$^{c-2J}$/J embryos that were obtained at the 8-cell stage. Microinjected embryos were transferred to the oviduct of E0.5 pseudopregnant F1 (CBA×C57BL/6J) females. Chimeric embryos were harvested at E13.5 and assayed for GFP expression in the gonads with a fluorescence microscope.

Retrovirus packaging and infection. cDNA sequences of Nr5a2 and other factors were PCR amplified from either mouse ESC cDNA or commercial plasmids (Open Biosystems). Nr5a2 mutants were PCR amplified with the appropriate primers. Amplified coding sequences were verified by sequencing and cloned into. MMLV-based pMXs retroviral vector. Retroviruses were generated as described previously[1]. For iPSC generation, equal amounts of viruses encoding the different factors were introduced to MEFs at 70% confluence in DMEM containing 15% FBS and 6 ng ml$^{-1}$ polybrene. At 1 dpi, medium was changed to fresh MEF medium. At 2 dpi, cells were passaged to MEF feeders and cultured for 6 days in culture medium containing FBS as described previously followed by an additional 5-15 days in culture medium containing KSR as described previously.

RNA extraction, reverse transcription and quantitative real-time PCR. As described above.

Bisulphite genomic sequencing. Genomic DNA was bisulphite-treated with the Imprint™ DNA modification kit (Sigma) according to the manufacturer's instructions. Promoter regions of Pou5f1 and Nanog were amplified by PCR and cloned into the pCR2.1-TOPO vector (Invitrogen) and sequenced with the M13 forward and M13 reverse primers.

Primer sequences used in the PCR amplification of the Pou5f1 and Nanog promoter regions are
5'-ATGGGTTGAAATATTGGGTTTATTTA (SEQ ID NO: 11),
5'CCACCCTCTAACCTTAACCTCTAAC (SEQ ID NO: 12) and
5'-GATTTTGTAGGTGGGATTAATTGTGAATTT (SEQ ID NO: 13),
5'-ACCAAAAAAACCCACACTCATATCAATATA (SEQ ID NO: 14) respectively.

Karyotyping. iPSCs were treated with colcemid (Invitrogen) and harvested by standard hypotonic treatment and fixed with methanol:acetic acid (3:1). Slides were air-dried before G-band karyotyping.

Genotyping. Each PCR amplification reaction was performed with 300 ng of genomic DNA harvested from either iPSCs, ESCs, MEFs or embryo.

```
Sense primer sequence:
                                    (SEQ ID NO: 15)
5'-GACGGCATCGCAGCTTGGATACAC.

Antisense primer sequences are:
Nr5a2:
                                    (SEQ ID NO: 16)
5'-GACGCAATAGCTGTAAGTCCATG;

Sox2:
                                    (SEQ ID NO: 17)
5'-GCTTCAGCTCCGTCTCCATCATGTT;

Klf4:
                                    (SEQ ID NO: 18)
5'-GCCATGTCAGACTCGCCAGG;

c-Myc:
                                    (SEQ ID NO: 19)
5'-TCGTCGCAGATGAAATAGGGCTG;
and Oct4:
                                    (SEQ ID NO: 20)
5'-CCAATACCTCTGAGCCTGGTCCGAT.
```

EB-mediated in vitro differentiation. For EB formation, iPSCs were trypsinized and cultured in Petri-dish for 4-5 days in iPSC culture medium in the absence of LIF and β-mercaptoethanol. EBs were transferred to gelatin-coated plates and cultured for 5-6 days with the addition of 1 μM retinoic acid (Sigma). Samples were fixed in 4% paraformaldehyde, permeabilized with 1% triton X-100, blocked with 8% FBS, and stained with anti-Gata-4 (1:100, sc-25310, Santa Cruz), anti-Nestin (1:100, sc-58813, Santa Cruz) or anti-α-Smooth Muscle Actin (1:100, ab18460, Abcam). Samples were then stained with the secondary antibody, Alexa Fluor 546 conjugated anti-mouse (1:1000, Invitrogen) followed by staining of the nuclei with Hoechst (1:4000, Invitrogen).

Teratoma assay. iPSCs were harvested by trypsinization and resuspended to a concentration of $1 \times 10^7$ cells ml$^{-1}$ in 0.9% saline. 100 μl of the cell suspension was injected subcutaneously into each dorsal flank of avertin-anesthetized SCID mice. Teratomas were dissected after 3-4 weeks, weighted and fixed in Bouin's solution, before embedding in parafilm. Parafilm-embedded tissue was sectioned and stained with Mallory's Tetrachrome as previously described[26].

Immunofluorescence microscopy and alkaline phosphatase staining. iPSCs cultured on gelatin-coated cover slips were fixed with 4% paraformaldehyde, permeabilized in 1% triton X-100, blocked with 8% FBS. After blocking, samples were stained with anti-Nanog (1:50, RCAB0002PF, CosmoBio) or anti-SSEA-1 (1:200, MAB4301, Chemicon), before staining with Alexa Fluor 568 conjugated anti rabbit (1:300, Invitrogen) or Alexa Fluor 546 conjugated anti-mouse IgM (1:2000, Invitrogen), respectively. Nuclei were then counterstained with Hoechst (Invitrogen). Alkaline phosphatase detection was performed using a commercial ESC characterization kit (Chemicon).

Western analysis. After 48 h transfection, 293-T cells were lysed with RIPA buffer (Pierce) supplemented with protease inhibitor cocktail (Roche). Protein concentration was measured with a Bradford assay kit (Bio-Rad). 50 μg of cell lysate was resolved on a 10% SDS-polyacrylamide gel and transferred to a polyvinylidine difluoride membrane (Millipore). The membrane was blocked with 5% skim milk. After blocking, the blot was incubated with either anti-Nr5a2 (1:2000, ab18293, Abcam) or anti-actin (1:2000, sc-1616, Santa-Cruz) primary antibodies for 1 h, washed with PBST and incubated with either horse-radish peroxidase (HRP)-conjugated anti-rabbit IgG (1:5000, sc-2004, Santa Cruz) or HRP-conjugated anti-goat IgG (1:5000, sc-2768, Santa Cruz), respectively. After washing with PBST, signals were detected using the Western Blotting Luminol Reagents (Santa Cruz).

ChIP assay. ChIP assays were performed as described previously[27]. In short, cells were crosslinked with 1% formaldehyde for 10 min at room temperature and the formaldehyde was quenched with 125 mM glycine. Cell lysates were sonicated and chromatin extracts were immunoprecipitated with anti-H3K4me3 (ab8580, Abcam) or anti-H3K27me3 (07-449, Millipore) antibodies. Quantitative PCR analyses were performed as previously described[7].

Microarray analysis. Reverse transcription of mRNAs harvested from mouse ESCs, iPSCs (OSKM, N$_2$SKM #A5, N$_2$SK #B3 and #B11) and MEFs (actin-GFP and Pou5f1-GFP) was performed. Two biological replicate microarray data was generated for each cell line. Arrays (Sentrix Mouse-6 Expression BeadChip version 1.1) processed according to the manufacturer's instructions were scanned with the Illumina microarray platform. Differentially expressed genes were selected based on Significance Analysis of Microarrays (SAM) criteria: fold change (FC)<0.6 for downregulated, FC>1.5 for upregulated; q value<2%; and detection probability greater than 0.95 in all samples.

Figure 12:
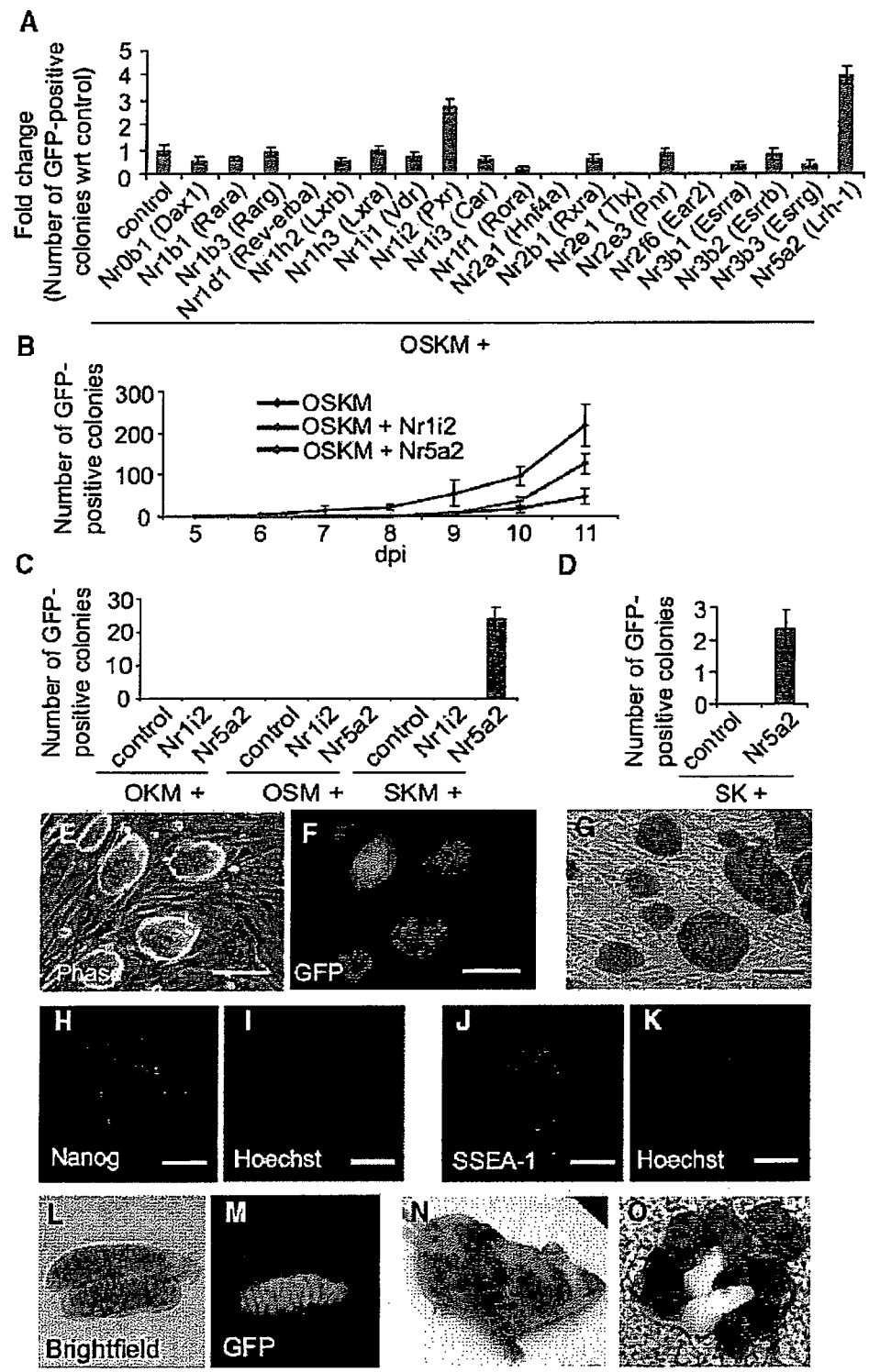
FIG. 12. Nr5a2 reprograms MEFs with Sox2, Klf4 and with or without c-Myc
(A) Screen of 19 nuclear receptors for the enhancement of OSKM reprogramming. Graph depicts fold change of number of GFP-positive colonies generated from each nuclear receptor together with OSKM with respect to OSKM (control).
(B) Kinetics of OSKM reprogramming with either Nr5a2 or Nr1i2.
(C) Reprogramming assay of reprogramming enhancers Nr1i2 and Nr5a2 for their ability to replace Sox2, Klf4 and Oct4. For control experiments, the respective combinations of retroviruses were added without Nr5a2 or Nr1i2.

Screen of Nuclear Receptors Reveals that Nr1i2 and Nr5a2 can Enhance Reprogramming Efficiency We carried out a screen of 19 nuclear receptors (Table 1) for their ability to enhance reprogramming efficiency. MEFs containing a Pou5f1-GFP reporter (FIG. 12A) (Feng et al., 2009a) were used to identify putative iPSC colonies, based on the reactivation of the Pou5f1 gene. We transfected each nuclear receptor retrovirally along with Oct4 (O), Sox2 (S), Klf4 (K), and c-Myc (M) retroviruses. The frequency of GFP-positive colonies was determined at 14 days post infection (dpi). Transcript expression of all the nuclear receptor constructs was verified (data not shown). From this screen, we found that both orphan nuclear receptors, Nr1i2 (also known as pregnane X receptor, Pxr) and Nr5a2 (also known as liver receptor homolog-1, Lrh-1), can enhance the efficiency of reprogramming (as compared to OSKM control) by 2.7 and 4.0-fold, respectively (FIG. 12A). Addition of Nr5a2 also enhanced the kinetics of OSKM reprogramming with GFP expression detectable three days earlier than in the case of conventional four factor reprogramming (FIG. 12B). Cell viability assays confirmed that both Nr1i2 and Nr5a2 do not induce cell death (FIG. 16B).

Nr5a2 can Replace Oct4 in the Reprogramming of MEFs to iPSCs

We next investigated if Nr1i2 and Nr5a2 could replace the core reprogramming factors in addition to enhancing reprogramming efficiencies. As c-Myc has already been demonstrated to be dispensable for reprogramming (Nakagawa et al., 2008; Wernig et al., 2008), we did not investigate the replaceability of c-Myc but instead tested the ability of these two nuclear receptors in replacing any of the OSK trio. Nr1i2 was unable to replace O, S or K, and Nr5a2 was unable to replace S or K (FIG. 12C). Strikingly, when Pou5f1-GFP MEFs were transduced with Nr5a2 and SKM viruses, GFP-positive colonies (23.7±3.5 per 100,000 MEFs plated) were observed by 14 dpi (FIG. 12C; FIGS. 16C and 16D). This demonstrates that besides augmenting reprogramming efficiency, exogenous Nr5a2 could also replace exogenous Oct4. We refer to these cells that have been reprogrammed with Nr5a2, Sox2, Klf4 and c-Myc as N₂SKM iPSCs. These colonies could be stably passaged long-term and stained positive for alkaline phosphatase (FIG. 16E), Nanog (FIGS. 16F and 16G) and SSEA-1 (FIGS. 16H and 16I). The other 18 nuclear receptors were also tested for their ability to replace Oct4. However, unlike Nr5a2, none were able to replace Oct4 (FIG. 16J).

Given that c-Myc is dispensable for reprogramming, we were also able to generate iPSCs from Pou5f1-GFP MEFs that were transduced with Nr5a2 and SK viruses, albeit at a lower efficiency (2.3±0.6 per 100,000 MEFs plated) than that of N₂SKM combination (FIGS. 12D-12F). These three-factor Nr5a2-reprogrammed cells are referred to as N₂SK iPSCs. Similar to N₂SKM iPSCs, N₂SK iPSCs stained positive for alkaline phosphatase (FIG. 12G), Nanog (FIGS. 12H and 12I) and SSEA-1 (FIGS. 12J and 12K).

Nr5a2-reprogrammed cells were karyotypically normal (FIG. 16K) and genomic integrations of the respective viruses into the genomic DNA were verified and showed no evidence of Oct4 transgene integration (FIG. 16L). Both embryoid body-mediated differentiation and teratoma formation assays were carried out to test the pluripotency of the Nr5a2-reprogrammed cells. Nr5a2-reprogrammed cells were indeed pluripotent as they could be in vitro differentiated into cells of the three major germ layers (FIG. 17A) and form teratomas that consisted of differentiated tissue originating from the three major germ layers (FIG. 17B).

A more stringent assay for pluripotency was performed whereby Nr5a2-reprogrammed cells were microinjected into 8-cell stage wild-type C57BL/6J or B6(Cg)-Tyr$^{c-2J}$/J (B6-albino) embryos. As the Nr5a2-reprogrammed cells were derived from Pou5f1-GFP MEFs, E13.5 embryos displayed GFP expression in the gonads due to high levels of endogenous Oct4 expression (FIGS. 12L and 12M). In addition, live-born chimeras were generated from both N₂SKM (FIG. 16M) and N₂SK lines (FIG. 12N). More importantly, the N₂SK line is germline competent (FIG. 12O, Table 2).

TABLE 2

Pluripotency assays of Nr5a2-reprogrammed cells.

| Lines | #A5 (N₂SKM) | #B3 (N₂SK) | #B11 (N₂SK) |
|---|---|---|---|
| EB formation | yes | yes | yes |
| EB differentiation to cells of three germ | yes | yes | yes |
| Teratoma formation consisting of tissues from three germ | yes | yes | yes |
| Gonad incorporation | yes | yes | yes |
| Chimaeras | yes | yes | yes |
| Germline transmission | no | no | yes |

Table Legend
yes denotes iPSC line passing assay and no denotes no germline transmission was observed.
Expression and epigenetic profiling of Nr5a2-reprogrammed cells closely resemble ESCs Global gene expression profiling of Nr5a2-reprogrammed cells was performed and hierarchical clustering of the microarray data revealed that Nr5a2-reprogrammed cells were more similar to ESCs and OSKM iPSCs than MEFs (FIG. 17C). In addition, expression profiling showed a concomitant upregulation of ESC-associated genes and a downregulation of MEF-associated genes in Nr5a2-reprogrammed cells (FIG. 17D).

Next, promoter methylation analysis revealed that the Pou5f1 and Nanog promoters of Nr5a2-reprogrammed cells were largely unmethylated (FIG. 17E) and were similar to that of ESCs. We also explored the bivalent domain patterns of Nr5a2-reprogrammed cells. Our results indicated that Nr5a2-reprogrammed cells possessed both active H3K4me3 and repressive H3K27me3 chromatin modifications (FIG. 17F) which were similar to that of ESCs.

The Close Family Member Nr5a1 can Also Enhance Reprogramming Efficiency and Replace Oct4

Closely related members of the same family of transcription factors can replace each other in the context of reprogramming (Feng et al., 2009a; Nakagawa et al., 2008). As both Nr5a1 (also known as steroidogenic factor 1, Sf1) and Nr5a2 belong to the same nuclear receptor subfamily V, we were interested to examine if Nr5a1 was able to both enhance the efficiency of reprogramming and replace Oct4. Nr5a1 enhanced reprogramming efficiency (FIG. 13A) but to a lesser extent than Nr5a2 (FIG. 12A). Next, we investigated if Nr5a1 could replace any of the core reprogramming factors (O, S and K). Similar to Nr5a2, Nr5a1 was unable to replace S and K but it was able to replace Oct4 (FIG. 13B). We refer to these GFP-positive iPSC colonies (FIGS. 13C and 13D) as N₁SKM iPSCs. These Nr5a1-reprogrammed cells express alkaline phosphatase (FIG. 13E), Nanog (FIGS. 13F and 13G) and SSEA-1 (FIGS. 13H and 13I). We verified the genomic integration of viral Nr5a1 in N₁SKM iPSCs and found no evidence of viral Pou5f1 and viral Nr5a2 genomic integrations (FIG. 13J). These karyotypically normal N₁SKM iPSCs (FIG. 13K) could be differentiated in vitro to lineages of the three different germ layers (FIG. 13L) and form teratomas comprising tissues of the three different lineages (FIG. 13M). The demonstration of reprogramming with Nr5a1 shows that both members of the Nr5a subfamily indeed possess similar reprogramming properties.

Other Transcription Factors that Bind Pou5f1 Regulatory Regions are Unable to Replace Exogenous Oct4 in Reprogramming Nr5a2 has been shown to bind both the proximal enhancer and proximal promoter regions of Pou5f1 and regulate Pou5f1 in the epiblast stage of mouse embryonic development (Gu et al., 2005). Nr5a2-null embryos display a loss of Oct4 expression in the epiblasts (Gu et al., 2005) and die between E6.5 and E7.5 (Gu et al., 2005; Pare et al., 2004). Therefore, part of the mechanism of Nr5a2 in replacing exogenous Oct4 may be explained by the findings that Nr5a2 directly regulates Pou5f1 and acts upstream of Pou5f1.

We went on to investigate if other transcription factors that bind to the Pou5f1 promoter or enhancer region could also replace Oct4 in the reprogramming of MEFs. Hence, we tested nine other transcription factors (Nanog, Sall4, Stat3, Zfx, Tcfcp2l1, Klf2, Klf5, N-Myc, Esrrb) that bind to the Pou5f1 regulatory regions (Chen et al., 2008). Expression of the respective viral transcripts was verified (FIG. 13N). Our results revealed that none of these transcription factors was able to replace Oct4 in the SKM combination (FIG. 13O). This result shows that not all transcription factors that bind to the Pou5f1 regulatory regions can replace Oct4 in reprogramming. Hence, Nr5a2 and its close family member, Nr5a1 are unique in their ability to replace Oct4.

DNA Binding Ability of Nr5a2 is Important for its Role in Reprogramming Whereas Ligand Binding is Less so Similar to other nuclear receptors, Nr5a2 possesses a ligand binding domain (LBD) and a DNA binding domain (DBD). However, being an orphan nuclear receptor, the endogenous ligands of Nr5a2 remain unknown. We investigated the functional importance of ligand binding and DNA binding of Nr5a2 in reprogramming without Oct4. We mutated a specific residue to a bulkier residue (A368M) that fills the cavity of Nr5a2 LBD so as to disrupt the binding of putative ligands (Sablin et al., 2003). Next, we created a DNA binding mutant with a double mutation (G190V, P191A) in the conserved Ftz-F1 domain that would result in a marked decrease in the DNA binding activity of Nr5a2 (Solomon et al., 2005). Western analysis was performed to ensure that these retroviral vectors expressed equivalent levels of Nr5a2 protein (FIG. 13P). Our reprogramming assays show that the Nr5a2 ligand binding mutant did not decrease the number of formed GFP-positive colonies as compared to wildtype (WT) Nr5a2 (FIG. 13Q). This suggests that the ability of Nr5a2 to function as a reprogramming factor is independent of ligand binding. In contrast, there was a dramatic reduction in the number of GFP-positive colonies when the Nr5a2 DNA binding mutant was introduced with SKM (FIG. 13Q). Taken together, we show that the DNA binding is crucial for the reprogramming function of Nr5a2 whereas ligand binding is dispensable.

Nr5a2 Sumoylation Site Mutants Exhibit Enhanced Reprogramming Capacity

We tested the reprogramming capacity of Nr5a2 with mutated lysine residues, using a mutant construct with two lysine residues mutated (2KR) and another with five lysine residues mutated (5KR). Western analysis showed that the WT and mutant constructs expressed similar levels of protein (FIG. 13R). Strikingly, the OSKM reprogramming assay revealed that the 2KR mutant boosted reprogramming efficiency to at least 7-fold as compared to the 4-fold enhancement achieved by the WT (FIG. 13S). When the 5KR mutant was introduced, reprogramming efficiency was further augmented to almost 11-fold (FIG. 13S). These results suggest that the concomitant prevention of subcellular localization and the enhanced transcriptional activity brought about by the SUMO site mutations could trigger a greater induction of reprogramming by Nr5a2.

Genome-Wide Binding Analysis of Nr5a2 in ESCs

Other than Pou5f1 (Gu et al., 2005), there is no known target gene for Nr5a2 in pluripotent cells. To this end, we performed a genome-wide mapping study of Nr5a2 in ESCs by employing chromatin immunoprecipitation sequencing (ChIF'-seq) technology (Table 3). We created a stable ESC cell line expressing HA-tagged Nr5a2 and the expression of HA-tagged Nr5a2 protein was verified by western blot using a Nr5a2-specific antibody (FIG. 18A). Nr5a2-bound chromatin was enriched with an anti-HA-tag antibody. We used the de novo motif discovery algorithm MEME and uncovered a known Nr5a2 motif enriched in our dataset (FIG. 14A). More importantly, our pairwise co-occurrence analyses revealed that Nr5a2 tends to co-localize with Nanog, Oct4, Sox2, Smad1 and Esrrb (FIG. 14B). This result associates Nr5a2 with the previously reported Nanog-Oct4-Sox2 cluster (Chen et al., 2008). As Nr5a2 works in concert with Sox2 and Klf4 to reprogram MEFs to iPSCs, we investigated if these three transcription factors share similar binding targets. Interestingly, we found that all three transcription factors bind target genes that are pivotal for maintenance of ESC identity such as Pou5f1, Nanog, Tbx3, Klf2 and Klf5 (FIG. 14C; FIG. 18B).

Nanog is a Target of Nr5a2

Nanog is important in ESCs as it governs the gateway to a ground state level of pluripotency (Silva et al., 2009). To confirm that Nanog is a target of Nr5a2 during reprogramming, we introduced exogenous HA-tagged Nr5a2 into MEFs. ChIP experiment showed that Nr5a2 was indeed bound to the Nanog enhancer during reprogramming (FIG. 15A). As Nanog is a target of Nr5a2 in both ESCs and MEFs (FIG. 18B; FIG. 15A), we investigated the role of Nanog in the context of reprogramming that involves Nr5a2. We found that Nanog expression increases when Nr5a2 was introduced to reprogramming MEFs (FIG. 4B). As expected, endogenous Pou5f1 increases in a similar trend as Nanog when Nr5a2 is introduced with OSKM during reprogramming (FIGS. 15C and 15D). As Nanog is important in the transition towards the pluripotent state (Silva et al., 2009), the enhancement of reprogramming efficiency brought about by the introduction of Nr5a2 may be in part facilitated by Nanog.

Next, we wanted to know if Nr5a2 was important in the reprogramming of MEFs. We performed a knockdown of Nr5a2 concurrently with the introduction of OSKM to MEFs. The Nr5a2 shRNA knockdown construct was able to reduce the Nr5a2 mRNA and protein expression in mouse ESCs (FIGS. 15E and 15F). Depletion of Nr5a2 during reprogramming resulted in a reduction in the number of colonies (FIG. 15G). Importantly, exogenous Nanog was able to rescue the reduction of colonies caused by the knockdown of Nr5a2 (FIG. 15G). Unlike Nanog, Mtf2, an independent factor was not able to rescue the reduction in colonies (FIG. 15G). Though Nanog was able to rescue the reduction in reprogramming efficiency brought about by Nr5a2 knockdown, Nanog was unable to rescue the effects of Pou5f1 knockdown (FIG. 15G). Interestingly, addition of both Nanog and Nr5a2 with OSKM was able to produce more GFP-positive colonies than Nr5a2 alone with OSKM (FIG. 15H). Taken together, these results suggest that Nanog is one of the important downstream targets of Nr5a2 in the reprogramming of MEFs in which it mediates the enhancement of reprogramming efficiency.

Herein, we show that reprogramming with Nr5a2 or Nr5a1 is able to bypass the need for exogenous Oct4. Our data indicate that Nr5a2 functions synergistically with Sox2 and Klf4 to replace exogenous Oct4 to mediate the successful reprogramming of MEFs. Other than MEFs, we were also able to reprogram mouse NPCs with exogenous Nr5a2 together with Klf4 and c-Myc (data not shown). Besides being an upstream activator of Pou5f1 (Gu et al., 2005), Nr5a2 also works in part through Nanog, an important mediator of ground state pluripotency in ESCs (Silva et al., 2009), and Nanog induction by Nr5a2 facilitates the acquisition of pluripotency. Recently, it was found that chemicals that inhibit Tgf-β signaling (Ichida et al., 2009; Maherali and Hochedlinger, 2009) induces Nanog to replace exogenous Sox2 in the reprogramming of MEFs (Ichida et al., 2009). Hence, Nanog is indeed an important target of reprogramming.

In summary, our study provides an example of exogenous Oct4-free code for the reprogramming of somatic cells. We also show that both Nr5a2 and Nr5a1 are able to enhance the efficiency of reprogramming with the conventional four factors. Altogether, we have uncovered an unexpected dual role of nuclear receptors in both enhancing and mediating reprogramming.

Cell Culture and Transfection iPSCs were cultured on mitomycin C-treated MEF feeders as previously described (Feng et al., 2009a). MEFs were isolated from E13.5 embryos and cultured as described previously (Feng et al., 2009a). 293-T cells were transfected with each pMX retroviral vector using Lipofectamine 2000 (Invitrogen) according to the manufacturer's protocol. For RNAi experiments, shRNA constructs that were cloned into the pSUPER.puro vector were transfected with lipofectamine into ESCs. Cells were selected with 1 μg ml⁻1 of puromycin 16 h post-transfection. shRNA sequences are Pou5f1: 5' -GAAGGATGTGGTTCGAGTA-3' (SEQ ID NO: 21), luciferase: 5'-GATGAAATGGGTAAGTACA -3' (SEQ ID NO: 22), and Nr5a2: 5' GCAAGTGTCTCAATT-TAAA-3' (SEQ ID NO: 23).

ChIP-Seq Analysis

Peak calling of the Nr5a2 ChIP-seq data (8,023 427 uniquely mapped tags) was carried out using MACS with a p value cutoff of 1e-9 and 3,346 peaks were generated. The control anti-HA ChIP-seq library contained 13,001,272 uniquely mapped tags. Enriched motifs were identified by the de novo motif discovery tool MEME using 200-bp sequences centered on the ChIP-seq peaks. Co-occurrence analysis to study overlap of Nr5a2 binding sites with binding sites of other important transcription factors was performed with Nr5a2 ChIP-seq data and data set generated from our previous study (Chen et al., 2008).

Microarray Analysis

Reverse transcription of mRNA harvested from mouse ESCs, iPSCs (OSKM, N₂SKM #A5, N₂SK #B3 and #B11) and MEFs (actin-GFP and Pou5f1-GFP) was performed. Two biological replicate microarray data was generated for each cell line. For microarray of OSKM+Nr5a2 and OSKM samples, biological triplicates were used. Arrays (Sentrix Mouse-6 Expression BeadChip version 1.1) processed according to the manufacturer's instructions were scanned with the Illumina microarray platform. Differentially expressed genes were selected based on Significance Analysis of Microarrays criteria: fold change (FC)<0.6 for downregulated, FC>1.5 for upregulated; q value<0.02; and detection probability greater than 0.95 in all samples.

GEO Accession Codes

Microarray and ChIP-seq data are accessible at the GEO database under accession numbers GSE19023 and GSE19019, respectively.

Mouse Molecular Genetics

MEFs were isolated from Pou5f1-GFP transgenic mice and actin-GFP transgenic mice (JAX laboratory, stock no. 004654 and 003516). Pou5f1-GFP and actin-GFP MEFs were harvested from E13.5 embryos derived from the intercross between male Pou5f1-GFP male mice and female wild-type 129S2/SV and the intercross between actin-GFP mice and female wild type CD1 mice, respectively. 8-12 iPSCs were microinjected into C57BL/6J and B6(Cg)-Tyr^c-2J/J embryos that were obtained at the 8-cell stage. Microinjected embryos were transferred to the oviduct of E0.5 pseudopregnant F1 (CBA×C57BL/6J) females. Chimeric embryos were harvested at E13.5 and assayed for GFP expression in the gonads with a fluorescence microscope. Chimeric mice were mated with albino B6(Cg)-Tyr^c-2J/J mice to assay for germline contribution. All animal work was performed according to IACUC guidelines.

Retrovirus Constructs, Packaging and Infection cDNA sequences of Nr5a2 and other factors were PCR amplified from either mouse ESC cDNA or commercial plasmids (Open Biosystems). cDNA sequences of Nr5a2 SUMO mutants (2KR: K173R, K289R and 5KR: K173R, K213R, K289R, K329R, K389R) were amplified from donated constructs (Yang et al., 2009). Nr5a2 ligand and DNA binding mutants were PCR amplified with the appropriate primers. Amplified coding sequences were verified by sequencing and cloned into MMLV-based pMX retroviral vector. shRNA knockdown constructs with their respective promoter regions were transferred from the pSUPER.puro vector to the pMX vector. Retroviruses were generated as described previously (Takahashi and Yamanaka, 2006). 3T3 cells were infected with pMX retroviruses harboring the GFP gene. After 48 h of infection, FACs was perform to quantify the proportion of GFP-positive cells. Number of transducing units was calculated as previously described (Tiscornia et al., 2006). Number of transducing units was used to calculate the amount of virus needed to achieve a multiplicity of infection (MOI) of 5 (Park et al., 2008). For iPSC generation, viruses encoding the different factors each with a MOI of 5 were introduced to MEFs at 70% confluence in DMEM containing 15% FBS and 6 ng ml⁻¹ polybrene. At 1 dpi, medium was changed to fresh MEF medium. At 2 dpi, cells were passaged to MEF feeders and cultured for 6 days in culture medium containing FBS followed by an additional 5-15 days in culture medium containing KSR.

RNA Extraction, Reverse Transcription and Quantitative Real-Time PCR

Methods are as described previously (Feng et al., 2009).

Bisulfite Genomic Sequencing

Genomic DNA was bisulfite-treated with the Imprint™ DNA modification kit (Sigma) according to the manufacturer's instructions. Promoter regions of Pou5f1 and Nanog were amplified by PCR and cloned into the pCR2.1-TOPO vector (Invitrogen) and sequence-verified with the M13 forward and M13 reverse primers. Primer sequences used in the PCR amplification of the Pou5f1 and Nanog promoter regions are 5'-ATGGGTTGAAATATTGGGTTTATTTA-3' (SEQ ID NO: 11), 5'-CCACCCTCTAACCTTAAC-CTCTAAC-3' (SEQ ID NO: 12) and 5'-GATTTTGTAG-GTGGGATTAATTGTGAATTT-3' (SEQ ID NO: 13), 5'-ACCAAAAAAACCCACACTCATATCAATATA-3' (SEQ ID NO: 14), respectively.

Karyotyping

PSCs were treated with colcemid (Invitrogen), harvested by standard hypotonic treatment, and fixed with methanol: acetic acid (3:1). Slides were air-dried before G-band karyotyping.

Genotyping

Each PCR amplification reaction was performed with 300 ng of genomic DNA harvested from either iPSCs, ESCs, MEFs or embryo.

```
Sense primer sequence:
                                   (SEQ ID NO: 15)
5'-GACGGCATCGCAGCTTGGATACAC-3'.

Antisense primer sequences are:
Nr5a2:
                                   (SEQ ID NO: 16)
5'-GACGCAATAGCTGTAAGTCCATG-3';

Sox2:
                                   (SEQ ID NO: 17)
5'-GCTTCAGCTCCGTCTCCATCATGTT-3';

Klf4:
                                   (SEQ ID NO: 18)
5'-GCCATGTCAGACTCGCCAGG-3';

c-Myc:
                                   (SEQ ID NO: 19)
5'-TCGTCGCAGATGAAATAGGGCTG-3';
and Pou5f1:
                                   (SEQ ID NO: 24)
5'-CCAATACCTCTGAGCCTGGTCCGAT-3'.
```

EB-Mediated In Vitro Differentiation

For EB formation, iPSCs were trypsinized and cultured in Petri-dish for 4-5 days in iPSC culture medium in the absence of LIF and β-mercaptoethanol. EBs were transferred to gelatin-coated plates and cultured for 5-6 days with the addition of 1 μM retinoic acid (Sigma). Samples were fixed in 4% paraformaldehyde, permeabilized with 1% triton X-100, blocked with 8% FBS, and stained with anti-Gata-4 (1:100, sc-25310, Santa Cruz), anti-Nestin (1:100, sc-58813, Santa Cruz) or anti-α-Smooth Muscle Actin (1:100, ab18460, Abcam). Samples were then stained with the secondary antibody, Alexa Fluor 546 conjugated anti-mouse (1:1000, Invitrogen) followed by staining of the nuclei with Hoechst (1:4000, Invitrogen).

Teratoma Assay

PSCs were harvested by trypsinization and resuspended to $1\times10^7$ cells ml$^{-1}$ in 0.9% saline. 100 μl of the cell suspension was injected subcutaneously into each dorsal flank of avertin-anesthetized SCID mice. Teratomas were dissected after 3-4 weeks, weighted and fixed in Bouin's solution, before embedding in paraffin. Paraffin-embedded tissue was sectioned and stained with Mallory's Tetrachrome as previously described (Wang and Lufkin, 2000).

Immunofluorescence Microscopy and Alkaline Phosphatase Staining

PSCs cultured on gelatin-coated cover slips were fixed with 4% paraformaldehyde, permeabilized in 1% triton X-100 and blocked with 8% FBS. After blocking, samples were stained with anti-Nanog (1:50, RCAB0002 PF, CosmoBio) or anti-SSEA-1 (1:200, MAB4301, Chemicon), before staining with Alexa Fluor 568 conjugated anti rabbit (1:300, Invitrogen) or Alexa Fluor 546 conjugated anti-mouse IgM (1:2000, Invitrogen), respectively. Nuclei were then counterstained with Hoechst (Invitrogen). Alkaline phosphatase detection was performed using a commercial ESC characterization kit (Chemicon) according to the manufacturer's protocol.

Western Analysis

Cells were lysed with RIPA buffer (Pierce) supplemented with protease inhibitor cocktail (Roche). Protein concentration was measured with a Bradford assay kit (Bio-Rad). 50 μg of cell lysate was resolved on a 10% SDS-polyacrylamide gel and transferred to a polyvinylidine difluoride membrane (Millipore). The membrane was blocked with 5% skim milk. After blocking, the blot was incubated with either anti-HA (1:2000, sc-7392, Santa Cruz), anti-Nr5a2 (1:2000, ab18293, Abcam) or anti-actin (1:2000, sc-1616, Santa-Cruz) primary antibodies for 1 h, washed with PBST and incubated with either horse-radish peroxidase (HRP)-conjugated anti-mouse IgG (1:5000, 1858413, Pierce), HRP-conjugated rabbit IgG (1:5000, sc-2004, Santa Cruz) or HRP-conjugated anti-goat IgG (1:5000, sc-2768, Santa Cruz), respectively. After washing with PBST, signals were detected using the Western Blotting Luminol Reagents (Santa Cruz).

Tunel Assay

MEFs were infected with respective viruses and infection media was replaced with fresh MEF media after 24 h. Cells were harvested for tunel assay 78 h after infection. For positive control, uninfected MEFs were subjected to DNase 1 (Ambion) treatment before cell labeling. Tunel labeling was performed using a commercial kit according to the manufacturer's protocol (Roche). After labeling, cells were subjected to FACS analysis.

ChIP Assay

ChIP assays were performed as described previously (Loh et al., 2006). In general, cells were crosslinked with 1% formaldehyde for 10 min at room temperature and the formaldehyde was quenched with 125 mM glycine. Cell lysates were sonicated and chromatin extracts were immunoprecipitated with anti-H3K4me3 (ab8580, Abcam), anti-H3K27me3 (07-449, Millipore) or anti-HA (sc-7392, Santa Cruz) antibodies. Quantitative PCR analyses were performed as previously described (Feng et al., 2009).

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

While the invention has been described with reference to specific methods and embodiments, it will be appreciated that various modifications and changes may be made without departing from the invention.

The invention claimed is:

1. A method for inducing pluripotent stem cells comprising the steps of:
   (a) culturing cells in vitro;
   (b) introducing, into cultured cells of step (a), exogenous reprogramming factor genes, wherein the exogenous reprogramming factor genes consist of
      (i) Nr5a2 or a sumoylated mutant thereof, Sox2 and Klf4;
      (ii) Nr5a2 or a sumoylated mutant thereof, Sox2, Klf4 and c-Myc; or
      (iii) Nr5a2 or a sumoylated mutant thereof, Nr5a1 or a sumoylated mutant thereof, Sox2, Klf4 and c-Myc, thereby inducing pluripotent stem cells in vitro.

2. The method of claim 1, wherein the nuclear receptor from subfamily 5 gene encodes a polypeptide that comprises the amino acid sequence of SEQ ID NO: 9.

3. The method of claim 1, wherein the nuclear receptor from subfamily 5 gene comprises the nucleotide sequence of SEQ ID NO: 1, SEQ ID NO: 3, SEQ ID NO: 5 or SEQ ID NO: 7.

4. The method of claim 1, wherein the nuclear receptor from subfamily 5 gene encodes a polypeptide that comprises the amino acid sequence of SEQ ID NO: 2, SEQ ID NO: 4, SEQ ID NO: 6, SEQ ID NO: 8, SEQ ID NO: 9 or SEQ ID NO: 10.

5. The method of claim 1, wherein the exogenous reprogramming factor genes are introduced into cultured cells of step (a) by introducing an expression vector comprising a polynucleotide that encodes the exogenous reprogramming factor genes, wherein the polynucleotide is operably linked to a regulatory sequence capable of directing expression of said polynucleotide in a host cell for inducing pluripotent stem cells.

6. A method for inducing pluripotent stem cells for treating a patient in need of a pluripotent stem cell treatment comprising the steps of:
   (a) isolating cells from an individual donor;
   (b) culturing the cells in vitro;
   (c) introducing, into cultured cells of step (b), exogenous reprogramming factor genes, wherein the exogenous reprogramming factor genes consist of
      (i) Nr5a2 or a sumoylated mutant thereof, Sox2 and Klf4;
      (ii) Nr5a2 or a sumoylated mutant thereof, Sox2, Klf4 and c-Myc; or
      (iii) Nr5a2 or a sumoylated mutant thereof, Nr5a1 or a sumoylated mutant thereof, Sox2, Klf4 and c-Myc, thereby inducing pluripotent stem cells, and
   (d) introducing pluripotent stem cells of step (c) to the patient in need of a pluripotent stem cell treatment.

7. The method of claim 6, wherein the nuclear receptor from subfamily 5 gene encodes a polypeptide that comprises the amino acid sequence of SEQ ID NO: 9.

8. The method of claim 6, wherein the nuclear receptor from subfamily 5 gene comprises the nucleotide sequence of SEQ ID NO: 1, SEQ ID NO: 3, SEQ ID NO: 5 or SEQ ID NO: 7.

9. The method of claim 6, wherein the nuclear receptor from subfamily 5 gene encodes a polypeptide that comprises the amino acid sequence of SEQ ID NO: 2, SEQ ID NO: 4, SEQ ID NO: 6, SEQ ID NO: 8, SEQ ID NO: 9 or SEQ ID NO: 10.

10. A method of making a pluripotent stem cell line comprising:
   (a) culturing cells in vitro;
   (b) introducing, into cultured cells of step (a), exogenous reprogramming factor genes, wherein the exogenous reprogramming factor genes consist of
      (i) Nr5a2 or a sumoylated mutant thereof, Sox2 and Klf4;
      (ii) Nr5a2 or a sumoylated mutant thereof, Sox2, Klf4 and c-Myc; or
      (iii) Nr5a2 or a sumoylated mutant thereof, Nr5a1 or a sumoylated mutant thereof, Sox2, Klf4 and c-Myc, and
   (c) passaging the pluripotent stem cells, thereby making a pluripotent stem line.

11. A method for inducing pluripotent stem cells in vitro, the method comprising culturing in vitro cells that express exogenous reprogramming factor genes, wherein the exogenous reprogramming factor genes consist of
   (a) Nr5a2 or a sumoylated mutant thereof, Sox2 and Klf4;
   (b) Nr5a2 or a sumoylated mutant thereof, Sox2, Klf4 and c-Myc; or
   (c) Nr5a2 or a sumoylated mutant thereof, Nr5a1 or a sumoylated mutant thereof, Sox2, Klf4 and c-Myc, thereby inducing pluripotent stem cells in vitro.

12. The method of claim 1, wherein the cells of step (a) are differentiated cells.

13. The method of claim 6, wherein the cells of step (a) are differentiated cells.

14. The method of claim 10, wherein the cells of step (a) are differentiated cells.

15. The method of claim 11, wherein the cells cultured in vitro are differentiated cells.

* * * * *